US008734793B2

(12) United States Patent
Tu et al.

(10) Patent No.: US 8,734,793 B2
(45) Date of Patent: May 27, 2014

(54) RECOMBINANT ANTIBODIES AGAINST HEPATITIS C VIRUS AND METHODS OF OBTAINING AND USING SAME

(75) Inventors: Bailin Tu, Lake Bluff, IL (US); Joan D. Tyner, Beach Park, IL (US); James W. Scheffel, Shelby, NC (US); Michael K. White, Framingham, MA (US); Jeffrey M. Werneke, Grayslake, IL (US); Robert N. Ziemann, Palatine, IL (US); David J. Hawksworth, Lake Villa, IL (US); Mary S. Pinkus, Chicago, IL (US); Robin A. Gutierrez, Gurnee, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 60 days.

(21) Appl. No.: 12/951,735

(22) Filed: Nov. 22, 2010

(65) Prior Publication Data

US 2011/0263436 A1 Oct. 27, 2011

Related U.S. Application Data

(62) Division of application No. 11/633,810, filed on Dec. 5, 2006, now Pat. No. 7,858,752.

(51) Int. Cl.
*A61K 39/395* (2006.01)
*A61K 39/00* (2006.01)

(52) U.S. Cl.
USPC .......................... 424/133.1; 424/228.1; 435/5

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,308,750 A | 5/1994 | Mehta et al. | |
| 5,595,868 A | 1/1997 | Habets et al. | |
| 5,753,430 A | 5/1998 | Mehta et al. | |
| 5,792,456 A * | 8/1998 | Yelton et al. | 424/133.1 |
| 6,015,662 A | 1/2000 | Hackett, Jr. et al. | |
| 6,030,792 A | 2/2000 | Otterness et al. | |
| 6,054,264 A | 4/2000 | Chien et al. | |
| 6,331,415 B1 | 12/2001 | Cabilly et al. | |
| 6,727,092 B2 | 4/2004 | Shah et al. | |
| 7,049,060 B2 | 5/2006 | Bahl | |
| 7,091,324 B2 | 8/2006 | Foung et al. | |
| 7,166,426 B2 * | 1/2007 | Arcangel et al. | 435/5 |
| 7,314,919 B2 * | 1/2008 | Burioni et al. | 530/387.1 |
| 7,871,625 B2 * | 1/2011 | Chien et al. | 424/189.1 |
| 7,988,971 B2 * | 8/2011 | Dimitrov et al. | 424/147.1 |
| 2003/0148333 A1 | 8/2003 | Bahl | |
| 2003/0152948 A1 | 8/2003 | Shah et al. | |
| 2004/0110226 A1 | 6/2004 | Lazar et al. | |
| 2004/0208887 A1 | 10/2004 | Drakenberg et al. | |
| 2004/0214994 A1 * | 10/2004 | Burioni et al. | 530/388.3 |
| 2008/0131912 A1 | 6/2008 | Tu et al. | |

FOREIGN PATENT DOCUMENTS

| | | |
|---|---|---|
| EP | 1881064 A2 | 1/2008 |
| WO | WO2006037604 A1 | 4/2006 |
| WO | WO2007/011698 | 1/2007 |

OTHER PUBLICATIONS

Rudikoff et al. Proc Natl Acad Sci USA , 1984, vol. 79, pp. 2162-2166.*
Altschul S.F., et al., "Basic Local Alignment Search Tool," J. Mol. Biol., 1990, vol. 215, pp. 403-410.
Barbas III C.F., et al., "Semisynthetic Combinatorial Antibody Libraries: A Chemical Solution to the Diversity Problem," Proceedings of the National Academy of Sciences, 1992, vol. 89 (10), pp. 4457-4461.
Brodeur B.R., et al., "Mouse-Human Myeloma Partners for the Production of Heterohybridomas" in: Monoclonal Antibody Production Techniques and Applications, Schook L.B., ed., Marcel Dekker, 1987, pp. 51-63.
Chao G., et al., "Fine Epitope Mapping of Anti-Epidermal Growth Factor Receptor Antibodies through Random Mutagenesis and Yeast Surface Display," Journal of Molecular Biology, 2004, vol. 342 (2), pp. 539-550.
Clackson T., et al., "Making Antibody Fragments Using Phage Display Libraries," Nature, 1991, vol. 352 (6336), pp. 624-628.
Courouce, et al., "Efficacy of HCV Core Antigen Detection During the Preseroconversion Period," Transfusion, 2000, vol. 40, pp. 1198-1202.
Dou, et al., "Antigenic Heterogeneity of the Hepatitis C Virus NS5A Protein," Journal of Clinical Microbiology, 2002, vol. 40(1), pp. 61-67.
Galfre G., et al., "Antibodies to Major Histocompatibility Antigens Produced by Hybrid Cell Lines," Nature, 1977, vol. 266 (5602), pp. 550-552.
Coding, et al., Monoclonal Antibodies: Production of Monoclonal Antibodies, 1986, pp. 59-103.
Hackett, Jr., et al., Journal of Clinical Microbiology, 1998, vol. 36(5), pp. 1177-1284.
Hamilton, R. G., "Engineered Human Antibodies as Immunologic Quality Control Reagents," Ann. Biol. Clin., 1990, vol. 48, pp. 473-477.

(Continued)

*Primary Examiner* — Bao Li
(74) *Attorney, Agent, or Firm* — Irene M. Reininger

(57) ABSTRACT

Recombinant antibodies, including chimeric antibodies, specific for hepatitis C (HCV) antigenic proteins are provided. The recombinant antibodies specifically bind to diagnostically relevant regions of HCV proteins and are thus suitable for use, for example, as diagnostic reagents for the detection of HCV, and/or as standardization reagents or positive control reagents in assays for the detection of HCV. The recombinant antibodies can also be used in the treatment or prevention of a HCV infection.

11 Claims, 12 Drawing Sheets

(56) References Cited

OTHER PUBLICATIONS

Hamilton, R.G., "Application of Engineered Chimeric Antibodies to the Calibration of Human Antibody Standards," Ann. Biol. Clin., 1991, vol. 49, pp. 242-248.

International Search Report and Written Opinion for Application No. PCT/US2007/086516, mailed on Sep. 17, 2008, 18 pages.

Johnson K.S., et al., "Human Antibody Engineering," Current Opinion in Structural Biology, 1993, vol. 3, pp. 564-571.

Jolivet Reynaud, et al., "HCV Core Immunodominant Region Analysis Using Mouse Monoclonal Antibodies and Human Sera: Characterization of Major Epitopes Useful for Antigen Detection," Journal of Medical Virology, 1998, vol. 56 (4), pp. 300-309.

Khudyakov, et al., "Linear B-cell Epitopes of the NS3-NS4-NS5 Proteins of the Hepatitis C Virus as Modeled with Synthetic Peptides," Virology, 1995, vol. 206(1), pp. 666-672.

Kohler G., et al., "Continuous Cultures of Fused Cells Secreting Antibody of Predefined Specificity," Nature, 1975, vol. 256 (5517), pp. 495-497.

Kozbor D., et al., "A Human Hybrid Myeloma for Production of Human Monoclonal Antibodies," Journal of Immunolology, 1984, vol. 133 (6), pp. 3001-3005.

Li, et al., "Chimeric Monoclonal Antibodies to Hypervariable Region 1 of Hepatitis C Virus," Journal of General Virology, 2005, vol. 86, pp. 1709-1716.

Marks J.D., et al., "By-passing Immunization. Human Antibodies from V-gene Libraries Displayed on Phage," Journal of Molecular Biology, 1991, vol. 222, pp. 581-597.

Masalova, et al., "Characterization of Monoclonal Antibodies and Epitope Mapping of the NS4 Protein of Hepatitis C Virus," Immunology Letters, 2002, vol. 83 (3), pp. 187-196.

Menez, et al., "Crystal Structure of a Hydrophobic Immunodominant Antigenic Site on Hepatitis C Virus Core Protein Complexed to Monoclonal Antibody 19D9D6," Journal of Immunology, 2003, vol. 170 (4), pp. 1917-1924.

Miller, et al., "Hepatitis C Virus Shares Amino Acid Sequence Similarity with Pestiviruses and Flavivirusesas Well as Members of Two Plant Virus Supergroups," Proc. Natl. Acad. Sci. USA, 1990, vol. 87, pp. 2057-2061.

Morrison S.L., et al., "Chimeric Human Antibody Molecules: Mouse Antigen-Binding Domains with Human Constant Region Domains," Proceedings of National Academy of Sciences, 1984, vol. 81 (21), pp. 6851-6855.

Munson P.J., et al., "Ligand: A Versatile Computerized Approach for Characterization of Ligand-Binding Systems," Analytical Biochemistry, 1980, vol. 107 (1), pp. 220-239.

Naess, et al., "Quantitation of IgG Subclass Antibody Responses After Immunization With a Group B Meningococcal Outer Membrane Vesicle Vaccine, Using Monoclonal Mouse-human Chimeric Antibodies as Standards," Journal of Immunological Methods, 1996, vol. 196, pp. 41-49.

Neville J.A., et al., "Antigenic Variation of Core, NS3, and NS5 Proteins Among Genotypes of Hepatitis C Virus," Journal of Clinical Microbiology, 1997, vol. 35 (12), pp. 3062-3070.

Rudikoff S., et al., "Single Amino Acid Substitution Altering Antigen-Binding Specificity," Proceedings of the National Academy of Sciences of the United States of America, 1982, vol. 79 (6), pp. 1979-1983.

Schuurman, et al., "Production of a Mouse/human Chimeric IgE Monoclonal Antibody to the House Dust Mite Allergen Der p 2 and its Use for the Absolute Quantification of Allergen-specific IgE," J. Allergy Clin. Immunology, 1997, vol. 99 (4), pp. 545-550.

Schwartz R.M., et al., "Matrices for Detecting Distant Relationships" in: Atlas of Protein Sequence and Structure, Dayhoff M.O., ed., National Biomedical Research Foundation, 1978, vol. 5 (Suppl. 3), pp. 353-358.

Smith K.A., et al., "Demystified Recombinant Antibodies," Journal of Clinical Pathology, 2004, vol. 57 (9), pp. 912-917.

Smith T.F., "Comparison of Biosequences," Advances in Applied Mathematics, 1981, vol. 2, pp. 482-489.

Smith T.F., et al., "Identification of Common Molecular Subsequences," Journal of Molecular Biology, 1981, vol. 147 (1), pp. 195-197.

Supplementary Partial European Search Report for Application No. EP07865243, dated Nov. 23, 2010, 15 pages.

Tu, Bailin, et al., "Generation and Characterization of Chimeric Antibodies Against NS3, NS4, NS5, and Core Antigens of Hepatitis C Virus," Clinical and Vaccine Immunology, 2010, vol. 17, No. 6, pp. 1040-1047.

Wands J.R., et al., "High Affinity Monoclonal Antibodies to Hepatitis B Surface Antigen (HBsAg) Produced by Somatic Cell Hybrids," Gastroenterology, 1981, vol. 80 (2), pp. 225-232.

Weiner, et al., "Variable and Hypervariable Domains Are Found in the Regions of HCV Corresponding to the Flavivirus Envelope and NS1 Proteins and the Pestivirus Envelope Glycoproteins," Virology, 1991, vol. 180, pp. 842-848.

\* cited by examiner

A.
CAGATCCAGTTGGTGCAGTCTGGACCTGAGCTGCAGAAGCCTGGAAAGACA
GTCAAGATCTCCTGCAAGACTTCTGGTTATACCTTCACAGACTATCCAATGCA
CTGGGTGAAGCAGGCTCCAGGAAAGGGTTTAAAGTGGATGGGCTGGATAAA
CACTGAGACTGGTGAGCCAACACGTGTAGATGACTTCAAGGGACGTTTTGCC
TTCTCTTTGGAAACCTCTGCCAGCACTGCCTATTTGCAGATCAACAACCTCAA
AGATGAGGACACGGCCACATATTTCTGCGCTAGAGGGGGTGGGGTCCGACG
CCAGGTTATGGACTACTGGGGTCAAGGAACCTCAGTCACCGTCTCCTCA

B.
GACATTGTGATGTCACAGTCTCCATCCTCCCTGGCTGTGTCAGCAGGAGAGA
AGGTCACTATGAGCTGCAAATCCAGTCAGAGTCTGCTCAATAGTAGAACCCG
AAAGAACTACTTGGTTTGGTACCAGCAGAAACCAGGGCAGTCTCCTAAACTG
CTGATCTACTGGGCATCCACTAGGGATTCTGGGGTCCCTGATCGCTTCACAG
GCAGTGGATCTGGGACAGATTTCACTCTCACCATCAGCAGTGTGCAGGCTGA
AGACCTGGCAGTTTATTACTGCAAGCAATCTTATAATCTGTACACGTTCGGA
GGGGGGACCAAGCTGGAAATAAAAC

C.
QIQLVQSGPELQKPGKTVKISCKTSGYTFTDYPMHWVKQAPGKGLKWMGWINT
ETGEPTRVDDFKGRFAFSLETSASTAYLQINNLKDEDTATYFCARGGGVRRQVM
DYWGQGTSVTVSS

D.
DIVMSQSPSSLAVSAGEKVTMSCKSSQSLLNSRTRKNYLVWYQQKPGQSPKLLI
YWASTRDSGVPDRFTGSGSGTDFTLTISSVQAEDLAVYYCKQSYNLYTFGGGTK
LEIKR

FIGURE 2A-D

A.
GAAGTGAAGCTGGTGGAGTCTGGGGGAGGCTTAGTGCAGCCTGGAGGGTCC
CTGAAACTCTCCTGTGCAACCTCT<u>GGATTCACTTTCAGTGACTATTAT</u>ATGTA
TTGGGTTCGCCAGACTCCAGAGAAGAGGCTGGAGTGGGCCGCATAC<u>ATTAGT
AATGGTGCTGGTAGCACC</u>TATTATCCAGACACTGTAAAGGGCCGATTCACCA
TCTCCAGAGACAATGCCAAGAACACCCTGTACCTGCAAATGAGCCGTCTGAA
GTCTGAGGACACAGCCATGTATTACTGT<u>GCAAGAGGCCTCTGGGACGGCCTT
GACTAC</u>TGGGGCCAAGGCACCACTCTCACAGTCTCCTCG

B.
GATGTTGTGATGGCCCAAACTCCACTCTCCCTGCCTGTCAGTCTTGGAGATCA
AGCCTCCATCTCTTGCAGATCTAGT<u>CAGAGCCTTGTACACAGTAATGGAAAC
ACCTAT</u>TACATTGGTACCTGCAGAGGCCAGGCCAGTCTCCAAAGCTCCTGA
TCTAC<u>AAAGTTTCC</u>AACCGATTTTCTGGGGTCCCAGACAGGTTCAGTGGCAG
TGGATCAGGGACAGATTTCACACTCAAGATCAGCAGAGTGGAGGCTGAGGA
TCTGGGAGTTTATTTCTGC<u>TCTCAAAGTACACATGTTCCGTACAC</u>GTTCGGAG
GGGGGACCAAGCTGGAAATAAAACGT

C.
EVKLVESGGGLVQPGGSLKLSCATS<u>GFTFSDYY</u>MYWVRQTPEKRLEWAAY<u>ISN
GAGST</u>YYPDTVKGRFTISRDNAKNTLYLQMSRLKSEDTAMYYC<u>ARGLWDGLD
Y</u>WGQGTTLTVSS

D.
DVVMAQTPLSLPVSLGDQASISCRSS<u>QSLVHSNGNTY</u>LHWYLQRPGQSPKLLIY
<u>KVS</u>NRFSGVPDRFSGSGSGTDFTLKISRVEAEDLGVYFC<u>SQSTHVPYT</u>FGGGTKL
EIKR

FIGURE 4A-D

A.
CAGATCCAGTTGGTGCAGTCTGGACCTGAGCTGAAGAAGCCTGGAGAGACA
GTCAAGATCTCCTGCAAGGCTTCTGGTTATACCTTCACAGACTATTCAATGCA
CTGGGTGAACCAGGCTCCAGGAAAGGGTTTAAAGTGGATGGGCTGGATAAA
CACTGAGACTGGTGAGCCAACATATGCAGATGACTTCAAGGGACGGTTTGCC
TTCTCTTTGGAAACCTCTGCCAGCACTGCCTATTTGCAGATCAACAACCTCAA
AAATGAGGACACGGCTACATATTTCTGTACTAGGGGAGGCACGGGCTACTGG
GGCCAAGGCACCACTCTCACAGTCTCCTCA

B.
GATGTTGTGATGACCCAAACTCCACTCTCCCTGCCTGTCAGTCTTGGAGATCA
AGCCTCCATCTCTTGCAGATCTAGTCAGAGCCTTGTATACAGTAATGGAAAC
ACCTATTTACATTGGTACCTGCAGAAGCCAGGCCAGTCTCCAAAGCTCCTGA
TCTACAAAGTTTCCAACCGATTTTCTGGGGTCCCAGACAGGTTCAGTGGCAG
TGGATCAGGGACAGATTTCACACTCAAGATCAGCAGAGTGGAGGCTGAGGA
TCTGGGAGTTTATTTCTGCTCTCAAAGTACACATGTTCCGTGGACGTTCGGTG
GAGGCACCAAGCTGGAAATCAAACGG

C.
QIQLVQSGPELKKPGETVKISCKASGYTFTDYSMHWVNQAPGKGLKWMGWINT
ETGEPTYADDFKGRFAFSLETSASTAYLQINNLKNEDTATYFCTRGGTGYWGQG
TTLTVSS

D.
DVVMTQTPLSLPVSLGDQASISCRSSQSLVYSNGNTYLHWYLQKPGQSPKLLIY
KVSNRFSGVPDRFSGSGSGTDFTLKISRVEAEDLGVYFCSQSTHVPWTFGGGTKL
EIKR

GAGGTTCAGCTGCAGCAGTCTGGGGCAGAGCTTGTGAAGCCAGGGGCCTCA
GTCAAGTTGTCCTGCACAGCTTCT<u>GGCTTCAACATTAAAGACACCTAT</u>ATGC
ACTGGGTGAAGCAGAGGCCTGAACAGGGCCTGGAGTGGATTGGAAGG<u>ATTG
ATCCTGCGAATGGTAATACT</u>AAATATGACCCGAAGTTCCAGGGCAAGGCCAC
TATAACAGCAGACACATCCTCCAACACAGCCTACCTGCAGCTCAGCAGCCTG
ACATCTGAGGACACTGCCGTCTATTACTGT<u>GCTAGATCGCGGGAGTTTGCTT
AC</u>TGGGGCCAAGGGACTCTGGTCACTGTCTCTGCA

B.

GACATTGTGATGTCACAGTCTCCATCCTCCCTAGCTGTGTCAGTTGGAGAGA
AGGTTACTATGAGCTGCAAGTCCAGT<u>CAGAGCCTTTTATATAGTAGCAATCA
AAAGAACTAC</u>TTGGCCTGGTACCAGCAGAAACCAGGGCAGTCTCCTAAACTG
CTGATTTAC<u>TGGGCATCC</u>ACTAGGGAATCTGGGGTCCCTGATCGCTTCACAG
GCAGTGGATCTGGGACAGATTTCACTCTCACCATCAGCAGTGTGAAGGCTGA
AGACCTGGCAGTTTATTACTGT<u>CAGCAATATTATAGCTATCCGCTCACGTTCG
GTGCTGGGACCAAGCTGGAGCTGAAACGG

C.

EVQLQQSGAELVKPGASVKLSCTAS<u>GFNIKDTY</u>MHWVKQRPEQGLEWIGR<u>IDP
ANGNT</u>KYDPKFQGKATITADTSSNTAYLQLSSLTSEDTAVYYC<u>ARSREFAY</u>WG
QGTLVTVSA

D.

DIVMSQSPSSLAVSVGEKVTMSCKSS<u>QSLLYSSNQKNY</u>LAWYQQKPGQSPKLLI
Y<u>WAS</u>TRESGVPDRFTGSGSGTDFTLTISSVKAEDLAVYYC<u>QQYYSYPLT</u>FGAGT
KLELKR

CAGATCCAGTTGGTGCAGTCTGGACCTGAGCTGAAGAAGCCTGGAGAGACA
GTCAAGATCTCCTGCAAGGCTTCT<u>GGGTATACCTTCACAAACTATGGA</u>ATGA
ACTGGGTGAAGCAAGCTCCAGGAAAGGGTTTAAAGTGGATGGGCTGG<u>ATAA</u>
<u>ACACCAACACTGGAGAGCCA</u>ACATATGCTGAAGAGTTCAAGGGACGGTTTG
CCTTCTCTTTGGAAACCTCTGCCATCACTGCCTATTTGCAGATCAACAACCTC
AAAAATGAGGACACGGCTACATATTTCTGT<u>GCAAGAGCGGGGGGAGATTAC</u>
<u>TACGATAGTAGCTACGACTATGCTATGGACTAC</u>TGGGGTCAAGGAACCTCAG
TCACCGTCTCCTCA

B.

GACATTGTGCTGACCCAATCCCCAGCTTCTTTGGCTGTGTCTCTAGGGCAGAG
GGCCACCATCTCCTGCAAGGCCAGC<u>CAAAGTGTTGATTATGATGGTGATAGT</u>
<u>TAT</u>ATGAACTGGTACCAACAGAAACCAGGACAGCCACCCAAACTCCTCATCT
AT<u>GCTGCATCC</u>AATCTAGAATCTGGGATCCCAGCCAGGTTTAGTGGCAGTGG
GTCTGGGACAGACTTCACCCTCAACATCCATCCTGTGGAGGAGGAGGATGCT
GCAACCTATTACTGT<u>CAGCAAAGTAATGAGGATCCGTGGACG</u>TTCGGTGGAG
GCACCAAGCTGGAAATCAAACGT

C.

QIQLVQSGPELKKPGETVKISCKAS<u>GYTFTNYGMN</u>WVKQAPGKGLKWMGW<u>IN</u>
<u>TNTGEPTY</u>AEEFKGRFAFSLETSAITAYLQINNLKNEDTATYFC<u>ARAGGDYYDSS</u>
<u>YDYAMDY</u>WGQGTSVTVSS

D.

DIVLTQSPASLAVSLGQRATISCKAS<u>QSVDYDGDSYMN</u>WYQQKPGQPPKLLIY<u>A</u>
<u>ASN</u>LESGIPARFSGSGSGTDFTLNIHPVEEEDAATYYC<u>QQSNEDPWT</u>FGGGTKLE
IKR

FIGURE 11A-D

RECOMBINANT ANTIBODIES AGAINST HEPATITIS C VIRUS AND METHODS OF OBTAINING AND USING SAME

RELATED APPLICATION INFORMATION

This application is a divisional application of U.S. patent application Ser. No. 11/633,810, filed on Dec. 5, 2006, now allowed as now U.S. Pat. No. 7,858,752, the contents of which is incorporated herein by reference in its entirety.

FIELD OF THE INVENTION

The present invention relates among other things to the field of recombinant antibodies and, in particular, to recombinant antibodies including chimeric antibodies against the hepatitis C virus (HCV).

BACKGROUND OF THE INVENTION

Hepatitis C Virus (HCV) is now recognized as being the primary cause of transfusion associated non A, non B (NANB) hepatitis. HCV is a single stranded, positive sense RNA virus with similarities to flaviviruses and pestiviruses (Miller R H and Purcell R H. Proc Natl Acad Sci. (1991) 87, 2057; Weiner A J, et al. Virology (1990) 180, 842) and is in global distribution. HCV contains a plus-strand RNA genome of approximately 10,000 nucleotides that encodes a polyprotein precursor of about 3000 amino acids. The polyprotein is co- and post-translationally processed by cellular and viral proteases into mature structural and non-structural proteins. The structural proteins include the core protein and the envelope glyco-proteins, E1 and E2. The non-structural proteins include the NS2-3 auto-protease, the NS3 serine protease, a NTPase/RNA helicase domain in the carboxy terminal two-thirds of NS3, the NS4A polypeptide, the NS4B and NS5A proteins, and the NS5B RNA-dependent RNA polymerase. The HCV genome is heterogeneous and has been classified into six major genotypes (1-6), whose nucleotide and deduced amino acid sequences vary by about 30% over the entire genome (see, Neville, J. A. et al., J. Clin. Microbiol., 35:3062-3070 (1997)).

Infection with HCV is currently diagnosed by direct detection of viral RNA by PCR or by detection of anti-HCV antibodies (generally to the HCV structural core protein or non-structural NS3 protein). More recently HCV antigen assays have been developed which demonstrate that HCV core protein antigens can be detected in a sample sooner than antibodies can be detected. Studies have shown that the average time from the first viremic bleed to the first HCV antigen positive bleed is estimated at 2.0 days and that the average time to the first HCV antibody positive bleed at 50.8 days (Couroucé A M, et al. Transfusion, (2000) 40, 1198-1202).

Currently available HCV test kits that employ anti-HCV antibodies use monoclonal antibodies. Monoclonal antibodies (mAbs) have been emerging over recent years as increasingly important commercial reagents (see, Smith, K. A., et al., J. Clin. Pathol., 57:912-917 (2004)), especially in the area of diagnostics and therapeutics where the exceptionally high degree of directional binding exhibited by mAbs has contributed to their success.

Recent developments in recombinant DNA technology have made it possible to clone the sequences encoding mAbs and to express the antibodies, or fragments of the antibodies, as recombinant proteins. Recombinant antibodies can often be produced more consistently and reliably from recombinant constructs than from the original hybridoma. Recombinant DNA technology has also allowed the creation of combinations of the heavy and light chain variable regions of a desired non-human mAb with human constant regions creating a chimeric antibody (see, for example, U.S. Pat. Nos. 4,816,567 and 6,331,415). The chimeric antibody retains the specificity and affinity of the original non-human monoclonal antibody but causes lower human anti-murine antibody (HAMA) responses when administered therapeutically and also is capable of reacting in existing diagnostic assay formats that measure human immunoglobulin.

Monoclonal and recombinant antibodies to HCV have been described. For example, U.S. Pat. Nos. 5,595,868 and 7,049,060, and U.S. Patent Application 2003/0148333 describe monoclonal antibodies to HCV core protein; U.S. Patent Application 2004/0208887 describes monoclonal antibodies to HCV E1 protein; U.S. Pat. Nos. 5,308,750 and 7,091,324 describe monoclonal antibodies to HCV E2 protein; and U.S. Pat. No. 5,753,430 describes monoclonal antibodies to HCV core protein, NS3 protein and NS4 protein. Human recombinant antibodies, and specifically Fab fragments derived from human antibodies, specific for HCV NS3 protein are described in U.S. Patent Application 2004/0214994. Chimeric antibodies to the hypervariable region 1 (HVR1) of HCV have been described (Li, C. and Allain, J-P., J. Gen. Virol., 86:1709-1716 (2005)). HVR1 is a highly mutated region of 27 residues at the N-terminus of the E2 protein.

The use of "heterologous" chimeric antibodies as quality control reagents or calibrators of immunoassays has been described (Hamilton, R. G., Ann. Biol. Clin., 48:473-477 (1990); Hamilton, R. G., Ann. Biol. Clin., 49:242-248 (1991); Naess, L. M., et al., J. of Immunol. Methods, 196:41-49; Schuurman, J., et al., J. Allergy Clin. Immunol., 99:545-550 (1997)). Heterologous in this context indicates that the chimeric antibody binds to an antigen unrelated to the antigen used in the assay for antibody detection. The use of recombinant mouse-human chimeric antibodies, and specifically recombinant mouse-human chimeric antibodies against Toxoplasma gondii, that bind to same or "homologous" antigen as calibrators or positive controls in assays and kits that measure human antibodies has also been described (U.S. Pat. No. 6,015,662 and Hackett, J. Jr., et al., J. Clin. Microbiol., 36:1277-1284)).

Moreover, many HCV immunoassays use HCV infected patient blood samples to prepare a HCV sensitivity panel. Quality control reagents such as sensitivity panels are human plasma/serum screened for the presence of antibodies against specific epitopes. However, the use of human serum/plasma has several significant disadvantages, including increased regulatory concerns, difficulty in sourcing large volume with high-titer and specificity, lot-to-lot variability, limitations with respect to characterization, and cost.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the invention is to provide recombinant antibodies, including chimeric antibodies, against hepatitis C virus (HCV) and uses thereof. In accordance with one aspect of the present invention, there is provided an immunodiagnostic reagent comprising one or more recombinant antibodies, including chimeric antibodies, that are capable of specifically binding a diagnostically relevant region of a HCV protein. Optionally the one or more recombinant antibodies, including chimeric antibodies, are selected from the group consisting of a recombinant antibody specific for HCV core protein, a recombinant antibody specific for HCV E2 protein, a recombinant antibody specific for HCV NS3 protein, a recombinant antibody specific for HCV NS4 protein, and a recombinant antibody specific for HCV NS5 protein.

In accordance with another aspect of the invention, there is provided a recombinant antibody, including a chimeric antibody, which specifically binds to a diagnostically relevant region of a HCV protein wherein the diagnostically relevant region optionally is selected from the group consisting of a HCV core protein, a HCV NS3 protein, a HCV NS4 protein, and a HCV NS5 protein.

In accordance with another aspect of the invention, there is provided a cell line capable of expressing a chimeric antibody that specifically binds to a diagnostically relevant region of a HCV protein, wherein the cell line optionally is selected from the group consisting of HCV core CHO 201-603-486-333, HCV core CHO 14-153-229sc152, HCV NS3 CHO 17-903-132sc171, HCV NS4 CHO E99H6C34sc203, and HCV NS5 CHO 48-311-271-455. There also is provided a cell line which expresses a mouse monoclonal antibody that specifically binds to a diagnostically relevant region of a hepatitis C virus protein, wherein the cell line optionally is selected from the group consisting of anti-HCV Core 201-603-195, anti-HCV Core 14-153-462, anti-HCV NS3 17-903-127, anti-HCV NS4 E99H6C34, and anti-HCV NS5 48-311-387.

In accordance with another aspect of the present invention, there is provided a method of standardizing a HCV antibody detection assay comprising employing as a sensitivity panel an immunodiagnostic reagent optionally comprising one or more recombinant antibodies, including recombinant chimeric antibodies, that are capable of specifically binding a diagnostically relevant region of a HCV protein. In such a panel, optionally the one or more recombinant antibodies are selected from the group consisting of a recombinant antibody (e.g., a chimeric antibody) specific for HCV core protein, a recombinant antibody (e.g., a chimeric antibody) specific for HCV E2 protein, a recombinant antibody (e.g., a chimeric antibody) specific for HCV NS3 protein, a recombinant antibody (e.g., a chimeric antibody) specific for HCV NS4 protein, and a recombinant antibody (e.g., a chimeric antibody) specific for HCV NS5 protein.

In accordance with another aspect of the present invention, there is provided a method for detecting the presence of HCV antigens comprising contacting a test sample, such as a sample suspected of containing HCV antigens, with an immunodiagnostic reagent comprising one or more recombinant antibodies, including recombinant chimeric antibodies, which each are capable of specifically binding an HCV antigen. Optionally the contacting is done under conditions that allow formation of recombinant antibody:antigen complexes. Further optionally the method comprises detecting any recombinant antibody:antigen complexes formed.

In accordance with another aspect of the present invention, there is provided a method for detecting the presence of HCV antibodies comprising contacting a test sample, such as a sample suspected of containing antibodies to HCV, with one or more antigens specific for the HCV antibodies. Optionally this contacting is done under conditions that allow formation of antigen:antibody complexes, and further optionally the method comprises detecting the antigen:antibody complexes. Still further, the method optionally comprises employing an immunodiagnostic reagent comprising one or more recombinant antibodies, including recombinant chimeric antibodies, wherein each of the antibodies are capable of specifically binding one of the antigens employed in the method, e.g., either as a positive control or standardization reagent.

In accordance with another aspect of the present invention, there is provided a diagnostic kit for the detection of HCV comprising an immunodiagnostic reagent comprising one or more recombinant antibodies, including recombinant chimeric antibodies, that each are capable of specifically binding a diagnostically relevant region of a HCV protein. In such a kit, the one or more recombinant antibodies optionally are selected from the group consisting of a recombinant antibody (e.g., a chimeric antibody) specific for HCV core protein, a recombinant antibody (e.g., a chimeric antibody) specific for HCV E2 protein, a recombinant antibody (e.g., a chimeric antibody) specific for HCV NS3 protein, a recombinant antibody (e.g., a chimeric antibody) specific for HCV NS4 protein, and a recombinant antibody (e.g., a chimeric antibody) specific for HCV NS5 protein.

In accordance with yet another aspect of the present invention, there is provided a method of identifying amino acid residues within an HCV protein epitope that are bound by an antibody that specifically binds to said HCV protein epitope. The method optionally comprises the steps of: (a) obtaining a yeast display library comprising a series of peptides displayed on the surface of host cells (i.e., yeast cells), wherein the peptides have amino acid sequences corresponding to the amino acid sequence of the epitope in which each individual amino acid of the epitope has been sequentially substituted by alanine; (b) contacting the yeast display library with said antibody that is capable specifically binding the epitope under conditions that permit binding of the antibody to the epitope, and (c) identifying those peptides displayed on yeast cells which are not bound by said antibody in step (b), wherein an absence of antibody binding indicates that the yeast displayed peptide contains an alanine residue at an amino acid position bound by said antibody in the epitope.

These and other features, aspects, objects, and embodiments of the invention will become more apparent in the following detailed description in which reference is made to the appended drawings that are exemplary of such features, aspects, objects and embodiments.

BRIEF DESCRIPTION OF THE DRAWINGS

FIGS. 2A-D depict the nucleic acid and amino acid sequences in one embodiment of the present invention of the light and heavy variable regions of an anti-HCV core chimeric antibody (HCV core 201-603-486-333) with underlining denoting the respective complementarity determining regions (CDRs): FIG. 2A: $V_H$ nucleic acid sequence (SEQ ID NO:7); FIG. 2B: $V_L$ nucleic acid sequence (SEQ ID NO:8); FIG. 2C: $V_H$ amino acid sequence (SEQ ID NO:1); and FIG. 2D: $V_L$ amino acid sequence (SEQ ID NO:2).

FIGS. 4A-D depicts the nucleic acid and amino acid sequences in one embodiment of the present invention of the light and heavy variable regions of an anti-HCV NS3 chimeric antibody (HCV NS3 CHO 17-903-132sc171) with underlining denoting the respective complementarity determining regions (CDRs): FIG. 4A: $V_H$ nucleic acid sequence (SEQ ID NO:15); FIG. 4B: $V_L$ nucleic acid sequence (SEQ ID NO:16); FIG. 4C: $V_H$ amino acid sequence (SEQ ID NO:9); and FIG. 4D: $V_L$ amino acid sequence (SEQ ID NO:10).

FIGS. 6A-D depicts the nucleic acid and amino acid sequences in one embodiment of the present invention of the light and heavy variable regions of an anti-HCV NS4 chimeric antibody (HCV NS4 CHO E99H6C34sc203) with underlining denoting the respective complementarity determining regions (CDRs): FIG. 6A: $V_H$ nucleic acid sequence (SEQ ID NO:23); FIG. 6B: $V_L$ nucleic acid sequence (SEQ ID NO:24); FIG. 6C: $V_H$ amino acid sequence (SEQ ID NO:17); and FIG. 6D: $V_L$ amino acid sequence (SEQ ID NO:18).

FIGS. 8A-D depicts the nucleic acid and amino acid sequences in one embodiment of the present invention of the light and heavy variable regions of an anti-HCV NS5 chimeric antibody (HCV NS5 CHO 48-311-271-455) with underlining denoting the respective complementarity determining regions (CDRs); FIG. 8A: $V_H$ nucleic acid sequence (SEQ ID NO:31); FIG. 8B: $V_L$ nucleic acid sequence (SEQ ID NO:32); FIG. 8C: $V_H$ amino acid sequence (SEQ ID NO:25); and FIG. 8D: $V_L$ amino acid sequence (SEQ ID NO:26).

FIGS. 9A-D depicts the epitopes bound by core, NS3, NS4 and NS5 chimeric antibodies in one embodiment of the present invention: FIG. 9A: shows the epitope (SEQ ID NO:34) bound by the anti-HCV core chimeric antibody (HCV core 201-603-486-333); FIG. 9B: shows the epitope (SEQ ID NO:35) bound by the anti-HCV NS3 chimeric antibody (HCV NS3 CHO 17-903-132sc171); FIG. 9C: shows the epitope (SEQ ID NO:36) bound by the anti-HCV NS4 chimeric antibody (HCV NS4 CHO E99H6C34sc203); and FIG. 9D: shows the epitope (SEQ ID NO:37) bound by the anti-HCV NS5 chimeric antibody (HCV NS5 CHO 48-311-271-455); specific residues bound by the respective chimeric antibodies are underlined and numbered.

FIGS. 11A-D depicts the nucleic acid and amino acid sequences in one embodiment of the present invention of the light and heavy variable regions of an anti-HCV core chimeric antibody (HCV core 14-153-229sc152) with underlining denoting the respective complementarity determining regions (CDRs): FIG. 11A: $V_H$ nucleic acid sequence (SEQ ID NO:40); FIG. 11B: $V_L$ nucleic acid sequence (SEQ ID NO:41); FIG. 11C: $V_H$ amino acid sequence (SEQ ID NO:38); and FIG. 11D: $V_L$ amino acid sequence (SEQ ID NO:39).

DETAILED DESCRIPTION OF THE INVENTION

Figure 1:
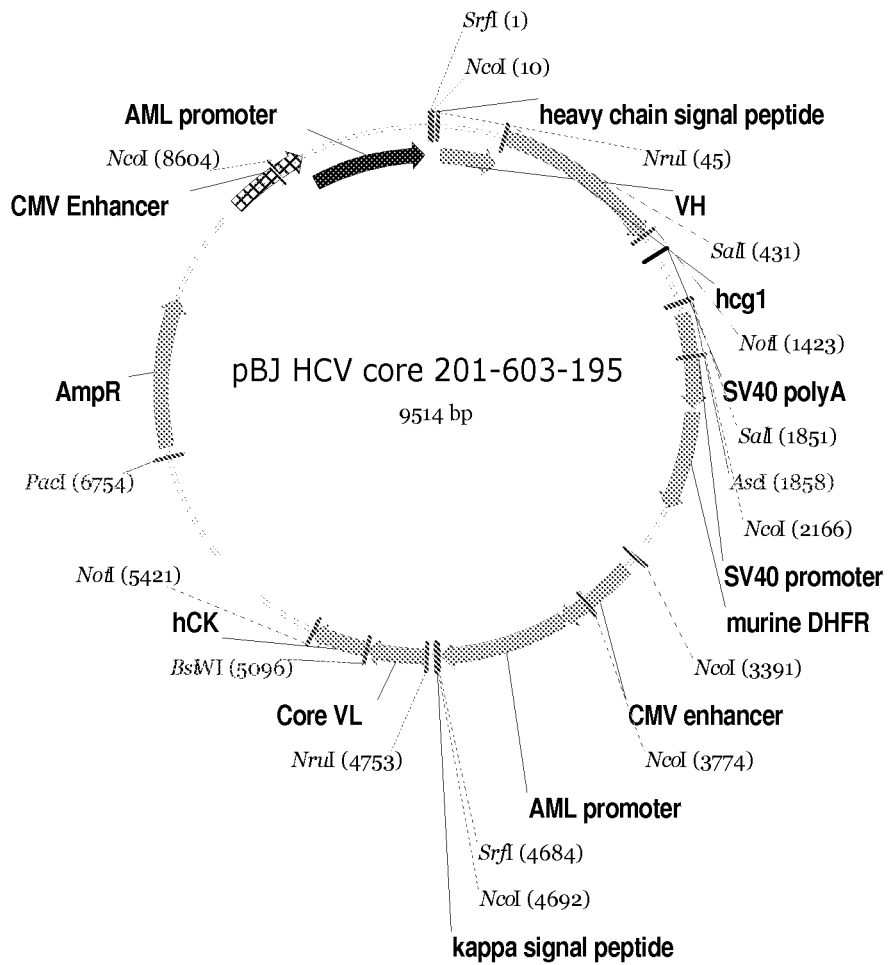
FIG. 1 presents a plasmid map of an expression plasmid used in the preparation of an anti-HCV core chimeric antibody (HCV core 201-603-486-333) in one embodiment of the present invention.

The present invention among other things provides recombinant antibodies, including chimeric antibodies, specific for hepatitis C (HCV) antigenic proteins. In accordance with one embodiment of the present invention, the recombinant antibodies including chimeric antibodies, specifically bind to diagnostically relevant regions of HCV proteins and are thus suitable for use, for example, as diagnostic reagents for the detection of HCV, and/or as standardization reagents or positive control reagents in assays for the detection of HCV.

The present invention also thus provides for an immunodiagnostic reagent comprising one or more recombinant antibodies, including chimeric antibodies, wherein each antibody is capable of specifically binding a diagnostically relevant region of a HCV protein. The recombinant antibodies can be, for example, chimeric antibodies, humanized antibodies, antibody fragments, and the like. In another embodiment, the immunodiagnostic reagent comprises two or more recombinant antibodies, including chimeric antibodies. Optionally the antibodies employed in the immunodiagnostic reagent are each specific for a different HCV antigenic protein, such that the immunodiagnostic reagent is capable of detecting a plurality of HCV antigens. Optionally the immunodiagnostic reagent comprises one or more, or two or more, recombinant antibodies specific for HCV proteins selected from the group consisting of a recombinant antibody specific for HCV core protein, a recombinant antibody specific for HCV E2 protein, a recombinant antibody specific for HCV NS3 protein, a recombinant antibody specific for HCV NS4 protein, and a recombinant antibody specific for HCV NS5 protein.

In one embodiment, the present invention provides for the use of the immunodiagnostic reagent as a standardization reagent in an HCV detection assay, for instance, in place of human sera. In this context, the immunodiagnostic reagent optionally can be employed, for example, to evaluate and standardize the performance of current and future HCV antigen-detection assays.

In an alternative embodiment, the present invention further provides for the use of the recombinant antibodies in the treatment or prevention of a HCV infection.

These and additional embodiments, features, aspects, illustrations, and examples of the invention are further described in the sections which follow. Unless defined otherwise herein, all technical and scientific terms used herein have the same meaning as commonly understood by one of ordinary skill in the art to which this invention belongs.

Definitions

The term "recombinant antibody" or "recombinant antibodies," as used herein, refers to an antibody prepared by one or more steps including cloning nucleic acid sequences encoding all or a part of one or more monoclonal antibodies into an appropriate expression vector by recombinant techniques and subsequently expressing the antibody in an appropriate host cell. The term thus includes, but is not limited to, recombinantly-produced antibodies that are monoclonal antibodies, antibody fragments including fragments of monoclonal antibodies, chimeric antibodies, humanized antibodies (fully or partially humanized), multispecific or multivalent structures formed from antibody fragments, and bifunctional antibodies.

The term "antibody fragment" or "antibody fragments," as used herein, refers to a portion of an intact antibody comprising the antigen binding site or variable region of the intact antibody, wherein the portion is free of the constant heavy chain domains (i.e., $C_H2$, $C_H3$, and $C_H4$, depending on antibody isotype) of the Fc region of the intact antibody. Examples of antibody fragments include, but are not limited to, Fab fragments, Fab' fragments, Fab'-SH fragments, F(ab')$_2$ fragments, Fv fragments, diabodies, single-chain Fv (scFv) molecules, single chain polypeptides containing only one light chain variable domain, single chain polypeptides containing the three CDRs of the light chain variable domain, single chain polypeptides containing only one heavy chain variable region, and single chain polypeptides containing the three CDRs of the heavy chain variable region.

The term "chimeric antibody" (or "cAb") as used herein, refers to a polypeptide comprising all or a part of the heavy and light chain variable regions of an antibody from one host species linked to at least part of the antibody constant regions from another host species.

The term "humanized antibody," as used herein, refers to a polypeptide comprising a modified variable region of a human antibody wherein a portion of the variable region has been substituted by the corresponding sequence from a non-human species and wherein the modified variable region is linked to at least part of the constant region of a human antibody. In one embodiment, the portion of the variable region is all or a part of the complementarity determining regions (CDRs). The term also includes hybrid antibodies produced by splicing a variable region or one or more CDRs of a non-human antibody with a heterologous protein(s), regardless of species of origin, type of protein, immunoglobulin class or subclass designation, so long as the hybrid antibodies exhibit the desired biological activity (i.e. the ability to specifically bind a HCV antigenic protein).

The term "bifunctional antibody," as used herein, refers to an antibody that comprises a first arm having a specificity for one antigenic site and a second arm having a specificity for a different antigenic site, i.e. the bifunctional antibodies have a dual specificity.

The term "diagnostically relevant" as used herein with reference to a region of a HCV protein refers to a region of the protein the detection of which, either alone or in combination with other diagnostically relevant regions of HCV, allows detection of at least three of the six major HCV genotypes (see, for example, Neville et al., ibid.). Examples of diagnostically relevant regions include immunodominant regions known in the art and regions such as those described herein.

As used herein, the term "epitope", "epitopes" or "epitopes of interest" refer to a site(s) on any molecule that is recognized and is capable of binding to a complementary site(s) on its specific binding partner. The molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody. Typically an epitope is contained within a larger antigenic fragment (i.e., region or fragment capable of binding an antibody) and refers to the precise residues known to contact the specific binding partner. It is possible for an antigenic fragment to contain more than one epitope.

As used herein, "specific" or "specificity" in the context of an interaction between members of a specific binding pair (e.g., an antigen and antibody) refers to the selective reactivity of the interaction. The phrase "specifically binds to" and analogous terms thereof refer to the ability of antibodies to specifically bind to a HCV protein and not specifically bind to other entities. Antibodies or antibody fragments that specifically bind to a HCV protein can be identified, for example, by diagnostic immunoassays (e.g., radioimmunoassays ("RIA") and enzyme-linked immunosorbent assays ("ELISAs") (See, for example, Paul, ed., *Fundamental Immunology*, 2nd ed., Raven Press, New York, pages 332-336 (1989)), BIAcore® (Sweden), KinExA® (Kinetic Exclusion Assay, available from Sapidyne Instruments (Boise, Id.)) or other techniques known to those of skill in the art.

As used herein, the term "equilibrium dissociation constant" or "$K_D$" as used interchangeably, refer to the value obtained by dividing the disassociation rate constant ($k_{off}$) by the association rate constant ($k_{on}$). The association rate constant, the disassociation rate constant and the equilibrium dissociation constant are used to represent the binding affinity of an antibody to an antigen. Methods for determining these constants are well known in the art. For example, a Biacore® or KinExA® assay can be used.

As described herein, immunoassays incorporate "quality control reagents" that include but are not limited to, e.g., calibrators, controls, and sensitivity panels. A "calibrator" or "standard" typically is used (e.g., one or more, or a plurality) in order to establish calibration (standard) curves for interpolation of antibody concentration. Optionally, a single calibrator may be used near the positive/negative cutoff Multiple calibrators (i.e., more than one calibrator or a varying amount of calibrator(s)) can be used in conjunction so as to comprise a "sensitivity panel. A "positive control" is used to establish assay performance characteristics and is a useful indicator of the integrity of the reagents (e.g., antigens).

The term "substantially identical," as used herein in relation to a nucleic acid or amino acid sequence indicates that, when optimally aligned, for example using the methods described below, the nucleic acid or amino acid sequence shares at least about 70%, at least about 75%, at least about 80%, at least about 85%, at least about 90%, at least about 95%, at least about 96%, at least about 97%, at least about 98% or at least about 99% sequence identity with a defined second nucleic acid or amino acid sequence (or "reference sequence"). "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two amino acid or nucleic acid sequences can be determined in various ways that are within the skill of a worker in the art, for example, using publicly available computer software such as Smith Waterman Alignment (Smith, T. F. and M. S. Waterman (1981) *J Mol Biol* 147:195-7); "BestFit" (Smith and Waterman, *Advances in Applied Mathematics*, 482-489 (1981)) as incorporated into GeneMatcher Plus™, Schwarz and Dayhof (1979) *Atlas of Protein Sequence and Structure*, Dayhof, M. O., Ed pp 353-358; BLAST program (Basic Local Alignment Search Tool (Altschul, S. F., W. Gish, et al. (1990) *J Mol Biol* 215: 403-10), and variations thereof including BLAST-2, BLAST-P, BLAST-N, BLAST-X, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. In general, for amino acid sequences, the length of comparison sequences will be at least about 10 amino acids. One skilled in the art will understand that the actual length will depend on the overall length of the sequences being compared and may be at least about 20, at least about 30, at least about 40, at least about 50, at least about 60, at least about 70, at least about 80, at least about 90, at least about 100, at least about 110, at least about 120, at least about 130, at least about 140, at least about 150, at least about 200, at least about 250, at least about 300, or at least about 350 amino acids, or it may be the full-length of the amino acid sequence. For nucleic acids, the length of comparison sequences will generally be at least about 25 nucleotides, but may be at least about 50, at least about 100, at least about 125, at least about 150, at least about 200, at least about 250, at least about 300, at least about 350, at least about 400, at least about 450, at least about 500, at least about 550, at least about 600, at least about 650, at least about 700, at least about 800, at least about 900, or at least about 1000 nucleotides, or it may be the full-length of the nucleic acid sequence.

The terms "corresponding to" or "corresponds to" indicate that a nucleic acid sequence is identical to all or a portion of a reference nucleic acid sequence. The term "complementary to" is used herein to indicate that the nucleic acid sequence is identical to all or a portion of the complementary strand of a reference nucleic acid sequence. For illustration, the nucleic acid sequence "TATAC" corresponds to a reference sequence "TATAC" and is complementary to a reference sequence "GTATA."

Unless otherwise specified herein, all nucleic acid sequences are written in a 5' to 3' direction, and all amino acid sequences are written in an amino- to carboxy-terminus direction.

As used herein, the term "about" refers to approximately a +/−10% variation from the stated value. It is to be understood that such a variation is always included in any given value provided herein, whether or not it is specifically referred to.

1. Immunodiagnostic Reagent

The immunodiagnostic reagent of the present invention comprises one or more recombinant antibodies, including recombinant chimeric antibodies, that specifically bind to a diagnostically relevant region of a HCV protein. In one embodiment, therefore, the immunodiagnostic reagent provided by the present invention comprises a single chimeric antibody capable of specifically binding a diagnostically relevant region of a HCV protein. In other embodiments, the immunodiagnostic reagent comprises a plurality of chimeric antibodies, each capable of specifically binding a diagnostically relevant region of a HCV protein (e.g., either the same region, or a different region). One or more of the plurality of chimeric antibodies may be capable of specifically binding a diagnostically relevant region of the same HCV protein. Alternatively, each of the plurality of chimeric antibodies may specifically bind a diagnostically relevant region of a different HCV protein.

In one embodiment of the present invention, the immunodiagnostic reagent is capable of detecting a plurality of HCV antigens and optionally comprises two or more recombinant antibodies, each capable of specifically binding a different HCV antigenic protein. In a further embodiment, the immunodiagnostic reagent optionally comprises three or more recombinant antibodies, each capable of specifically binding a different HCV antigenic protein. In another embodiment, the immunodiagnostic reagent optionally comprises four or more recombinant antibodies, each capable of specifically binding a different HCV antigenic protein.

The recombinant antibodies comprised by the immunodiagnostic reagent can optionally be modified, for example, for detection purposes, for immobilization onto a solid support, to improve stability and/or to improve pharmacokinetic properties, or by other means such as is known in the art.

2. HCV Antigens and Diagnostically Relevant Regions Thereof

HCV contains a plus-strand RNA genome of approximately 10,000 nucleotides that encodes a polyprotein precursor of 3011 amino acids. The polyprotein is co- and post-translationally processed by cellular and viral proteases into the mature structural and nonstructural proteins. The structural proteins include the core protein (amino acids 1 to 192 of the polyprotein) and the envelope glyco-proteins, E1 (from amino acid 193 to 384 of the polyprotein) and E2 (from amino acid 385 to 747 of the polyprotein). The nonstructural (NS) proteins 2-5B include the NS2-3 auto-protease (from amino acid 811 to 1027 of the polyprotein), the NS3 serine protease (from amino acid 1028 to 1658 of the polyprotein), a NTPase/RNA helicase domain in the carboxy terminal two-thirds of NS3, the NS4A polypeptide (from amino acid 1659 to 1712 of the polyprotein), the NS4B and NS5A proteins (from amino acid 1713 to 1973, and amino acid 1974 to 2421 of the polyprotein, respectively), and the NS5B RNA-dependent RNA polymerase (from amino acid 2422 to 3011 of the polyprotein).

Diagnostically relevant regions of many of these proteins have been determined. For core protein, the region defined, for example, by amino acids 1-150, and sub-regions thereof such as amino acids 2 to 120, amino acids 10 to 53, and amino acids 1 to 50, have been determined to be diagnostically relevant. For the NS3 protein, the region defined by, for example, amino acids 1192 to 1457 has been determined to be diagnostically relevant. For the NS4 protein, the regions defined by, for example, amino acids 1920 to 1935 and amino acids 1676 to 1931, and sub-regions thereof such as amino acids 1696-1931 and amino acids 1694 to 1735, have been determined to be diagnostically relevant. For NS5, the region defined by, for example, amino acids 2054 to 2995, and sub-regions thereof such as amino acids 2188 to 2481 and amino acids 2212 to 2313 (see Dou, X-G., et al., *J. Clin. Microbiol.* (2002) 40:61-67), have been determined to be diagnostically relevant. For E1 and E2 the regions defined by amino acids 303-320, and amino acids 405-444, respectively, have been determined to be diagnostically relevant. Other examples include, but are not limited to, the region defined by amino acids 1192 to 1931 (spanning NS3 and NS4), the region defined by amino acids 1569 to 1931 (spanning NS3 and NS4) and the region defined by amino acids 1932 to 2191 (spanning NS4 and NS5).

3. Recombinant Antibodies

The recombinant antibodies of the present invention comprise antigen-binding regions derived from the $V_H$ and/or $V_L$ domains of a native antibody capable of specifically binding to a HCV antigenic protein. The recombinant antibody can be, for example, a recombinantly-produced monoclonal antibody, a fragment of a monoclonal antibody, a chimeric antibody, a humanized antibody, a multispecific or multivalent structure formed from an antibody fragment, or a bifunctional antibody.

In one embodiment, optionally the recombinant antibody is a chimeric antibody that retains the mouse monoclonal antibody specificity and affinity and reacts in an immunoassay format that measures human immunoglobulin. Optionally the mouse-human chimeric antibody is directed against the HCV Core, NS3, NS4, and/or NS5 antigen. Optionally such a chimeric antibody reacts in an existing immunoassay format including but not limited to Abbott Laboratories' HCV assay for EIA (Bead), AxSYM®, ARCHITECT® and PRISM® platforms.

The antigen-binding region comprised by the recombinant antibody can include the entire $V_H$ and/or $V_L$ sequence from the native antibody, or it can comprise one or more portions thereof, such as the CDRs, together with sequences derived from one or more other antibodies. In one embodiment, the recombinant antibody comprises the full-length $V_H$ and $V_L$ sequences of the native antibody.

The native antibody from which the antigen-binding regions are derived is generally a vertebrate antibody. For example, the native antibody can be a rodent (e.g. mouse, hamster, rat) antibody, a chicken antibody, a rabbit antibody, a canine antibody, a feline antibody, a bovine antibody, an equine antibody, a porcine antibody, an ape (e.g. chimpanzee)

antibody, or a human antibody. The source of the antibody is based primarily on convenience. In one embodiment, the native antibody is a non-human antibody.

The recombinant antibody also can include one or more constant regions, for example, the $C_L$, $C_H1$, hinge, $C_H2$, $C_H3$, and/or $C_H4$ regions, derived from the same native antibody or from a different antibody. The constant region(s) can be derived from an antibody from one of a number of vertebrate species, including but not limited to, those listed above. In one embodiment of the present invention, the recombinant antibody comprises at least one constant region. In another embodiment, the recombinant antibody comprises one or more constant regions that are derived from a human antibody. In a specific embodiment of the present invention, the recombinant antibody comprises the variable region of a non-human antibody linked to the constant region of a human antibody.

The constant region(s) comprised by the recombinant antibody can be derived from one or more immunoglobulin classes or isotypes, for example for constant regions derived from human immunoglobulins, the constant region can be derived from one or more of an IgM, IgD, IgG1, IgG2, IgG3, IgG4, IgA1, IgA2 or IgE constant region. When the constant region comprises a region derived from an IgG light chain, this may be derived from a kappa chain or a lambda chain. The recombinant antibody may comprise sequences from more than one class or isotype. Selection of particular constant domains to optimize the desired function of the recombinant antibody is within the ordinary skill in the art. In one embodiment of the present invention, the recombinant antibody comprises one or more constant domains derived from an IgG. In another embodiment, the recombinant antibody comprises regions from both the heavy and light chains of an IgG constant domain.

In one embodiment of the present invention, the antigen-binding regions are derived from a native antibody that specifically binds to an epitope within a diagnostically relevant region of a HCV antigenic protein. Non-limiting examples of diagnostically relevant regions of HCV proteins are provided above. In another embodiment, the antigen-binding regions are derived from a native antibody that specifically binds to an epitope within the region defined by amino acids 1-150 of core protein, the region defined by amino acids 1192 to 1457 of the NS3 protein, the regions defined by amino acids 1920 to 1935 or amino acids 1676 to 1931 of the NS4 protein, or the region defined by amino acids 2054 to 2995 of the NS5 protein. In a further embodiment, the antigen-binding regions are derived from a native antibody that specifically binds to an epitope within the region of the core protein defined by amino acids 1-50 of the HCV polyprotein, within the region of the NS3 protein defined by amino acids 1192-1457 of the HCV polyprotein, within the region of the NS4 protein defined by amino acids 1676-1931 of the HCV polyprotein, or within the region of the NS5 protein defined by amino acids 1932-2191 or amino acids 2188-2481 of the HCV polyprotein. In another embodiment, the antigen-binding regions are derived from a native antibody that specifically binds to a region of the core protein as set forth in SEQ ID NO:33 (GGVYL) or SEQ ID NO:34 (GGQIVGGVYLLPR), a region of the NS3 protein as set forth in SEQ ID NO:35 (AKAVDFVPVESLETTMR-SPVFTDNSSP), a region of the NS4 protein as set forth in SEQ ID NO:36 (PAIIPDREVLYREFDEMEECSQ), or a region of the NS5 protein as set forth in SEQ ID NO:37 (AESYSSMPPLEGEPGDPDLSDGSWSTV).

In a specific embodiment of the present invention, the antigen-binding regions of the recombinant antibody comprise an amino acid sequence substantially identical to all or a portion of the $V_H$ or $V_L$ sequence as set forth in any one of SEQ ID NOs: 1, 2, 9, 10, 17, 18, 25, 26, 38 and 39 (see Table 1). In another embodiment, the antigen-binding regions of the recombinant antibody comprise the complementarity determining regions (CDRs; i.e. CDR1, CDR2 and CDR3) of a $V_H$ or $V_L$ sequence. In a specific embodiment, the antigen-binding regions of the recombinant antibody comprise an amino acid sequence substantially identical to one or more of the CDRs (see Table 1): as set forth in SEQ ID NOs:42, 43 and 44; as set forth in SEQ ID NOs:45, 46 and 47; as set forth in SEQ ID NOs:48, 49 and 50; as set forth in SEQ ID NOs:51, 52 and 53; as set forth in SEQ ID NOs:54, 55 and 56; as set forth in SEQ ID NOs:57, 58 and 59; as set forth in SEQ ID NOs:60, 43 and 61; as set forth in SEQ ID NOs:62, 58 and 63; as set forth in SEQ ID NOs:64, 65 and 66; or as set forth in SEQ ID NOs:67, 46 and 68.

TABLE 1

Exemplary $V_H$ and $V_L$ Sequences

| SEQ ID NO | Sequence | $V_H$ or $V_L$ | HCV Protein Specificity |
|---|---|---|---|
| 1 | QIQLVQSGPELQKPGKTVKISCKTSGYTFTDYP MHWVKQAPGKGLKWMGWINTETGEPTRVDD FKGRFAFSLETSASTAYLQINNLKDEDTATYFC ARGGGVRRQVMDYWGQGTSVTVSS | $V_H$ | Core |
| 2 | DIVMSQSPSSLAVSAGEKVTMSCKSSQSLLNSR TRKNYLVWYQQKPGQSPKLLIYWASTRDSGVP DRFTGSGSGTDFTLTISSVQAEDLAVYYCKQSY NLYTFGGGTKLEIKR | $V_L$ | Core |
| 38 | QIQLVQSGPELKKPGETVKISCKASGYTFTNYG MNWVKQAPGKGLKWMGWINTNTGEPTYAEE FKGRFAFSLETSAITAYLQINNLKNEDTATYFC ARAGGDYYDSSYDYAMDYWGQGTSVTVSS | $V_H$ | Core |
| 39 | DIVLTQSPASLAVSLGQRATISCKASQSVDYDG DSYMNWYQQKPGQPPKLLIYAASNLESGIPAR FSGSGSGTDFTLNIHPVEEEDAATYYCQQSNED PWTFGGGTKLEIKR | $V_L$ | Core |

TABLE 1-continued

Exemplary $V_H$ and $V_L$ Sequences

| SEQ ID NO | Sequence | $V_H$ or $V_L$ | HCV Protein Specificity |
|---|---|---|---|
| 9 | EVKLVESGGGLVQPGGSLKLSCATSGFTFSDYY MYWVRQTPEKRLEWAAYISNGAGSTYYPDTV KGRFTISRDNAKNTLYLQMSRLKSEDTAMYYC ARGLWDGLDYWGQGTTLTVSS | $V_H$ | NS3 |
| 10 | DVVMAQTPLSLPVSLGDQASISCRSSQSLVHSN GNTYLHWYLQRPGQSPKLLIYKVSNRFSGVPD RFSGSGSGTDFTLKISRVEAEDLGVYFCSQSTH VPYTFGGGTKLEIKR | $V_L$ | NS3 |
| 17 | QIQLVQSGPELKKPGETVKISCKASGYTFTDYS MHWVNQAPGKGLKWMGWINTETGEPTYADD FKGRFAFSLETSASTAYLQINNLKNEDTATYFC TRGGTGYWGQGTTLTVSS | $V_H$ | NS4 |
| 18 | DVVMTQTPLSLPVSLGDQASISCRSSQSLVYSN GNTYLHWYLQKPGQSPKLLIYKVSNRFSGVPD RFSGSGSGTDFTLKISRVEAEDLGVYFCSQSTH VPWTFGGGTKLEIKR | $V_L$ | NS4 |
| 25 | EVQLQQSGAELVKPGASVKLSCTASGFNIKDT YMHWVKQRPEQGLEWIGRIDPANGNTKYDPK FQGKATITADTSSNTAYLQLSSLTSEDTAVYYC ARSREFAYWGQGTLVTVSA | $V_H$ | NS5 |
| 26 | DIVMSQSPSSLAVSVGEKVTMSCKSSQSLLYSS NQKNYLAWYQQKPGQSPKLLIYWASTRESGVP DRFTGSGSGTDFTLTISSVKAEDLAVYYCQQYY SYPLTFGAGTKLELKR | $V_L$ | NS5 |
| 42 | GYTFTDYP | CDR1 $V_H$ | Core |
| 43 | INTETGEP | CDR2 $V_H$ | Core |
| 44 | ARGGGVRRQVMDY | CDR3 $V_H$ | Core |
| 45 | QSLLNSRTRKNY | CDR1 $V_L$ | Core |
| 46 | WAS | CDR2 $V_L$ | Core |
| 47 | KQSYNLYT | CDR3 $V_L$ | Core |
| 48 | GYTFTNYG | CDR1 $V_H$ | Core |
| 49 | INTNTGEP | CDR2 $V_H$ | Core |
| 50 | ARAGGDYYDSSYDYAMDY | CDR3 $V_H$ | Core |
| 51 | QSVDYDGDSY | CDR1 $V_L$ | Core |
| 52 | AAS | CDR2 $V_L$ | Core |
| 53 | QQSNEDPWT | CDR3 $V_L$ | Core |
| 54 | GFTFSDYY | CDR1 $V_H$ | NS3 |
| 55 | ISNGAGST | CDR2 $V_H$ | NS3 |
| 56 | ARGLWDGLDY | CDR3 $V_H$ | NS3 |
| 57 | QSLVHSNGNTY | CDR1 $V_L$ | NS3 |
| 58 | KVS | CDR2 $V_L$ | NS3 |
| 59 | SQSTHVPYT | CDR3 $V_L$ | NS3 |
| 60 | GYTFTDYS | CDR1 $V_H$ | NS4 |
| 43 | INTETGEP | CDR2 $V_H$ | NS4 |
| 61 | TRGGTGY | CDR3 $V_H$ | NS4 |
| 62 | QSLVYSNGNTY | CDR1 $V_L$ | NS4 |

TABLE 1-continued

Exemplary V_H and V_L Sequences

| SEQ ID NO | Sequence | V_H or V_L | HCV Protein Specificity |
|---|---|---|---|
| 58 | KVS | CDR2 V_L | NS4 |
| 63 | SQSTHVPWT | CDR3 V_L | NS4 |
| 64 | GFNIKDTY | CDR1 V_H | NS5 |
| 65 | IDPANGNT | CDR2 V_H | NS5 |
| 66 | ARSREFAY | CDR3 V_H | NS5 |
| 67 | QSLLYSSNQKNY | CDR1 V_L | NS5 |
| 46 | WAS | CDR2 V_L | NS5 |
| 68 | QQYYSYPLT | CDR3 V_L | NS5 |

In one embodiment of the present invention, the antigen-binding regions of the recombinant antibody comprise an amino acid sequence substantially identical to all or a portion of the amino acid sequence encoded by any one of SEQ ID NOs:7, 8, 15, 16, 23, 24, 31, 32, 40 or 41 (see Table 2). In another embodiment, the antigen-binding regions of the recombinant antibody comprise a nucleic acid sequence encoding the complementarity determining regions (CDRs; i.e. CDR1, CDR2 and CDR3) of a V_H or V_L sequence. In a specific embodiment, the antigen-binding regions of the recombinant antibody comprise CDRs having an amino acid sequence substantially identical to the amino acid sequences encoded by one or more of SEQ ID NOs:69, 70 and 71; one or more of SEQ ID NOs:72, 73 and 74; one or more of SEQ ID NOs:75, 76 and 77; one or more of SEQ ID NOs:78, 79 and 80; one or more of SEQ ID NOs:81, 82 and 83; one or more of SEQ ID NOs:84, 85 and 86; one or more of SEQ ID NOs:87, 70 and 88; one or more of SEQ ID NOs:89, 85 and 90; one or more of SEQ ID NOs:91, 92 and 93; or one or more of SEQ ID NOs:94, 73 and 95 (see Table 2).

In another specific embodiment of the present invention, the antigen-binding regions of the recombinant antibody comprise an amino acid sequence encoded by a nucleic acid sequence substantially identical to all or a portion of the sequence as set forth in any one of SEQ ID NOs:7, 8, 15, 16, 23, 24, 31, 32, 40 or 41. In a further specific embodiment, the antigen-binding regions of the recombinant antibody comprise CDRs encoded by nucleic acid sequences substantially identical to the sequences as set forth in SEQ ID NOs:69, 70 and 71; as set forth in SEQ ID NOs:72, 73 and 74; as set forth in SEQ ID NOs:75, 76 and 77; as set forth in SEQ ID NOs:78, 79 and 80; as set forth in SEQ ID NOs:81, 82 and 83; as set forth in SEQ ID NOs:84, 85 and 86; as set forth in SEQ ID NOs:87, 70 and 88; as set forth in SEQ ID NOs:89, 85 and 90; as set forth in SEQ ID NOs:91, 92 and 93; or as set forth in SEQ ID NOs:94, 73 and 95.

TABLE 2

Exemplary Nucleic Acid Sequences Encoding V_H and V_L Sequences

| SEQ ID NO | Sequence | Encoding V_H or V_L | HCV Protein Specificity |
|---|---|---|---|
| 7 | CAGATCCAGTTGGTGCAGTCTGGACCTGAGCTGCAG AAGCCTGGAAAGACAGTCAAGATCTCCTGCAAGACT TCTGGTTATACCTTCACAGACTATCCAATGCACTGGG TGAAGCAGGCTCCAGGAAAGGGTTTAAAGTGGATGG GCTGGATAAACACTGAGACTGGTGAGCCAACACGTG TAGATGACTTCAAGGGACGTTTTGCCTTCTCTTTGGA AACCTCTGCCAGCACTGCCTATTTGCAGATCAACAAC CTCAAAGATGAGGACACGGCCACATATTTCTGCGCT AGAGGGGGTGGGGTCCGACGCCAGGTTATGGACTAC TGGGGTCAAGGAACCTCAGTCACCGTCTCCTCA | V_H | Core |
| 8 | GACATTGTGATGTCACAGTCTCCATCCTCCCTGGCTG TGTCAGCAGGAGAGAAGGTCACTATGAGCTGCAAAT CCAGTCAGAGTCTGCTCAATAGTAGAACCCGAAAGA ACTACTTGGTTTGGTACCAGCAGAAACCAGGGCAGT CTCCTAAACTGCTGATCTACTGGGCATCCACTAGGGA TTCTGGGGTCCCTGATCGCTTCACAGGCAGTGGATCT GGGACAGATTTCACTCTCACCATCAGCAGTGTGCAG GCTGAAGACCTGGCAGTTTATTACTGCAAGCAATCTT ATAATCTGTACACGTTCGGAGGGGGGACCAAGCTGG AAATAAAAC | V_L | Core |

TABLE 2-continued

Exemplary Nucleic Acid Sequences Encoding V_H and V_L Sequences

| SEQ ID NO | Sequence | Encoding V_H or V_L | HCV Protein Specificity |
|---|---|---|---|
| 40 | CAGATCCAGTTGGTGCAGTCTGGACCTGAGCTGAAG AAGCCTGGAGAGACAGTCAAGATCTCCTGCAAGGCT TCTGGGTATACCTTCACAAACTATGGAATGAACTGG GTGAAGCAAGCTCCAGGAAAGGGTTTAAAGTGGATG GGCTGGATAAACACCAACACTGGAGAGCCAACATAT GCTGAAGAGTTCAAGGGACGGTTTGCCTTCTCTTTGG AAACCTCTGCCATCACTGCCTATTTGCAGATCAACAA CCTCAAAAATGAGGACACGGCTACATATTTCTGTGC AAGAGCGGGGGAGATTACTACGATAGTAGCTACGA CTATGCTATGGACTACTGGGGTCAAGGAACCTCAGT CACCGTCTCCTCA | V_H | Core |
| 41 | GACATTGTGCTGACCCAATCCCCAGCTTCTTTGGCTG TGTCTCTAGGGCAGAGGGCCACCATCTCCTGCAAGG CCAGCCAAAGTGTTGATTATGATGGTGATAGTTATAT GAACTGGTACCAACAGAAACCAGGACAGCCACCCAA ACTCCTCATCTATGCTGCATCCAATCTAGAATCTGGG ATCCCAGCCAGGTTTAGTGGCAGTGGGTCTGGGACA GACTTCACCCTCAACATCCATCCTGTGGAGGAGGAG GATGCTGCAACCTATTACTGTCAGCAAAGTAATGAG GATCCGTGGACGTTCGGTGGAGGCACCAAGCTGGAA ATCAAACGT | V_L | Core |
| 15 | GAAGTGAAGCTGGTGGAGTCTGGGGGAGGCTTAGTG CAGCCTGGAGGGTCCCTGAAACTCTCCTGTGCAACCT CTGGATTCACTTTCAGTGACTATTATATGTATTGGGT TCGCCAGACTCCAGAGAAGAGGCTGGAGTGGGCCGC ATACATTAGTAATGGTGCTGGTAGCACCTATTATCCA GACACTGTAAAGGGCCGATTCACCATCTCCAGAGAC AATGCCAAGAACACCCTGTACCTGCAAATGAGCCGT CTGAAGTCTGAGGACACAGCCATGTATTACTGTGCA AGAGGCCTCTGGGACGGCCTTGACTACTGGGGCCAA GGCACCACTCTCACAGTCTCCTCG | V_H | NS3 |
| 16 | GATGTTGTGATGGCCCAAACTCCACTCTCCCTGCCTG TCAGTCTTGGAGATCAAGCCTCCATCTCTTGCAGATC TAGTCAGAGCCTTGTACACAGTAATGGAAACACCTA TTTACATTGGTACCTGCAGAGGCCAGGCCAGTCTCCA AAGCTCCTGATCTACAAAGTTTCCAACCGATTTTCTG GGGTCCCAGACAGGTTCAGTGGCAGTGGATCAGGGA CAGATTTCACACTCAAGATCAGCAGAGTGGAGGCTG AGGATCTGGGAGTTTATTTCTGCTCTCAAAGTACACA TGTTCCGTACACGTTCGGAGGGGGGACCAAGCTGGA AATAAAACGT | V_L | NS3 |
| 23 | CAGATCCAGTTGGTGCAGTCTGGACCTGAGCTGAAG AAGCCTGGAGAGACAGTCAAGATCTCCTGCAAGGCT TCTGGTTATACCTTCACAGACTATTCAATGCACTGGG TGAACCAGGCTCCAGGAAAGGGTTTAAAGTGGATGG GCTGGATAAACACTGAGACTGGTGAGCCAACATATG CAGATGACTTCAAGGGACGGTTTGCCTTCTCTTTGGA AACCTCTGCCAGCACTGCCTATTTGCAGATCAACAAC CTCAAAAATGAGGACACGGCTACATATTTCTGTACTA GGGGAGGCACGGGCTACTGGGGCCAAGGCACCACTC TCACAGTCTCCTCA | V_H | NS4 |
| 24 | GATGTTGTGATGACCCAAACTCCACTCTCCCTGCCTG TCAGTCTTGGAGATCAAGCCTCCATCTCTTGCAGATC TAGTCAGAGCCTTGTATACAGTAATGGAAACACCTA TTTACATTGGTACCTGCAGAAGCCAGGCCAGTCTCCA AAGCTCCTGATCTACAAAGTTTCCAACCGATTTTCTG GGGTCCCAGACAGGTTCAGTGGCAGTGGATCAGGGA CAGATTTCACACTCAAGATCAGCAGAGTGGAGGCTG AGGATCTGGGAGTTTATTTCTGCTCTCAAAGTACACA TGTTCCGTGGACGTTCGGTGGAGGCACCAAGCTGGA AATCAAACGG | V_L | NS4 |
| 31 | GAGGTTCAGCTGCAGCAGTCTGGGGCAGAGCTTGTG AAGCCAGGGGCCTCAGTCAAGTTGTCCTGCACAGCT TCTGGCTTCAACATTAAAGACACCTATATGCACTGGG TGAAGCAGAGGCCTGAACAGGGCCTGGAGTGGATTG GAAGGATTGATCCTGCGAATGGTAATACTAAATATG ACCCGAAGTTCCAGGGCAAGGCCACTATAACAGCAG ACACATCCTCCAACACAGCCTACCTGCAGCTCAGCA | V_H | NS5 |

TABLE 2-continued

Exemplary Nucleic Acid Sequences Encoding $V_H$ and $V_L$ Sequences

| SEQ ID NO | Sequence | Encoding $V_H$ or $V_L$ | HCV Protein Specificity |
|---|---|---|---|
| | GCCTGACATCTGAGGACACTGCCGTCTATTACTGTGC TAGATCGCGGGAGTTTGCTTACTGGGGCCAAGGGAC TCTGGTCACTGTCTCTGCA | | |
| 32 | GACATTGTGATGTCACAGTCTCCATCCTCCCTAGCTG TGTCAGTTGGAGAGAAGGTTACTATGAGCTGCAAGT CCAGTCAGAGCCTTTTATATAGTAGCAATCAAAAGA ACTACTTGGCCTGGTACCAGCAGAAACCAGGGCAGT CTCCTAAACTGCTGATTTACTGGGCATCCACTAGGGA ATCTGGGGTCCCTGATCGCTTCACAGGCAGTGGATCT GGGACAGATTTCACTCTCACCATCAGCAGTGTGAAG GCTGAAGACCTGGCAGTTTATTACTGTCAGCAATATT ATAGCTATCCGCTCACGTTCGGTGCTGGGACCAAGCT GGAGCTGAAACGG | $V_L$ | NS5 |
| 69 | GGTTATACCTTCACAGACTATCCA | CDR1 $V_H$ | Core |
| 70 | ATAAACACTGAGACTGGTGAGCCA | CDR2 $V_H$ | Core |
| 71 | GCTAGAGGGGTGGGGTCCGACGCCAGGTTATGGAC TAC | CDR3 $V_H$ | Core |
| 72 | CAGAGTCTGCTCAATAGTAGAACCCGAAAGAACTAC | CDR1 $V_L$ | Core |
| 73 | TGGGCATCC | CDR2 $V_L$ | Core |
| 74 | AAGCAATCTTATAATCTGTACACG | CDR3 $V_L$ | Core |
| 75 | GGGTATACCTTCACAAACTATGGA | CDR1 $V_H$ | Core |
| 76 | ATAAACACCAACACTGGAGAGCCA | CDR2 $V_H$ | Core |
| 77 | GCAAGAGCGGGGGAGATTACTACGATAGTAGCTAC GACTATGCTATGGACTAC | CDR3 $V_H$ | Core |
| 78 | CAAAGTGTTGATTATGATGGTGATAGTTAT | CDR1 $V_L$ | Core |
| 79 | GCTGCATCC | CDR2 $V_L$ | Core |
| 80 | CAGCAAAGTAATGAGGATCCGTGGACG | CDR3 $V_L$ | Core |
| 81 | GGATTCACTTTCAGTGACTATTAT | CDR1 $V_H$ | NS3 |
| 82 | ATTAGTAATGGTGCTGGTAGCACC | CDR2 $V_H$ | NS3 |
| 83 | GCAAGAGGCCTCTGGGACGGCCTTGACTAC | CDR3 $V_H$ | NS3 |
| 84 | CAGAGCCTTGTACACAGTAATGGAAACACCTAT | CDR1 $V_L$ | NS3 |
| 85 | AAAGTTTCC | CDR2 $V_L$ | NS3 |
| 86 | TCTCAAAGTACACATGTTCCGTACACG | CDR3 $V_L$ | NS3 |
| 87 | GGTTATACCTTCACAGACTATTCA | CDR1 $V_H$ | NS4 |
| 70 | ATAAACACTGAGACTGGTGAGCCA | CDR2 $V_H$ | NS4 |
| 88 | ACTAGGGGAGGCACGGGCTAC | CDR3 $V_H$ | NS4 |
| 89 | CAGAGCCTTGTATACAGTAATGGAAACACCTAT | CDR1 $V_L$ | NS4 |
| 85 | AAAGTTTCC | CDR2 $V_L$ | NS4 |
| 90 | TCTCAAAGTACACATGTTCCGTGGACG | CDR3 $V_L$ | NS4 |
| 91 | GGCTTCAACATTAAAGACACCTAT | CDR1 $V_H$ | NS5 |
| 92 | ATTGATCCTGCGAATGGTAATACT | CDR2 $V_H$ | NS5 |
| 93 | GCTAGATCGCGGGAGTTTGCTTAC | CDR3 $V_H$ | NS5 |

TABLE 2-continued

Exemplary Nucleic Acid Sequences Encoding $V_H$ and $V_L$ Sequences

| SEQ ID NO | Sequence | Encoding $V_H$ or $V_L$ | HCV Protein Specificity |
|---|---|---|---|
| 94 | CAGAGCCTTTTATATAGTAGCAATCAAAAGAACTAC | CDR1 $V_L$ | NS5 |
| 73 | TGGGCATCC | CDR2 $V_L$ | NS5 |
| 95 | CAGCAATATTATAGCTATCCGCTCACG | CDR3 $V_L$ | NS5 |

The amino acid sequence of recombinant antibody need not correspond precisely to the parental sequences, i.e. it may be a "variant sequence." For example, depending in the domains comprised by the recombinant antibody, one or more of the $V_L$, $V_H$, $C_L$, $C_H1$, hinge, $C_H2$, $C_H3$, and $C_H4$, as applicable, may be mutagenized by substitution, insertion or deletion of one or more amino acid residues so that the residue at that site does not correspond to either the parental (or reference) sequence. One skilled in the art will appreciate, however, that such mutations will not be extensive and will not dramatically affect binding of the recombinant antibody to its target HCV protein. In accordance with the present invention, when a recombinant antibody comprises a variant sequence, the variant sequence is at least about 70% identical to the reference sequence. In one embodiment, the variant sequence is at least about 75% identical to the reference sequence. In other embodiments, the variant sequence is at least about 80%, at least about 85% or at least about 90% identical to the reference sequence. In a specific embodiment, the reference sequence corresponds to a sequence as set forth in any one of SEQ ID NOs: 1, 2, 9, 10, 17, 18, 25, 26, 38 and 39. In another embodiment, the reference sequence corresponds to a sequence as set forth in any one of SEQ ID NOs: 42, 43, 44, 45, 46, 47, 48, 49, 50, 51, 52, 53, 54, 55, 56, 57, 58, 59, 60, 61, 62, 63, 64, 65, 66, 67 and 68.

Generally, when the recombinant antibody comprises a variant sequence that contains one or more amino acid substitutions, they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group.

Thus, the present invention in other embodiments further provides isolated polypeptides corresponding to novel recombinant antibody sequences disclosed herein. Optionally the isolated polypeptide comprises a portion of a recombinant (e.g., chimeric) antibody that specifically binds to a diagnostically relevant region of a HCV protein selected from the group consisting of HCV core protein, HCV NS3 protein, HCV NS4 protein, and HCV NS5 protein. In one embodiment the polypeptide comprises a $V_H$ region selected from the group consisting of a $V_H$ region comprising an amino acid sequence substantially identical to the sequence as set forth in any one or more of SEQ ID NOs:1, 9, 17, 25, and 38. In another embodiment the polypeptide comprises a $V_H$ region comprising complementarity determining region sequences that are substantially identical to: one or more of the sequences set forth in SEQ ID NOs: 42, 43 and 44; one or more of the sequences set forth in SEQ ID NOs:48, 49 and 50; one or more of the sequences set forth in SEQ ID NOs: 54, 55 and 56; one or more of the sequences set forth in SEQ ID NOs: 60, 43 and 61; and/or to one or more of the sequences set forth in SEQ ID NOs:64, 65 and 66. In another embodiment the polypeptide comprises a $V_L$ region comprising an amino acid sequence that is substantially identical to the sequence as set forth in any one or more of SEQ ID NOS:2, 10, 18, 26, and 39. In still another embodiment the polypeptide comprises a $V_L$ region comprising complementarity determining region sequences that are substantially identical to: one or more of the sequences set forth in SEQ ID NOs: 45, 46 and 47; one or more of the sequences set forth in SEQ ID NOs: 51, 52 and 53; one or more of the sequences set forth in SEQ ID NOs: 57, 58 and 59; one or more of the sequences set forth in SEQ ID NOs: 62, 58 and 63; and/or one or more of the sequences set forth in SEQ ID NOs: 67, 46 and 68.

In still another embodiment, the polypeptide comprises a $V_H$ region selected from the group consisting of a $V_H$ region comprising an amino acid sequence substantially identical to the sequence encoded by any one or more of SEQ ID NOs: 7, 15, 23, 31, and 40. In yet another embodiment, the polypeptide comprises a $V_H$ region comprising complementarity determining region sequences that are substantially identical to: one or more of the sequences encoded by SEQ ID NOs: 69, 70 and 71; one or more of the sequences encoded by SEQ ID NOs:75, 76 and 77; one or more of the sequences encoded by SEQ ID NOs: 81, 82 and 83; one or more of the sequences encoded by SEQ ID NOs: 87, 70 and 88; one or more of the sequences encoded by SEQ ID NOs: 91, 92 and 93. In another embodiment, the polypeptide comprises a $V_L$ region selected from the group consisting of a $V_L$ region comprising an amino acid sequence substantially identical to the sequence encoded by any one or more of SEQ ID NOs:8, 16, 24, 32 and 41. In still yet another embodiment, the polypeptide comprises a $V_L$ region comprising complementarity determining region sequences substantially identical to one or more of: the sequences encoded by SEQ ID NOs: 89, 85 and 90; the sequences encoded by SEQ ID NOs: 84, 85 and 86; the sequences encoded by SEQ ID NOs: 72, 73 and 74; and/or the sequences encoded by SEQ ID NOs: 78, 79 and 80; and/or one or more of the sequences encoded by SEQ ID NOs: 94, 73 and 95.

Likewise, the nucleic acid sequence encoding the variable region(s) need not correspond precisely to the parental reference sequence but may vary by virtue of the degeneracy of the genetic code and/or such that it encodes a variant amino acid sequence as described above. In one embodiment of the present invention, therefore, the nucleic acid sequence encoding a variable region of the recombinant antibody is at least about 70% identical to the reference sequence. In another embodiment, the nucleic acid sequence encoding a variable region of the recombinant antibody is at least about 75% identical to the reference sequence. In other embodiments, the nucleic acid sequence encoding a variable region of the recombinant antibody is at least about 80%, at least about 85% or at least about 90% identical to the reference sequence. In a specific embodiment, the reference sequence corresponds to a sequence as set forth in any one of SEQ ID NOs:7, 8, 15, 16, 23, 24, 31, 32, 40 or 41. In another embodiment, the reference sequence corresponds to a sequence as set forth in any one of SEQ ID NOs: 69, 70, 71, 72, 73, 74, 75, 76, 77, 78, 79, 80, 81, 82, 83, 84, 85, 86, 87, 88, 89, 90, 91, 92, 93, 94 and 95.

Thus, the present invention in other embodiments further provides isolated polynucleotides which encode novel recombinant antibody sequences (including chimerical antibody sequences) disclosed herein. Optionally the isolated polynucleotide encodes a portion of a recombinant (e.g., chimeric) antibody that specifically binds to a diagnostically relevant region of a HCV protein selected from the group consisting of HCV core protein, HCV NS3 protein, HCV NS4 protein, and HCV NS5 protein. In one embodiment the polynucleotide encodes a $V_H$ region selected from the group consisting of a $V_H$ region comprising an amino acid sequence substantially identical to the sequence as set forth in any one or more of SEQ ID NOs:1, 7, 9, 17, 25, and 38. In another embodiment the polynucleotide encodes a $V_H$ region comprising complementarity determining region sequences that are substantially identical to: one or more of the sequences set forth in SEQ ID NOs: 42, 43 and 44; one or more of the sequences set forth in SEQ ID NOs:48, 49 and 50; one or more of the sequences set forth in SEQ ID NOs: 54, 55 and 56; one or more of the sequences set forth in SEQ ID NOs: 60, 43 and 61; and/or to one or more of the sequences set forth in SEQ ID NOs:64, 65 and 66. In another embodiment the polynucleotide encodes a $V_L$ region comprising an amino acid sequence that is substantially identical to the sequence as set forth in any one or more of SEQ ID NOS:2, 10, 18, 26, and 39. In still another embodiment the polynucleotide encodes a $V_L$ region comprising complementarity determining region sequences that are substantially identical to: one or more of the sequences set forth in SEQ ID NOs: 45, 46 and 47; one or more of the sequences set forth in SEQ ID NOs: 51, 52 and 53; one or more of the sequences set forth in SEQ ID NOs: 57, 58 and 59; one or more of the sequences set forth in SEQ ID NOs: 62, 58 and 63; and/or one or more of the sequences set forth in SEQ ID NOs: 67, 46 and 68.

In still another embodiment, the polynucleotide encodes a $V_H$ region selected from the group consisting of a $V_H$ region comprising an amino acid sequence substantially identical to the sequence encoded by any one or more of SEQ ID NOs: 7, 15, 23, 31 and 40. In yet another embodiment, the polynucleotide encodes a $V_H$ region comprising complementarity determining region sequences that are substantially identical to: one or more of the sequences encoded by SEQ ID NOs: 69, 70 and 71; one or more of the sequences encoded by SEQ ID NOs:75, 76 and 77; one or more of the sequences encoded by SEQ ID NOs: 81, 82 and 83; one or more of the sequences encoded by SEQ ID NOs: 87, 70 and 88; one or more of the sequences encoded by SEQ ID NOs: 91, 92 and 93. In another embodiment, the polynucleotide encodes a $V_L$ region selected from the group consisting of a $V_L$ region comprising an amino acid sequence substantially identical to the sequence encoded by any one or more of SEQ ID NOs:8, 16, 24, 32 and 41. In still yet another embodiment, the polynucleotide encodes a $V_L$ region comprising complementarity determining region sequences substantially identical to one or more of: the sequences encoded by SEQ ID NOs: 89, 85 and 90; the sequences encoded by SEQ ID NOs: 84, 85 and 86; the sequences encoded by SEQ ID NOs: 72, 73 and 74; and/or the sequences encoded by SEQ ID NOs: 78, 79 and 80; and/or one or more of the sequences encoded by SEQ ID NOs: 94, 73 and 95.

In one embodiment, the antibodies can be further modified to reduce the immunogenicity to a human relative to the native antibody by mutating one or more amino acids in the non-human portion of the antibody that are potential epitopes for human T-cells in order to eliminate or reduce the immunogenicity of the antibody when exposed to the human immune system. Suitable mutations include, for example, substitutions, deletions and insertions of one or more amino acids.

In one embodiment, the recombinant antibodies of the present invention can be further modified for immobilization onto a suitable solid phase. Immobilization can be achieved through covalent or non-covalent (for example, ionic, hydrophobic, or the like) attachment to the solid phase. Suitable modifications are known in the art and include the addition of a functional group or chemical moiety to either the C-terminus or the N-terminus of one of the amino acid sequences comprised by the recombinant antibody to facilitate crosslinking or attachment of the recombinant antibody to the solid support. Exemplary modifications include the addition of functional groups such as S-acetylmercaptosuccinic anhydride (SAMSA) or S-acetyl thioacetate (SATA), or addition of one or more cysteine residues to the N- or C-terminus of the amino acid sequence. Other cross-linking reagents are known in the art and many are commercially available (see, for example, catalogues from Pierce Chemical Co. and Sigma-Aldrich). Examples include, but are not limited to, diamines, such as 1,6-diaminohexane; dialdehydes, such as glutaraldehyde; bis-N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; 3-maleimidopropionic acid N-hydroxysuccinimide ester, and the like.

Other modifications include the addition of one or more amino acids at the N- or C-terminus, such as histidine residues to allow binding to $Ni^{2+}$ derivatized surfaces, or cysteine residues to allow disulfide bridge formation or binding to Sulfolink™ agarose. Alternatively, the antibody may be modified to include one or more chemical spacers at the N-terminus or C-terminus in order to distance the recombinant antibody optimally from the solid support. Spacers that can be used include but are not limited to 6-aminohexanoic acid; 1,3-diamino propane; 1,3-diamino ethane; and short amino acid sequences, such as polyglycine sequences, of 1 to 5 amino acids.

In an alternative embodiment, the recombinant antibodies optionally can be conjugated to a carrier protein, such as bovine serum albumin (BSA), casein, or thyroglobulin, in order to immobilize them onto a solid phase.

In another embodiment, the present invention provides for modification of the recombinant antibodies to incorporate a detectable label. Detectable labels according to the invention preferably are molecules or moieties which can be detected directly or indirectly and are chosen such that conjugation of the detectable label to the recombinant antibody preferably does not interfere with the specific binding of the antibody to its target HCV protein. Methods of labeling antibodies are well-known in the art and include, for example, the use of bifunctional cross-linkers, such as SAMSA (S-acetylmercaptosuccinic anhydride), to link the recombinant antibody to the detectable label. Other cross-linking reagents such as are known in the art or which similar to those described above likewise can be employed.

Detectable labels for use with the recombinant antibodies of the present invention include, for example, those that can be directly detected such as radioisotopes, fluorophores, chemiluminophores, enzymes, colloidal particles, fluorescent microparticles, and the like. The detectable label is either itself detectable or may be reacted with one or more additional compounds to generate a detectable product. Thus, one skilled in the art will understand that directly detectable labels of the invention may require additional components, such as substrates, triggering reagents, light, and the like to enable detection of the label. Examples of detectable labels include, but are not limited to, chromogens, radioisotopes such as, e.g., $^{125}I$, $^{131}I$, $^{32}P$, $^{3}H$, $^{35}S$ and $^{14}C$), fluorescent compounds (such as fluorescein, rhodamine, ruthenium tris bipyridyl and lanthanide chelate derivatives), chemiluminescent compounds (such as, e.g., acridinium and luminol), visible or fluorescent particles, nucleic acids, complexing agents, or catalysts such as enzymes (such as, e.g., alkaline phosphatase, acid phosphatase, horseradish peroxidase, β-galactosidase, β-lactamase, luciferase). In the case of enzyme use, addition of, for example, a chromo-, fluoro-, or lumogenic substrate preferably results in generation of a detectable signal. Other detection systems such as time-resolved fluorescence, internal-reflection fluorescence, and Raman spectroscopy are optionally also useful.

The present invention also provides for the use of labels that are detected indirectly. Indirectly detectable labels typically involve the use of an "affinity pair" i.e. two different molecules, where a first member of the pair is coupled to the recombinant antibody of the present invention, and the second member of the pair specifically binds to the first member. Binding between the two members of the pair is typically chemical or physical in nature. Examples of such binding pairs include, but are not limited to: antigens and antibodies; avidin/streptavidin and biotin; haptens and antibodies specific for haptens; complementary nucleotide sequences; enzyme cofactors/substrates and enzymes; and the like.

4. Preparation of Recombinant Antibodies

The recombinant antibodies of the present invention can comprise antigen-binding domain sequences (for example, the $V_H$ and/or $V_L$ sequences, or a portion thereof) derived from, for example, a monoclonal antibody produced by a human or non-human animal, such as a rodent, rabbit, canine, feline, bovine, equine, porcine, ape or chicken. Alternatively, antigen-binding domains with the desired binding activity can be selected through the use of combinatorial libraries expressed in lambda phage, on the surface of bacteriophage, bacteria or yeast, or screened by display on other biological (for example, retrovirus or polysome) or non-biological systems using standard techniques (see, for example, Marks, J. D. et. al., *J. Mol. Biol.* 222:581-597 (1991); Barbas, C. F. III et. al., *Proc. Natl. Acad. Sci. USA* 89:4457-4461 (1992)). The libraries can be composed of native antigen-binding domains isolated from an immunized or unimmunized host, synthetic or semi-synthetic antigen-binding domains, or modified antigen-binding domains.

In one embodiment of the present invention, the recombinant antibodies comprise antigen-binding domains derived from monoclonal antibodies that bind to the HCV protein of interest. Methods of raising monoclonal antibodies against a desired antigen are well known in the art. For example, monoclonal antibodies can be made using the hybridoma method first described by Kohler et al., *Nature,* 256:495 (1975). In general in the hybridoma method, a mouse or other appropriate host animal, such as a hamster or macaque monkey, is immunized by multiple subcutaneous or intraperitoneal injections of antigen and a carrier and/or adjuvant at multiple sites. Two weeks later, the animals are boosted, and about 7 to 14 days later animals are bled and the serum is assayed for anti-antigen titer. Animals can be boosted until titer plateaus.

The splenocytes of the mice are extracted and fused with myeloma cells using a suitable fusing agent, such as polyethylene glycol, to form a hybridoma cell (see, for example, Goding, *Monoclonal Antibodies: Principles and Practice,* pp. 59-103 (Academic Press, 1986); Galfre et al., *Nature,* 266:550 (1977)). Suitable myeloma cell lines are known in the art and include, but are not limited to, murine myeloma lines, such as those derived from MOP-21 and MC-11 mouse tumors (available from the Salk Institute Cell Distribution Center, San Diego, Calif.), as well as SP-2, SP2/0 and X63-Ag8-653 cells (available from the American Type Culture Collection (ATCC), Manassas, Va.). Human myeloma and mouse-human heteromyeloma cell lines also have been described for the production of human monoclonal antibodies (see, for example, Kozbor, *J. Immunol.,* 133:3001 (1984); Brodeur et al., *Monoclonal Antibody Production Techniques and Applications,* pp. 51-63 (Marcel Dekker, Inc., New York, 1987)). The hybridoma cells thus prepared can be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridoma cells obtained through such a selection are then assayed to identify clones which secrete antibodies capable of binding the HCV antigen used in the initial immunization, for example, by immunoprecipitation or by an in vitro binding assay, such as radioimmunoassay (RIA) or enzyme-immunoassay (EIA or ELISA). The binding affinity of the monoclonal antibody can optionally be determined, for example, by the Scatchard analysis of Munson et al., *Anal. Biochem.,* 107:220 (1980).

After hybridoma cells are identified that produce antibodies of the desired specificity, the clones may be subcloned by limiting dilution procedures, for example the procedure described by Wands et al. (*Gastroenterology* 80:225-232 (1981)), and grown by standard methods (see, for example, Goding, ibid.). Suitable culture media for this purpose include, for example, D-MEM, IMDM or RPMI-1640 medium. Alternatively, the hybridoma cells may be grown in vivo as ascites tumors in an animal.

The monoclonal antibodies secreted by the subclones optionally can be isolated from the culture medium, ascites fluid, or serum by conventional immunoglobulin purification procedures such as, for example, protein A chromatography, hydroxylapatite chromatography, gel electrophoresis, dialysis, or affinity chromatography.

In one embodiment of the present invention, the recombinant antibodies are derived from monoclonal antibodies raised to a HCV antigen derived from a diagnostically relevant region of an HCV protein. In another embodiment, the recombinant antibodies are derived from monoclonal antibodies raised to a HCV antigen derived from a diagnostically relevant region of HCV core, E2, NS3, NS4 or NS5 protein. In a further embodiment, the recombinant antibodies are derived from monoclonal antibodies raised to a HCV antigen comprising all or a fragment of: (a) the region of the core protein defined by amino acids 1-150 of the HCV polyprotein, (b) the region of the NS3 protein defined by amino acids 1192 to 1457 of the HCV polyprotein, (c) the regions of the NS4 protein defined by amino acids 1920 to 1935 or amino acids 1676 to 1931 of the HCV polyprotein, or (d) the region of the NS5 protein defined by amino acids 2054 to 2995 of the HCV polyprotein. In another embodiment, the recombinant antibodies are derived from monoclonal antibodies raised to a HCV antigen comprising all or a fragment (for example, a fragment comprising one or more epitopes) of: (a) the region of the core protein defined by amino acids 1-50 of the HCV polyprotein, (b) the region of the NS3 protein defined by amino acids 1192-1457 of the HCV polyprotein, (c) the region of the NS4 protein defined by amino acids 1696-1931 of the HCV polyprotein, and/or (d) the region of the NS5 protein defined by amino acids 1932 to 2191 or amino acids 2188 to 2481. In a further embodiment, the recombinant antibodies are derived from monoclonal antibodies raised to a HCV antigen comprising a sequence substantially identical to the sequence as set forth in any one of SEQ ID NOs:33, 34, 35, 36, or 37.

In still a further embodiment, the recombinant antibody is derived from monoclonal antibodies raised to an epitope from the HCV core protein selected from the group consisting of: (a) an epitope comprised by the amino acid sequence as set forth in SEQ ID NO:100; (b) an epitope comprised by the amino acid sequence as set forth in SEQ ID NO:101; and (c) an epitope comprised by the amino acid sequence as set forth in SEQ ID NO:102. In yet another embodiment, the recombinant antibody is derived from monoclonal antibodies raised to an epitope from the HCV NS3 protein selected from the group consisting of: (a) an epitope comprised by the amino acid sequence as set forth in SEQ ID NO:103; (b) an epitope comprised by the amino acid sequence as set forth in SEQ ID NO:104; and (c) an epitope comprised by the amino acid sequence as set forth in SEQ ID NO:105. In still yet another embodiment, the recombinant antibody is derived from monoclonal antibodies raised to an epitope from the HCV NS4 protein selected from the group consisting of: (a) an epitope comprised by the amino acid sequence as set forth in SEQ ID NO:106; (b) an epitope comprised by the amino acid sequence as set forth in SEQ ID NO:107; and (c) an epitope comprised by the amino acid sequence as set forth in SEQ ID NO:108. And in another embodiment, the recombinant antibody is derived from monoclonal antibodies raised to an epitope from the HCV NS5 protein selected from the group consisting of: (a) an epitope comprised by the amino acid sequence as set forth in SEQ ID NO:109; (b) an epitope comprised by the amino acid sequence as set forth in SEQ ID NO:110; and (c) an epitope comprised by the amino acid sequence as set forth in SEQ ID NO:111.

Optionally the monoclonal antibody is expressed by a cell line selected from the group consisting of anti-HCV Core 201-603-195, anti-HCV Core 14-153-462, anti-HCV NS3 17-903-127, anti-HCV NS4 E99H6C34, and anti-HCV NS5 48-311-387.

Once a monoclonal antibody has been prepared, DNA encoding the monoclonal antibody or the variable regions thereof can readily be isolated by standard techniques, for example by using oligonucleotide probes that are capable of binding specifically to genes encoding the heavy and light chains or the variable regions of the monoclonal antibody, or by RT-PCR of the mRNA encoding the monoclonal antibody using primers to conserved regions (for example, the IgG primer sets available from Novagen (EMD Biosciences, Inc.), San Diego, Calif.).

Once isolated, the DNA can be, for example, cloned into an appropriate expression vector and introduced into a suitable host cell, such as $E.$ $coli$ cells, yeast cells, simian COS cells, Chinese hamster ovary (CHO) cells, human embryonic kidney (HEK) cells (for example, HEK 293), or myeloma cells that do not otherwise produce immunoglobulin protein, in order to produce recombinant monoclonal antibodies. Optionally, in one embodiment, the anti-HCV mouse-human chimeric antibodies of the invention are produced in a Chinese hamster Ovary (CHO) cell line, which is advantageous in that they can be produced in quantities sufficient for commercial use.

Alternatively, the DNA encoding the monoclonal antibody or the variable regions thereof can be used to produce chimeric antibodies, humanized antibodies and antibody fragments by standard methods known in the art.

For example, chimeric monoclonal antibodies can be produced by cloning the DNA encoding the variable regions of the monoclonal antibody into mammalian expression vector(s) containing antibody heavy and light chain constant region genes derived from a different host species. Many eukaryotic antibody expression vectors that are either stably integrated or exist as extrachromosomal elements have been described and are known to those of ordinary skill in the art. In general, antibody expression vectors are plasmids comprising the gene encoding the heavy chain constant region and/or the gene encoding the light chain constant region, an upstream enhancer element and a suitable promoter. For example, for human constant regions, the vector can comprise the human IgG1 (human Cγ1) and human kappa constant region (human Cκ) genes and the immunoglobulin H chain enhancer element. The vector can also contain a bacterial origin of replication and selection marker. Optional inclusion of a selection marker, as is known in the art, allows for selection and amplification under defined growth conditions, for example the dihydrofolate reductase (DHFR) gene provides for selection and amplification in mammalian cells with methotrexate. Construction of an appropriate for antibody expression starting from a commercial mammalian expression vector, can be readily achieved by the skilled technician. Representative examples of recombinant antibody expression vectors are provided in FIGS. 1, 3, 5, 7 and 12.

Introduction of the expression construct(s) into appropriate host cells results in production of complete chimeric antibodies of a defined specificity (see, for example, Morrison, S. L. et al., *Proc. Natl. Acad. Sci. USA* 81: 6851-6855 (1984)). The heavy and light chain coding sequences can be introduced into the host cell individually on separate plasmids or together on the same vector.

Depending on the vector system utilized, many different immortalized cell lines may serve as suitable hosts, these include but are not limited to myeloma (for example, X63-Ag8.653), hybridoma (for example, Sp2/0-Ag14), lymphoma, insect cells (for example sf9 cells), human embryonic kidney cells (for example, HEK 293) and Chinese Hamster Ovary (CHO) cells. The expression constructs can be introduced into the host cells using a variety of techniques known in the art, including but not limited to, calcium phosphate precipitation, protoplast fusion, lipofection, retrovirus-derived shuttle vectors, and electroporation.

Chimeric antibodies and antibody fragments can also be produced in other expression systems including, but not limited to, baculovirus, yeast, bacteria (such as $E.$ $coli$), and in vitro in cell-free systems such as rabbit reticulocyte lysate.

The recombinant antibody can be isolated from the host cells by standard immunoglobulin purification procedures such as, for example, cross-flow filtration, ammonium sulphate precipitation, protein A chromatography, hydroxylapatite chromatography, gel electrophoresis, dialysis, affinity chromatography, or combinations thereof.

Alternatively, antibody fragments can be generated from a purified antibody preparation by conventional enzymatic methods, for example, F(ab')$_2$ fragments can be produced by pepsin cleavage of the intact antibody, and Fab fragments can be produced by briefly digesting the intact antibody with papain.

Recombinant bispecific and heteroconjugate antibody fragments having specificities for at least two different antigens can be prepared as full length antibodies or as antibody fragments (such as F(ab')$_2$ bispecific antibody fragments). Antibody fragments having more than two valencies (for example, trivalent or higher valency antibody fragments) also are contemplated. Bispecific antibodies, heteroconjugate antibodies, and multi-valent antibodies can be prepared by standard methods known to those skilled in the art.

5. Testing of Recombinant Antibodies

The ability of the recombinant antibody to specifically bind to the target HCV antigen can be assessed by standard immunological techniques (see, for example, *Current Protocols in Immunology*, Coligan, J. E., et al. (ed.), J. Wiley & Sons, New York, N.Y.). For example, by radioimmunoassay (RIA) or enzyme immunoassay (EIA or ELISA). In one embodiment of the present invention, the recombinant antibody demonstrates substantially the same specificity as the monoclonal antibody from which the antigen-binding domains are derived.

The recombinant antibodies optionally can also be tested for their binding affinity to the target HCV antigen by measuring the equilibrium dissociation constant ($K_D$) by standard techniques. In one embodiment of the present invention, the recombinant antibodies (e.g., chimeric antibodies) have a $K_D$ less than about 1 µM. In another embodiment, the recombinant antibodies (e.g., chimeric antibodies) have a $K_D$ less than about 100 nM. In yet another embodiment, optionally the recombinant antibody is chimeric antibody that specifically binds to a HCV protein epitope, wherein said chimeric antibody is selected from the group consisting of:

(a) a HCV core chimeric antibody having an equilibrium dissociation constant ($K_D$) of from about 0.1 nM to about 1.0 nM, optionally of about 0.4 nM, about 0.5, nM, about 0.6 nM, about 0.7 nM, or about 0.8 nM (e.g., as described in Example 9);

(b) a HCV NS3 chimeric antibody having an equilibrium dissociation constant ($K_D$) of from about 10.0 nM to about 100.0 nM, optionally of about 50 nM, about 56 nM, about 62 nM, about 68 nM, or about 74 nM (e.g., as described in Example 10);

(c) a HCV NS4 chimeric antibody having an equilibrium dissociation constant ($K_D$) of from about 0.1 nM to about 1.0 nM, optionally of about 0.3 nM, about 0.4 nM, about 0.5 nM, or about 0.6 nM (e.g., as described in Example 11); and (d) a HCV NS5 chimeric antibody having an equilibrium dissociation constant ($K_D$) of from about 1.0 nM to about 10.0 nM, optionally of about 8.4 nM, about 8.6 nM, about 8.8 nM, or about 9.0 nM (e.g., as described in Example 12).

Other standard tests also can be done on the antibodies, for example, the pI value of the antibodies can be obtained, such as for the chimeric antibodies as described in Example 13. In one embodiment, the chimeric antibodies according to the invention which specifically bind to a HCV protein epitope optionally each comprise a pI value ranging from about 7.8 to about 9.0. In another embodiment, the chimeric antibody is selected from the group consisting of: (a) a HCV core chimeric antibody having a pI value of from about 8.8 to about 9.2, optionally about 9.0; (b) a HCV NS3 antibody having a pI value of between about 8.5 and about 9.0; (c) a HCV NS4 chimeric antibody having a pI value of between about 7.8 and about 8.7, and (d) a HCV NS5 chimeric antibody having a pI value of between about 8.0 and about 8.9.

Optionally, the recombinant antibodies (e.g., chimeric antibodies) are subjected to epitope mapping procedures to identify the region of the target antigen to which they bind. A variety of methods of epitope mapping are known in the art (see, for example, *Current Protocols in Immunology*, Coligan, J. E., et al. (ed.), J. Wiley & Sons, New York, N.Y.) and include, for example, phage and yeast display methods. Phage and yeast display methods can also be combined with random mutagenesis techniques in order to more precisely map the residues of the target antigen involved in antibody binding (see, for example, Chao, G., et al., *J. Mol. Biol.*, 10:539-50 (2004)).

In one embodiment of the present invention, the residues of the target antigen to which the recombinant antibodies bind are identified by a technique that combines scanning alanine mutagenesis with yeast display. Non-limiting examples of this procedure are provided in the Examples section below. The technique generally involves the preparation of a series of oligonucleotides encoding peptides each representing the target region of the antigen and in which each individual amino acid in this region was sequentially substituted by alanine. The target region of the antigen is determined either from the antigen used in the initial immunization to prepare the parent monoclonal antibody, or from a preliminary "low-resolution" screening using yeast or phage display. A wildtype version of the antigen is used as a control. Each oligonucleotide is cloned into an appropriate yeast display vector and each alanine mutant transformed into a suitable host, such as *E. coli*. Plasmid DNA is extracted and sequenced and clones are selected based on sequencing. Yeast display vectors are known in the art and are commercially available (for example, pYD1 available from Invitrogen, Carlsbad, Calif.).

The selected clones are then transformed into *Saccharomyces* cerevesiae cells, for example EBY100 cells (Invitrogen Corporation, Carlsbad, Calif.) and individual yeast clones cultured and induced for peptide expression. The induced yeast cells expressing the alanine mutants on the cell surface are incubated with the recombinant antibody and bound antibody is detected by conventional methods, for example using a labeled secondary antibody. Key residues in the target antigenic region can then be determined based on the identification of alanine mutants unable to bind to the recombinant antibody. A loss of antibody binding activity indicates that the mutant includes an alanine residue at a position that forms part of the epitope for the recombinant antibody.

6. Uses of Recombinant Antibodies

The recombinant antibodies of the present invention are suitable for use, for example, as diagnostic reagents for the detection of HCV, and/or as standardization reagents, positive control reagents or calibrator reagents in assays or kits for the detection of HCV antibodies in place of traditional plasma or serum. Standardization reagents can be employed, for example, to establish standard curves for interpolation of antibody concentration. Positive controls can be employed to establish assay performance characteristics and/or quantitate and monitor the integrity of the antigen(s) used in the assay. The present invention also provides for the use of a plurality of the recombinant antibodies, each recombinant antibody capable of specifically binding to a different HCV antigen, as standardized antibody sensitivity panels. Such sensitivity panels can be employed, for example, in place of traditional plasma or serum for quality control of HCV antibody detection kits, to establish assay performance characteristics and/or quantitate and monitor the integrity of the antigen(s) used in the assay. The present invention also contemplates the use of the recombinant antibodies in the treatment or prevention of a HCV infection.

One embodiment of the present invention thus provides for an immunodiagnostic reagent comprising one or more recombinant antibodies, each capable of specifically binding a diagnostically relevant region of a HCV protein.

In one embodiment of the present invention, the immunodiagnostic reagent comprises a plurality of (for example, two or more) recombinant antibodies each capable of detecting a different HCV antigen.

The immunodiagnostic reagent can be tailored for a specific end use by appropriate selection of the recombinant antibodies it comprises, thus making the immunodiagnostic reagent compatible with a number of existing HCV detection assay formats and kits. Tailoring the immunodiagnostic reagent in this manner also allows the reagent to be optimized for detection of certain stages of HCV infection. For example, an immunodiagnostic reagent comprising recombinant antibodies to HCV core and NS3 proteins, and optionally to HCV E2 protein, will allow for detection of early stage HCV infections, which can be of particular importance for example in screening blood products. One embodiment of the present invention thus provides for an immunodiagnostic reagent comprising a recombinant antibody specific for HCV core protein, a recombinant antibody specific for HCV NS3 protein, and optionally one or more of: a recombinant antibody specific for E2 protein, a recombinant antibody specific for HCV NS4 protein and a recombinant antibody specific for HCV NS5 protein, which is suitable for detection of early stage HCV infection and/or for standardization of kits and assays for early stage HCV infection.

In one embodiment of the present invention, each antibody included in the immunodiagnostic reagent shows a reactivity to its target antigen that is greater than or equal to that of a human serum sourced control under substantially identical assay conditions.

The present invention further provides for a method of standardizing HCV antibody detection assays using an immunodiagnostic reagent comprising a plurality of recombinant antibodies, each capable of specifically binding to a different HCV antigenic protein, as a sensitivity panel.

The present invention additionally provides for a method for detecting the presence of HCV antigens which comprises contacting a test sample suspected of containing HCV antigens with an immunodiagnostic reagent comprising one or more recombinant antibodies, each capable of specifically binding an HCV antigen, under conditions that allow formation of recombinant antibody:antigen complexes and detecting any recombinant antibody:antigen complexes formed.

The present invention also encompasses a method for detecting the presence of HCV antibodies which comprises contacting a test sample suspected of containing HCV antibodies with one or more antigens specific for the HCV antibodies, under conditions that allow formation of antigen/antibody complexes, detecting the antigen:antibody complexes, and employing an immunodiagnostic reagent comprising one or more recombinant antibodies, each capable of specifically binding one of the antigens employed in the method, as a positive control or standardization reagent.

The immunodiagnostic reagents of the present invention are suitable for use with assays and kits monitoring HCV responses in man as well as other vertebrate species susceptible to HCV infection and capable of generating an antibody response thereto. The immunodiagnostic reagents thus have human medical as well as veterinary applications.

Another aspect of the present invention provides the amino acid and corresponding nucleic acid sequences of the variable regions of antibodies specific for HCV core, NS3, NS4 and NS5 proteins, respectively. These sequences have utility in the generation of other recombinant antibodies as is known in the art, as well as for the identification of significantly homologous variable regions of human or humanized antibodies, such as those contained in a library or bank of such antibodies.

The present invention also encompasses the use of the recombinant antibodies and variable regions described herein in directed molecular evolution technologies such as phage display technologies, and bacterial and yeast cell surface display technologies, in order to produce novel recombinant antibodies in vitro (see, for example, Johnson et al., *Current Opinion in Structural Biology* 3:564 (1993) and Clackson et al., *Nature* 352:624 (1991)).

Optionally the immunodiagnostic reagent of the invention, e.g., the chimeric antibodies, can be used in commercial platform immunoassays, e.g., as described in Example 14. For instance, the four chimeric antibodies (HCV core, NS3, NS4 and NS5) prepared as described herein can be used in a variety of Abbott Laboratories HCV blood screening assays on the Prism®, AxSYM®, ARCHITECT® and EIA (Bead) platforms, as well as in other commercial and/or in vitro diagnostic assays as quality control reagents (e.g., sensitivity panels, calibrators, and positive controls).

7. Compositions Comprising Recombinant Antibodies

As noted above the recombinant antibodies of the present invention can be used diagnostically and/or therapeutically. One aspect of the present invention thus also provides for diagnostic and pharmaceutical compositions comprising one or more recombinant antibodies and a suitable carrier, diluent, and/or excipient. Suitable carriers, diluents, and/or excipients are well known in the art. Accordingly, also provided is the use of one or more recombinant antibodies of the invention for the manufacture of a medicament. For the preparation of pharmaceutical compositions, the carriers, diluents and excipients will be pharmaceutically acceptable. If desired, an adjuvant or other active ingredient may be included in the pharmaceutical compositions.

For administration to an animal, the pharmaceutical compositions can be formulated for administration by a variety of routes. For example, the compositions can be formulated for oral, topical, rectal or parenteral administration or for administration by inhalation or spray. The term parenteral as used herein includes subcutaneous injections, intravenous, intramuscular, intrathecal, intrasternal injection or infusion techniques. As indicated above, such pharmaceutical compositions are used in the treatment of various conditions in animals, including humans.

The pharmaceutical compositions preferably comprise a therapeutically effective amount of the recombinant antibody of the invention. The term "therapeutically effective amount" as used herein refers to an amount of a therapeutic agent needed to treat, ameliorate or prevent a targeted disease or condition, or to exhibit a detectable therapeutic or preventative effect. For an antibody, the therapeutically effective amount can be estimated initially, for example, either in cell culture assays or in animal models, usually in rodents, rabbits, dogs, pigs or primates. The animal model may also be used to determine the appropriate concentration range and route of administration. Such information can then be used to determine useful doses and routes for administration in the animal to be treated, including humans.

Various diagnostic compositions and pharmaceutical compositions suitable for different routes of administration and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000).

8. Kits Comprising Recombinant Antibodies

The present invention further provides for therapeutic, diagnostic and quality control kits comprising one or more recombinant antibodies of the invention.

a. Diagnostic and Quality Control Kits

One aspect of the present invention provides diagnostic kits for the detection of HCV. The kits comprise one or more recombinant antibodies of the present invention. The recombinant antibodies can be provided in the kit as detection reagents, either for use to capture and/or detect HCV antigens or for use as secondary antibodies for the detection of antigen:antibody complexes. Alternatively, the recombinant antibodies can be provided in the kit as a positive control reagent, a standardization reagent, calibration reagent or a sensitivity panel. In various embodiments, the diagnostic kit can further comprise reagents for detection of HCV antigens or reagents for the detection of HCV antibodies. In one embodiment, the present invention provides a diagnostic kit comprising reagents for detection of HCV antibodies, including one or more antigens specific for the HCV antibodies, and a positive control or standardization reagent comprising one or more recombinant antibodies of the invention, each capable of specifically binding one of the one or more antigens included in the kit.

As discussed above, optionally the immunodiagnostic reagent of the invention, e.g., the chimeric antibodies, can be used in kits for commercial platform immunoassays (e.g., HCV blood screening assays on the Prism®, AxSYM®, ARCHITECT® and EIA (Bead) platforms, as well as in other commercial and/or in vitro diagnostic assay) as quality control reagents (e.g., sensitivity panels, calibrators, and positive controls). Preparation of quality control reagents is well known in the art, and is described, e.g., on a variety of immunodiagnostic product insert sheets. HCV sensitivity panel members optionally can be prepared in varying amounts containing known quantities of HCV antibody ranging from "low" to "high", e.g., by spiking known quantities of chimeric antibodies according to the invention into an appropriate assay buffer (e.g., a phosphate buffer). These sensitivity panel members optionally are used to establish assay performance characteristics, and further optionally are useful indicators of the integrity of the immunoassay kit reagents, and the standardization of assays.

In another embodiment, the present invention provides for a quality control kit comprising one or more recombinant antibodies of the present invention for use as a sensitivity panel to evaluate assay performance characteristics and/or quantitate and monitor the integrity of the antigen(s) used in the assay.

The recombinant antibodies provided in the kit can incorporate a detectable label, such as a fluorophore, radioactive moiety, enzyme, biotin/avidin label, chromophore, chemiluminescent label, or the like, or the kit may include reagents for labeling the recombinant antibodies or reagents for detecting the recombinant antibodies. The recombinant antibodies can be provided in separate containers or pre-dispensed into an appropriate assay format, for example, into microtiter plates.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample, may also be included in the kit. The kit may additionally include one or more controls. One or more of the components of the kit may be lyophilized and the kit may further comprise reagents suitable for the reconstitution of the lyophilized components.

The various components of the kit are provided in suitable containers. As indicated above, one or more of the containers may be a microtiter plate. Where appropriate, the kit may also optionally contain reaction vessels, mixing vessels and other components that facilitate the preparation of reagents or the test sample. The kit may also include one or more instrument for assisting with obtaining a test sample, such as a syringe, pipette, forceps, measured spoon, or the like.

The kit can optionally include instructions for use, which may be provided in paper form or in computer-readable form, such as a disc, CD, DVD or the like.

b. Therapeutic Kits

The present invention additionally provides for therapeutic kits or packs containing one or more of recombinant antibodies of the invention or a pharmaceutical composition comprising one or more of the recombinant antibodies for use in the treatment or prevention of a HCV infection. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other therapeutic agents for use in combination with the recombinant antibodies of the invention. The kit may optionally contain instructions or directions outlining the method of use or dosing regimen for the recombinant antibodies and/or additional therapeutic agents.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits of the invention also may comprise an instrument for assisting with the administration of the composition to a patient. Such an instrument may be an inhalant, syringe, pipette, forceps, measured spoon, eye dropper or similar medically approved delivery vehicle.

To gain a better understanding of the invention described herein, the following examples are set forth. It will be understood that these examples are intended to describe illustrative embodiments of the invention and are not intended to limit the scope of the invention in any way.

EXAMPLES

Example 1

Preparation of a Human-Mouse Chimeric Antibody Specific for Hepatitis C Virus Core Protein #1

Preparation of a Hybridoma Cell Line

The hybridoma cell line anti-HCV Core 201-603-195 was developed using the PEG-mediated fusion technique described in Galfre et al., *Nature,* 266:550 (1977). Briefly, BALB/c female mice were immunized with a purified HCV recombinant core antigen known as pλ core (corresponding to amino acids 1-50 of the HCV polyprotein). The animal boost regimen utilized the Freunds Adjuvant System and sera samples were monitored in an HCV enzyme immunoassay (EIA) until an anti-HCV titer was identified. For the EIA, a HCV recombinant core antigen comprising core amino acids 1-150 (as well as NS3 amino acids 1192-1457) were coated on 96 well EIA plates for at least 1 hour at room temperature, and then were blocked with 2% BSA/PBS buffer for 1 hour. The mouse sera samples were added into the coated wells and the plates incubated for at least 1 hour at room temperature. After incubation, the plates were washed and incubated with horseradish peroxidase (HRP) labeled goat-anti mouse IgG antibody for about 1 hour. The plates were developed using O-Phenylenediamine-2HCl (OPD) and read at an optical density of 492 nm.

The mouse spleen cells were then fused with the SP2/0 myeloma and cultured at 37° C. in HAT-supplemented Iscove's Modified Dulbecco's Medium (IMDM) containing 10% fetal bovine serum (GIBCO). The hybridomas were tested 10-14 days later for anti-HCV reactivity by EIA. Hybridomas secreting anti-HCV monoclonal antibodies were cloned by standard single cell dilution techniques and subsequent clones were tested for reactivity by EIA. Positive cultures were expanded in IMDM containing 10% FBS and then frozen back in a cryopreservative for long term storage in liquid nitrogen.

The hybridoma cell line anti-HCV Core 201-603-195 was deposited with the American Type Culture Collection (ATCC) at 10801 University Boulevard, Manassas, Va. on Nov. 21, 2006 under Accession No. PTA-8027.

Isolation of mRNA and Identification of Mouse $V_H$ and $V_L$ Sequences

The anti-HCV Core 201-603-195 hybridoma cell line obtained as described above was cultured in Hybridoma Serum-Free Medium (HSFM) to obtain ~5×10⁶ cells for mRNA purification. Poly A+ mRNA was isolated from the cells and purified using Oligotex Direct mRNA Micro Kit (QIAGEN Inc., Valencia, Calif.) following the manufacturer's instructions.

The purified mRNA was then used as a template in a RT-PCR reaction using the Mouse Ig-Primer® set (EMD Biosciences Inc. (Novagen), San Diego, Calif.). Each Mu Ig $V_H$ 5'-A Primer, Mu Ig $V_H$ 5'-B Primer, Mu Ig $V_H$ 5'-C Primer, Mu Ig $V_H$ 5'-D Primer, Mu Ig $V_H$ 5'-E Primer, and Mu Ig $V_H$ 5'-F Primer was individually paired with Mu IgG $V_H$ 3'-2 Primer for the $V_H$ RT-PCR reaction. Each Mu Ig kappa $V_L$ 5'-A Primer, Mu Ig kappa $V_L$ 5'-B Primer, Mu Ig kappa $V_L$ 5'-C Primer, Mu Ig kappa $V_L$ 5'-D Primer, Mu Ig kappa $V_L$ 5'-E Primer, Mu Ig kappa $V_L$ 5'-F Primer, and Mu Ig kappa $V_L$ 5'-G Primer was individually paired with Mu Ig kappa $V_L$ 3'-1 Primer for the $V_L$ RT-PCR reaction. Each RT-PCR reaction was executed in 2× reaction Buffer (dNTP), each 5' and 3' primer pair and 2.5 units of RT-Platinum Taq HiFi Mix (Invitrogen Corp., Carlsbad, Calif.). The cDNA synthesis and pre-denaturation were performed at 1 cycle of 50° C. for 30 minutes and 1 cycle of 94° C. for 2 minutes, followed by the PCR reaction comprising denaturation for 1 minute at 94° C.; annealing 1 minute at 50° C. and extension 2 minutes at 68° C., with a final extension 6 minutes at 72° C. A total of 45 cycles were performed.

Positive PCR products were observed from the heavy chain (H) primer sets of B and C (VH-B, VH-C) and from the light chain (L) primer sets of A, B, E, F, G (VL-A, VL-B, VL-E, VL-F, VL-G). All positive PCR products were gel purified and cloned into the pCR TOPO 2.1 TA vector (Invitrogen Corp., Carlsbad, Calif.) and transformed into *E. coli* DH5α. The plasmid DNA was extracted from the *E. coli* cells using the QIAprep spin miniprep Kit (QIAGEN Inc., Valencia, Calif.) following the manufacturer's instructions and the $V_H$ or $V_L$ insert confirmed by EcoR I digestion for each PCR product. The final TA clone for each of the $V_H$ or $V_L$ inserts was selected by sequence alignment for either the light chain variable or the heavy chain variable using Vector NTI Advance™ software (Invitrogen Corp., Carlsbad, Calif.). In brief, each TA clone was grown in LB broth overnight with shaking at 37° C. Plasmid DNA from each clone was purified using the QIAprep spin miniprep kit (QIAGEN) and sequenced using M13 forward and reverse primers and the Big Dye Terminator v3.1 cycle sequencing kit (Applied Biosystems, Foster City, Calif.). Sequences were inputted into the Vector NTI Advance software and aligned. Sequences which aligned completely, i.e. had no mutations, insertions or deletions, were considered correct clones and were selected for further development. The sequence results identified VL-G TA clone number 1 as containing the correct $V_L$ sequence (SEQ ID NO:8, which encodes the polypeptide shown in SEQ ID NO:2) from the hybridoma cell line and the VH-C TA clone number 1 as containing the correct $V_H$ sequence (SEQ ID NO:7, which encodes the polypeptide shown in SEQ ID NO:1) (see FIGS. 2A-D).

Cloning the $V_H$ and $V_L$ Genes into pBOS Vectors

The pBOS vectors are known in the art and are described, e.g., in US 2005/0227289 (incorporated by reference for its teachings regarding the use of these vectors and the vectors themselves).

Using the VL-G TA clone number 1 as the template, a pair of PCR primers were designed to clone out the mouse $V_L$ sequence, namely, a HCV Core Antibody $V_L$ 5'-end primer comprising the sequence

```
                                              [SEQ ID NO: 3]
     5'-GCTCGCGATGCGACATTGTGATGTCACAGTCT-3',
``` and a HCV Core Antibody $V_L$ 3'-end primer comprising the sequence

```
                                              [SEQ ID NO: 4]
     5'-CACCGTACGTTTTATTTCCAGCTTGGT-3'.
```

The 5'-end primer (SEQ ID NO:3) contained a partial Kappa signal sequence and a Nru I restriction site, and the 3'-end primer (SEQ ID NO:4) contained a BsiW I restriction site. In addition, using the VH-C TA clone number 1 as the template, a pair of primers was designed to clone out the mouse $V_H$ sequence, namely, a HCV Core Antibody $V_H$ 5'-end primer comprising the sequence

```
                                              [SEQ ID NO: 5]
     5'-TTGTCGCGATTTTAAAAGGTGTCCAGTGCCAGATCCA

GTTGGTGCAGTCTGGACCT-3',
``` and a HCV Core Antibody $V_H$ 3'-end primer comprising the sequence

```
                                              [SEQ ID NO: 6]
     5'-TTGGTCGACGCTGAGGAGACGGTGACTGAGGTT-3'.
```

For this pair of primers, the 5'-end primer (SEQ ID NO:5) contained a partial heavy chain signal sequence and an Nru I restriction site and the 3'-end primer (SEQ ID NO:6) contained a Sal I restriction site.

The PCR was executed in 2×Pfx amplification buffer using 15 pmol each of the 5'-end and 3'-end primers, 1.25 units of Pfx DNA polymerase (Invitrogen, Carlsbad, Calif.), and 100 ng of TA clone plasmid DNA. The PCR was performed for 30 cycles of 15 seconds at 94° C. followed by 1 minute at 68° C.

The $V_L$ and $V_H$ sequences were independently amplified by PCR using the above primer pairs and the VL-G TA clone number 1 and VH-C TA clone number 1, respectively, as the templates. The $V_L$ and $V_H$ PCR products were restriction enzyme trimmed by Nru I/BsiW I and Nru I/Sal I digestion, respectively, and then cloned into either the pBOS-hck vector (for the $V_L$ sequence) or the pBOS-hcg vector (for the $V_H$ sequence) and transformed into E. coli DH5α. The pBOS-hck vector comprises the ampicillin resistance gene, pUC origin, SV40 origin, EF-1a promoter, kappa signal peptide and human kappa gene (hck). The pBOS-hcg vector comprises the ampicillin resistance gene, pUC origin, SV40 origin, EF-1a promoter, heavy chain signal peptide and human constant IgG gene (hcg1,2,non-a).

The transformed E. coli clones were grown in LB broth overnight with shaking at 37° C. Plasmid DNA was purified from each individual clone with the QIAprep spin miniprep kit (QIAGEN) followed by sequencing using the Bigdye Terminator v3.1 cycle sequencing kit (Applied Biosystems). Plasmids pBOS 201-603-195-L-T9 (containing the $V_L$ sequence) and pBOS 201-603-195-H-T4 (containing the $V_H$ sequence) were selected by sequencing. Once the respective pBOS clones were identified, separate E. coli DH5α cell banks containing either the pBOS 201-603-195-L-T9 plasmid or the pBOS 201-603-195-H-T4 plasmid were made to preserve the pBOS clones.

Chimeric Antibody Functional Testing pBOS 201-603-195-L-T9 and pBOS 201-603-195-H-T4 plasmid DNA was prepared using the Endofree plasmid Maxi-kit (QIAGEN, CA) by standard techniques. The high purity plasmid DNA thus obtained was then transiently transfected into COS 7L cells by electroporation (Gene Pulser, BIO-RAD). The transfected COS 7L cells were incubated at 37° C. in a 5% $CO_2$ incubator for three days, then harvested by centrifugation at 4000 rpm for 20 minutes and the supernatant collected. Following filtration and standard protein A agarose (Invitrogen) affinity purification, the purified anti-HCV core chimeric antibody was assayed by enzyme immunoassay (EIA) to confirm reactivity with HCV core antigen. The EIA was conducted as described above using horseradish peroxidase labeled goat anti-human ("GAH") IgG antibody as the detecting antibody and varying concentrations of the chimeric antibody. The EIA results demonstrated that the HCV core chimeric antibody from transient expression was reactive to the HCV core antigen.

Cloning the $V_H$ and $V_L$ Sequences into a Stable Expression Vector

The pBOS 201-603-195-L-T9 and pBOS 201-603-195-H-T4 clones were used to construct a plasmid clone for stable cell line transfection. First, the Srf I and Not I restriction sites flanking the $V_H$ and $V_L$ sequences in the respective vectors were employed to excise each of the $V_H$ and $V_L$ sequences from the vectors. The excised sequences were gel purified and then cloned into either the pBV vector (for the $V_H$ sequence) or the pJV vector (for the $V_L$ sequence). The pJV stuffer plasmid comprises a SV40 promoter, a murine DHFR gene, a CMV enhancer, an adenovirus major late (AML) promoter and a lambda stuffer. The pBV stuffer plasmid comprises a CMV enhancer, an adenovirus major late (AML) promoter and a lambda stuffer.

The pBV and pJV clones were screened by Srf I/Not I restriction enzyme digestion to identify those clones containing the correct insert. Once correct pBV and pJV clones had been identified, the heavy chain gene (from pBV) and light chain gene (from pJV) were cloned into one plasmid, by digesting each plasmid with Asc I and Pac I. For the light chain gene plasmid (pJV), Pac I/Asc I digestion produced two distinct bands at 4.8 Kb and 1.5 kb. For the heavy chain gene plasmid (pBV), Pac I/Asc I digestion produced two distinct band at 4.6 kb and 1.2 kb. The 4.8 kb DNA fragment from pJV plasmid and the 4.6 kb DNA fragment from pBV were gel purified and ligated together to form a pBJ plasmid that contained both the $V_H$ and $V_L$ sequences. After transformation, the final pBJ clone pBJ HCV core 201-603-195 was selected based on screening by Srf I/Not I digestion to confirm that it contained both the $V_H$ and $V_L$ sequences. The plasmid map for the final pBJ clone (pBJ HCV core 201-603-195) for the HCV core chimeric antibody thus obtained is shown in FIG. 1. The $V_H$ and $V_L$ gene sequences are shown in FIGS. 2A-B (SEQ ID NOs: 7 and 8, respectively). E. coli cell banks containing the pBJ HCV core 201-603-195 clone were made.

Establishing a Stable CHO Cell Line and Expression of the HCV Core Chimeric Antibody A Chinese Hamster Ovary (CHO, B3.2) cell line that lacks the dihydrofolate reductase (DHFR) gene was used for transfection and stable chimeric antibody expression as described below. The CHO cells were cultured and transfected by standard calcium phosphate mediated transfection with the pBJ HCV core 201-603-195 plasmid. The transfected HCV core CHO cells were cultured for several weeks prior to a single cell cloning into 96-well plates using the BD FACSAria flow cytometer sorter. Once the CHO clones had grown to more than 50% confluency, the supernatant was tested in an antigen specific EIA to rank the performance of the CHO clones. The EIA was conducted as described above using varying concentrations of the chimeric antibody. The 16 CHO clones that gave the highest signal in the EIA were expanded and re-assayed. Ten CHO clones were then selected based on the highest signal given in the EIA assay for weaning into CD CHO serum free tissue culture medium, including the clone CHO 201-603-486. Following one more single cell subcloning using the flow cytometer, HCV core CHO clone 201-603-486-333 was expanded for production of chimeric antibody and for development of cell banks for long-term storage in liquid nitrogen. The chimeric antibody was purified from this cell line using standard Protein A (POROS A50, Applied Biosystems) purification procedures followed by Sephadex G-25 Superfine desalting column purification.

The HCV core CHO 201-603-486-333 cell line was deposited with the American Type Culture Collection (ATCC) at 10801 University Boulevard, Manassas, Va. on May 2, 2006 under Patent Deposit Designation PTA-7570.

Example 2

Preparation of a Human-Mouse Chimeric Antibody Specific for Hepatitis C Virus NS3 Protein Preparation of a Hybridoma Cell Line The hybridoma cell line anti-HCV NS3 17-903-127 was developed as described in Example 1 using the purified HCV recombinant NS3 antigen known as CKS-33C-BCD in place of the core antigen. The CKS-33C-BCD recombinant antigen corresponds to amino acids 1192-1457+1676-1931 of the HCV polyprotein. The animal immunization regimen utilized one 200 μg boost in the Freunds Adjuvant System, with a pre-fusion boost in saline 2 weeks later.

The hybridoma cell line anti-HCV NS3 17-903-127 was deposited with the American Type Culture Collection (ATCC) at 10801 University Boulevard, Manassas, Va. on Nov. 21, 2006 under Accession No. PTA-8023.

Isolation of mRNA and Identification of Mouse $V_H$ and $V_L$ Sequences mRNA was isolated from the hybridoma cell line anti-HCV NS3 17-903-127 and the mouse $V_H$ and $V_L$ sequences obtained by RT-PCR as described in Example 1 with respect to the HCV Core 201-603-195 hybridoma cell line. Positive PCR products were observed from the heavy chain (H) primer sets of A and F (VH-A, VH-F) and from the light chain (L) primer sets of B, C and G (VL-B, VL-C, VL-G). All positive PCR products were gel purified, cloned into the pCR TOPO 2.1 TA vector and transformed into E. coli. Colony PCR reactions were used to confirm the clone insert. Briefly, the PCR was conducted using M13 forward and M13 reverse primer (Invitrogen), Taq DNA polymerase and boiled E. coli colony as the template. The PCR comprised denaturation 1 minute at 94° C.; annealing 1 minute at 50° C. and extension 2 minutes at 72° C., with a final extension 6 minutes at 72° C. for a total of 30 cycles. The clones giving the correct size for the PCR products were grown in LB broth. Each plasmid DNA was purified using QIAprep spin miniprep Kit (QIAGEN) and sequenced using M13 forward and reverse primers with the Big Dye Terminator v3.1 cycle sequencing kit (Applied Biosystems).

The final TA clone was selected by sequence alignment as described in Example 1. The sequence results confirmed that the VL-G clone contained the correct $V_L$ sequence (SEQ ID NO:16 encoding the polypeptide shown in SEQ ID NO:10), while the VH-A and F clones contained the correct $V_H$ sequence (SEQ ID NO:15 encoding the polypeptide shown in SEQ ID NO:9) (see also FIGS. 4A-D).

Cloning the $V_H$ and $V_L$ Genes into pBOS Vectors

Using the VL-G TA clone number 5 as the template, a pair of PCR primers were designed to clone out the mouse $V_L$ sequence, namely a HCV NS3 Antibody $V_L$ 5'-end primer comprising the sequence 5'-CTGTGGTTCCCCGGCTCGCGATGCGAT-GTTGTGATGGCCCAAAC
TCCACTCTCCCC-3'[SEQ ID NO:11], and a HCV NS3 Antibody $V_L$ 3'-end primer comprising the sequence

5'-GCGCATGCGTCGTACGTTTTATTTC-CAGCTTGGTCCCCCC-3' [SEQ ID NO:12].

The 5'-end primer contained a partial Kappa signal sequence and a Nru I restriction site and the 3'-end primer contained a BsiW I restriction site. In addition, using the VH TA clone number 2 as the template, a pair of primers was designed to clone out the mouse $V_H$ sequence, namely, a HCV NS3 Antibody $V_H$ 5'-end primer comprising the sequence 5'-GGCTTTTTCTTGTCGCGATTTTAAAAG-GTGTCCAGTGCGAAGTG
AAGCTGGTGGAGTCTG GGGGAGGC-3' [SEQ ID NO:13], and a HCV NS3 Antibody $V_H$ 3'-end primer comprising the sequence

5'-GCGCATGCATGCATTGTCGACGCGAG-GAGACTGTGAGAGTGGTGCCTTGGCCC-3' [SEQ ID NO:14].

For this pair of primers, the 5'-end primer contained a partial heavy chain signal sequence and an Nru I restriction site and the 3'-end primer contained a Sal I restriction site.

The $V_L$ and $V_H$ sequences were independently amplified by PCR using the above primer pairs and the VL-G TA clone number 5 and VH TA clone number 2, respectively, as the templates. The PCR was executed in 1×PCR amplification Buffer using 20 pmol each of the 5'-end and 3'-end primers, 1 unit of Taq DNA polymerase (Invitrogen), and 2 μl of bacterial colony as the template. The PCR was performed employing 30 cycles of 30 seconds at 94° C. and 30 seconds at 55° C. followed by 1 minute at 72° C.

The $V_L$ and $V_H$ PCR products were restriction enzyme trimmed by Nru I/BsiW I and Nru I/Sal I digestion, respectively, and then cloned into either the pBOS-hck vector (for the $V_L$ sequence) or the pBOS-hcg vector (for the $V_H$ sequence), as described in Example 1. Plasmids pBOS 17-903-127-L (containing the $V_L$ sequence) and pBOS 17-903-127-H (containing the $V_H$ sequence) were selected by sequencing as described in Example 1. Once the respective pBOS clones were identified, separate E. coli DH5α cell banks containing either the pBOS 17-903-127-L-T3 plasmid or the pBOS 17-903-127-H-T2 plasmid were made to preserve the pBOS clones.

Chimeric Antibody Functional Testing pBOS 17-903-127-L-T3 and pBOS 17-903-127-H-T2 plasmid DNA was prepared and transiently transfected into COS 7L cells as described in Example 1. The anti-HCV NS3 chimeric antibody was prepared from the transfected COS 7L cells as described in Example 1 and assayed by EIA to confirm reactivity with HCV NS3 antigen. The EIA was conducted as described in Example 1 using CKS-33C-BCD HCV NS3 antigen in place of the core antigen. The EIA results demonstrated that the chimeric antibody from transient expression was reactive to the HCV NS3 antigen.

Cloning the $V_H$ and $V_L$ Sequences into a Stable Expression Vector

Figure 3:
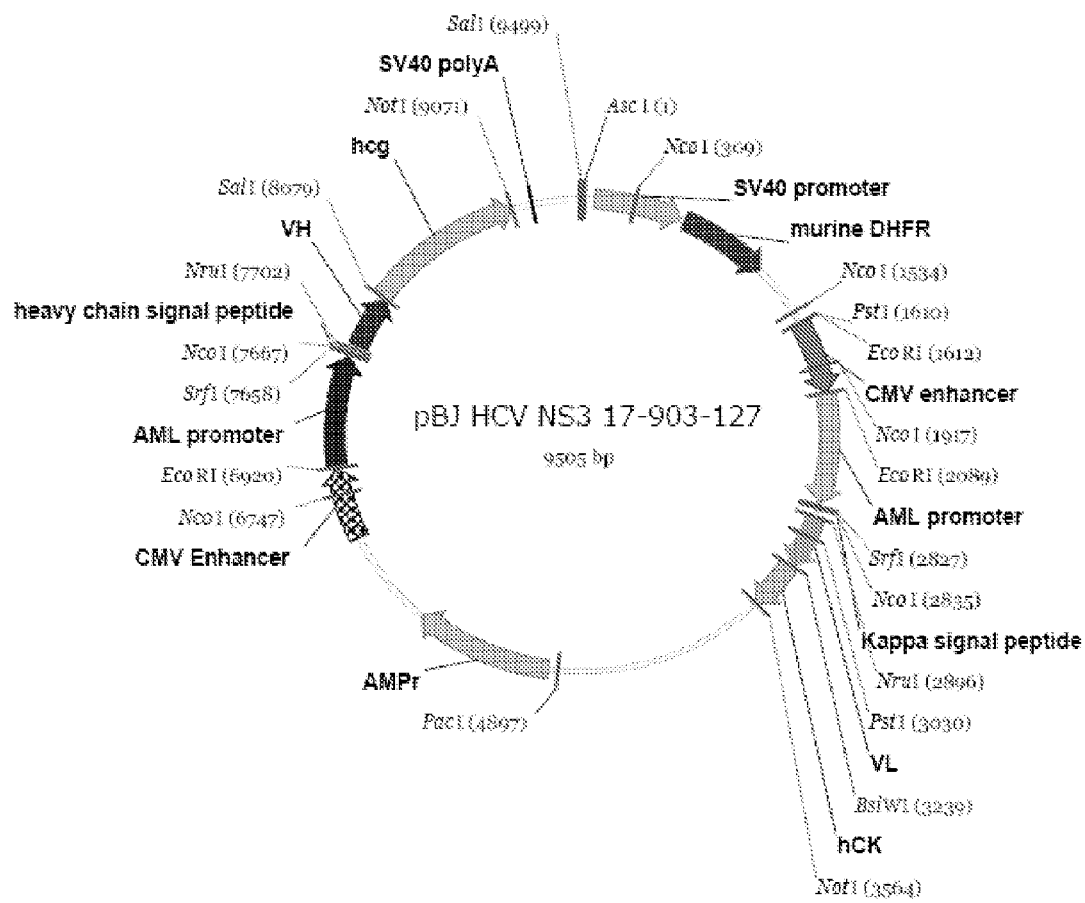
FIG. 3 presents a plasmid map of an expression plasmid used in the preparation of an anti-HCV NS3 chimeric antibody (HCV NS3 CHO 17-903-132sc171) in one embodiment of the present invention.

The pBOS 17-903-127-L-T3 and pBOS 17-903-127-H-T2 clones were used to construct a plasmid clone for stable cell line transfection by first cloning the sequences into the pBV vector (for the $V_H$ sequence) or the pJV vector (for the $V_L$ sequence) and subsequently ligating together the vector fragments obtained from Pac I/Asc I restriction enzyme digestion as described in Example 1 to provide the pBJ plasmid pBJ HCV NS3 17-903-127 that contains both the $V_H$ and the $V_L$ sequences. The pBJ clone was screened by Srf I/Not I digestion to confirm that it contains both sequences. The plasmid map for the final pBJ clone (pBJ HCV NS3 17-903-127) for the HCV NS3 chimeric antibody is shown in FIG. 3. The $V_H$ and $V_L$ gene sequences are shown in FIG. 4 (SEQ ID NO:15 and SEQ ID NO:16, respectively). E. coli DH5α cell banks containing the HCV pBJ HCV NS3 17-903-127 clone were made.

Establishing a Stable CHO Cell Line and Expression of the HCV Chimeric Antibody

The pBJ HCV NS3 17-903-127 plasmid was transfected by calcium phosphate mediated transfection into the DHFR-deficient Chinese Hamster Ovary cell line as described in Example 1. Culture and single cell cloning was conducted as described in Example 1. The 96 well plates were tested by antigen specific EIA and clone number 132 was selected for further development. The EIA was conducted as described above. The HCV NS3 17-903-132 CHO cell clone was cultured and single cell sorted into 96-well plates using the BD FACSAria flow cytometer sorter. CHO subclone number 171 was selected for weaning into CD-CHO serum free medium (Invitrogen). The final CHO cell line (HCV NS3 17-903-132sc171) was expanded for production of the chimeric antibody and for development of a discovery cell bank for storage in liquid nitrogen. The chimeric antibody was purified from this cell line using standard Protein A purification procedures as described in Example 1.

The HCV NS3 CHO 17-903-132sc171 cell line was deposited with the American Type Culture Collection (ATCC) at 10801 University Boulevard, Manassas, Va. on May 2, 2006 under Patent Deposit Designation PTA-7573.

Example 3

Preparation of a Human-Mouse Chimeric Antibody Specific for Hepatitis C Virus NS4 Protein Preparation of a Hybridoma Cell Line The hybridoma cell line anti-HCV NS4 E99H6C34 was developed as described in Example 1 using the purified HCV recombinant NS4 antigen known as CKS-C100 in place of the core antigen. The CKS-C100 recombinant antigen corresponds to amino acids 1676-1931 of the HCV polyprotein. The animal boost regimen used the Freunds Adjuvant System and sera samples were monitored in an HCV EIA until an anti-HCV titer was identified. The EIA was conducted as described in Example 1 using the CKS-C100 HCV NS4 antigen in place of the core antigen. The mouse spleen cells were fused with the SP2/0 myeloma and cultured at 37° C. in HAT-supplemented Dulbecco's Modified Eagle's Medium (DMEM) containing 20% fetal bovine serum (GIBCO). The hybridomas were tested 10-14 days later for anti-HCV reactivity in an EIA. Hybridomas secreting anti-HCV monoclonal antibodies were cloned by single cell dilution techniques and subsequent clones were tested for reactivity in an EIA. Positive cultures were expanded in DMEM containing 10% FBS and frozen back in a cryopreservative for long term storage in liquid nitrogen.

The hybridoma cell line anti-HCV NS4 E99H6C34 was deposited with the American Type Culture Collection (ATCC) at 10801 University Boulevard, Manassas, Va. on Nov. 21, 2006 under Accession No. PTA-8021.

Isolation of mRNA and Identification of Mouse $V_H$ and $V_L$ Sequences mRNA was isolated from the hybridoma cell line anti-HCV NS4 E99H6C34 and the mouse $V_H$ and $V_L$ sequences obtained by RT-PCR as described in Example 1 with respect to the HCV Core 201-603-195 hybridoma cell line. Positive PCR products were observed from the heavy chain (H) primer set of C (VH-C) and from the light chain (L) primer sets of B, C and G (VL-B, VL-C, VL-G). All positive PCR products were gel purified, cloned into the pCR TOPO 2.1 TA vector and transformed into *E. coli* DH5α. The plasmid DNA was extracted from the *E. coli* cells and the $V_H$ or $V_L$ insert confirmed by EcoR I digestion for each PCR product. The final TA clone was selected by sequence alignment as described in Example 1. The sequence results confirmed that VL-G TA clone number 5 contained the correct $V_L$ sequence (SEQ ID NO:24 encoding a polypeptide as shown in SEQ ID NO:18), while the VH-C TA clone number 16 contained the correct $V_H$ sequence (SEQ ID NO:23 encoding a polypeptide as shown in SEQ ID NO:17) (see also FIGS. 6A-D).

Cloning the $V_H$ and $V_L$ Sequences into pBOS Vectors

Using the VL-G TA clone number 5 as the template, a pair of PCR primers were designed to clone out the mouse $V_L$ sequence, namely, a HCV NS4 Antibody $V_L$ 5'-end primer comprising the sequence
5'-GCTCGCGATGCGATGTTGTGATGACCCAAAC-3' [SEQ ID NO:19], and a HCV NS4 Antibody $V_L$ 3'-end primer comprising the sequence
5'-CACCGTACGTTTGATTTCCAGCTTGGTGC-3' [SEQ ID NO:20].

The 5'-end primer contained a partial Kappa signal sequence and a Nru I restriction site and the 3'-end primer contained a BsiW I restriction site. In addition, using the VH-C TA clone number 16 as the template, a pair of primers was designed to clone out the mouse $V_H$ sequence, namely, a HCV NS4 Antibody $V_H$ 5'-end primer comprising the sequence
5'-TACTTCGCGACAGATCCAGTTGGTGCAGTC-3' [SEQ ID NO:21], and a HCV NS4 Antibody $V_H$ 3'-end primer comprising the sequence
5'-TGGTCGACGCTGAGGAGACTGTGAGAGTGGT-3' [SEQ ID NO:22].

For this pair of primers, the 5'-end primer contained a partial heavy chain signal sequence and a Nru I restriction site and the 3'-end primer contained a Sal I restriction site.

The $V_L$ and $V_H$ sequences were independently amplified by PCR using the above primer pairs and the VL-G TA clone number 5 and VH-C TA clone number 16, respectively, as the templates. The PCR was executed in 2×Pfx amplification Buffer using 15 pmol each of the 5'-end and 3'-end primers, 1.25 units of Pfx DNA polymerase (Invitrogen) and 100 ng of TA clone plasmid DNA as the template. The PCR was performed using 30 cycles of 15 seconds at 94° C. followed by 1 minute at 68° C.

The $V_L$ and $V_H$ PCR products were restriction enzyme trimmed by Nru I/BsiW I and Nru I/Sal I digestion, respectively, and then cloned into either the pBOS-hck vector (for the $V_L$ sequence) or the pBOS-hcg vector (for the $V_H$ sequence), as described in Example 1. Plasmids pBOS E99H6C34-L-T4 (containing the $V_L$ sequence) and pBOS E99H6C34-H-T2 (containing the $V_H$ sequence) were selected by sequencing. Once the respective pBOS clones were identified, separate *E. coli* DH5α cell banks containing either the pBOS E99H6C34-L-T4 plasmid or the pBOS E99H6C34-H-T2 plasmid were made to preserve the pBOS clones.

Chimeric Antibody Functional Testing pBOS E99H6C34-L-T4 and pBOS E99H6C34-H-T2 plasmid DNA was prepared and transiently transfected into COS 7L cells as described in Example 1. The anti-HCV NS3 chimeric antibody was prepared from the transfected COS 7L cells as described in Example 1 and assayed by EIA to confirm reactivity with HCV NS4 antigen (C100 Ag). The EIA was conducted as described above. The EIA results demonstrated that the chimeric antibody from transient expression was reactive to the HCV NS4 antigen.

Cloning the $V_H$ and $V_L$ Sequences into a Stable Expression Vector

Figure 5:
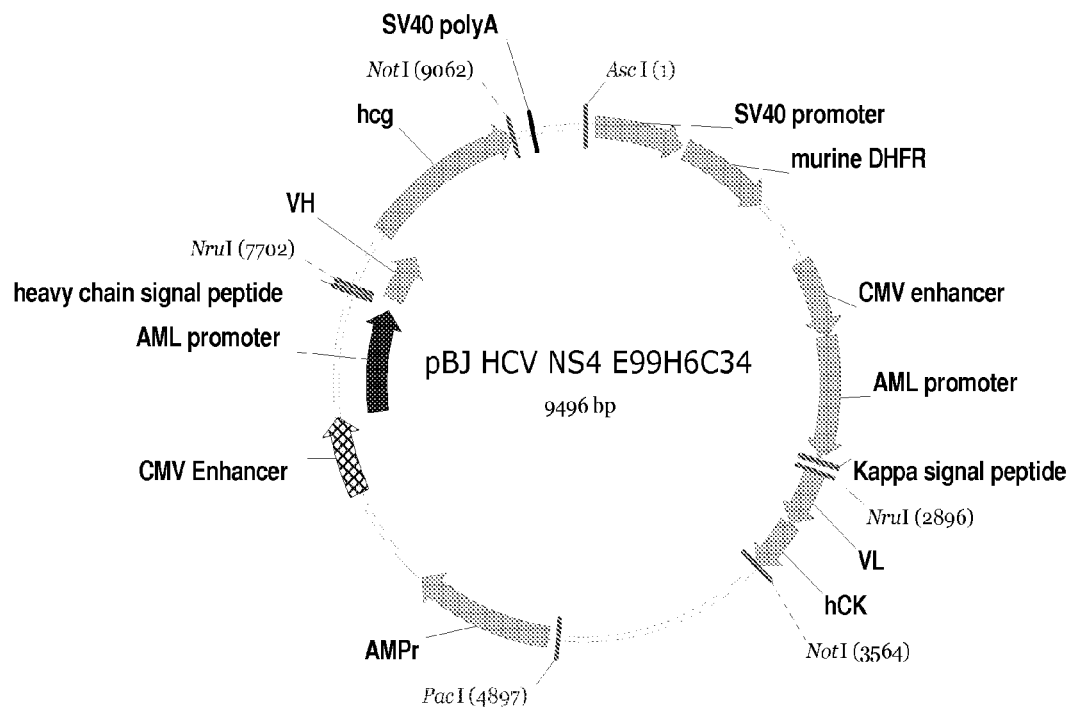
FIG. 5 presents a plasmid map of an expression plasmid used in the preparation of an anti-HCV NS4 chimeric antibody (HCV NS4 CHO E99H6C34sc203) in one embodiment of the present invention.

The pBOS E99H6C34-L-T4 and pBOS E99H6C34-H-T2 clones were used to construct a plasmid clone for stable cell line transfection by first cloning the sequences into the pBV vector (for the $V_H$ sequence) or the pJV vector (for the $V_L$ sequence) and subsequently ligating together the vector fragments obtained from Pac I/Asc I restriction enzyme digestion as described in Example 1 to provide the pBJ plasmid pBJ HCV NS4 E99H6C34 that contains both the $V_H$ and the $V_L$ sequences. The pBJ clone was screened by Srf I/Not I digestion to confirm that it contains both sequences. The plasmid map for the final pBJ clone (pBJ HCV NS4 E99H6C34) for the HCV NS4 chimeric antibody is shown in FIG. 5. The $V_H$ and $V_L$ gene sequences are shown in FIGS. 6A-B (SEQ ID NO:23 and SEQ ID NO:24, respectively). *E. coli* DH5α cell banks containing the pBJ HCV NS4 E99H6C34 clone were made.

Establishing a Stable CHO Cell Line and Expression of the HCV Chimeric Antibody

The pBJ HCV NS4 E99H6C34 plasmid was transfected by calcium phosphate mediated transfection into the DHFR-deficient Chinese Hamster Ovary cell line as described in Example 1. Culture and single cell cloning was conducted as described in Example 1. When the CHO clones had grown to more than 50% confluency, the supernatant was tested in an antigen specific EIA to rank the performance of the CHO clones. The EIA was conducted as described above. The 16 CHO clones showing the highest signal were expanded and re-assayed by an antigen specific EIA. Six CHO clones were selected for weaning into CD CHO serum free tissue culture medium. HCV NS4 CHO clone #203 was expanded to produce purified chimeric antibody and for development of a discovery cell bank for storage in liquid nitrogen. The chimeric antibody was purified from this cell line using standard Protein A purification procedures as described in Example 1.

The HCV NS4 CHO E99H6C34sc203 cell line was deposited with the American Type Culture Collection (ATCC) at 10801 University Boulevard, Manassas, Va. on May 2, 2006 under Patent Deposit Designation PTA-7569.

Example 4

Preparation of a Human-Mouse Chimeric Antibody Specific for Hepatitis C Virus NS5 Protein Preparation of a Hybridoma Cell Line The hybridoma cell line anti-HCV NS5 48-311-387 was developed as described in Example 1 using the HCV recombinant antigen known as CKS EF. The CKS-EF recombinant antigen corresponds to amino acids 1932-2191+2188-2481 of the HCV polyprotein. BALB/c female mice were immunized once with 200 µg of purified HCV recombinant antigen (CKS-EF) using the Freunds Adjuvant System. Three mice were administered a pre-fusion boost 3 days prior to harvesting the spleens.

The hybridoma cell line anti-HCV NS5 48-311-387 was deposited with the American Type Culture Collection (ATCC) at 10801 University Boulevard, Manassas, Va. on Nov. 21, 2006 under Accession No. PTA-8022.

Isolation of mRNA and Identification of Mouse $V_H$ and $V_L$ Sequences mRNA was isolated from the hybridoma cell line anti-HCV NS5 48-311-387 and the mouse $V_H$ and $V_L$ sequences obtained by RT-PCR as described in Example 1 with respect to the HCV Core 201-603-195 hybridoma cell line. Positive PCR products were observed from the heavy chain (H) primer set of C (VH-C) and from the light chain (L) primer sets of B, C and G (VL-B, VL-C, VL-G). All positive PCR products were gel purified, cloned into the pCR TOPO 2.1 TA vector and transformed into E. coli DH5α. The plasmid DNA was extracted from the E. coli cells and the $V_H$ or $V_L$ insert confirmed by EcoR I digestion for each PCR product. The final TA clones were selected by sequence alignment as described in Example 1. The sequence results confirmed that VL-G TA clone number 8 contained the correct $V_L$ sequence (SEQ ID NO:32 encoding a polypeptide as shown in SEQ ID NO:26), while the VH-C TA clone number 13 contained the correct $V_H$ sequence (SEQ ID NO:31 encoding a polypeptide as shown in SEQ ID NO:25) (see also FIGS. 8A-D).

Cloning the $V_H$ and $V_L$ Sequences into pBOS Vectors

Using the VL-G TA clone number 8 as the template, a pair of PCR primers were designed to clone out the mouse $V_L$ sequence, namely a HCV NS5 Antibody $V_L$ 5'-end primer comprising the sequence 5'-GCTCGCGATGCGACATTGTGATGTCACAGT-3' [SEQ ID NO:27], and a HCV NS5 Antibody $V_L$ 3'-end primer comprising the sequence

5'-CACCGTACGTTTCAGCTCCAGCTTGGT-3' [SEQ ID NO:28].

The 5'-end primer contained a partial Kappa signal sequence and a Nru I restriction site and the 3'-end primer contained a BsiW I restriction site. In addition, using the VH-C TA clone number 13 as the template, a pair of primers was designed to clone out the mouse $V_H$ sequence, namely, a HCV NS5 Antibody $V_H$ 5'-end primer comprising the sequence 5'-TACTTCGCGAGAGGTTCAGCTGCAGCAGT-3' [SEQ ID NO:29], and a HCV NS5 Antibody $V_H$ 3'-end primer comprising the sequence

5'-TGGTCGACGCTGCAGAGACAGTGACCAG-3' [SEQ ID NO:30].

For this pair of primers, the 5'-end primer contained a partial heavy chain signal sequence and an Nru I restriction site and the 3'-end primer contained a Sal I restriction site.

The $V_L$ and $V_H$ sequences were independently amplified by PCR using the above primer pairs and the VL-G TA clone number 5 and VH-C TA clone number 16, respectively, as the templates. The PCR was executed in 2×Pfx amplification buffer using 15 pmol each of 5'-end and 3'-end primers, 1.25 units of Pfx DNA polymerase (Invitrogen) and 100 ng of TA clone plasmid DNA as template. The PCR comprised 30 cycles of 15 seconds at 94° C. followed by 1 minute at 68° C.

The $V_L$ and $V_H$ PCR products were restriction enzyme trimmed by Nru I/BsiW I and Nru I/Sal I digestion, respectively, and then cloned into either the pBOS-hck vector (for the $V_L$ sequence) or the pBOS-hcg vector (for the $V_H$ sequence), as described in Example 1. Plasmids pBOS 48-311-387-L-T4 (containing the $V_L$ sequence) and pBOS 48-311-387-H-T2 (containing the $V_H$ sequence) were selected by sequencing. Once the respective pBOS clones were identified, separate E. coli cell banks containing either the pBOS 48-311-387-L-T4 plasmid or the pBOS 48-311-387-H-T2 plasmid were made to preserve the pBOS clones.

Chimeric Antibody Functional Testing pBOS 48-311-387-L-T4 and pBOS 48-311-387-H-T2 plasmid DNA was prepared and transiently transfected into COS 7L cells as described in Example 1. The anti-HCV NS5 chimeric antibody was prepared from the transfected COS 7L cells as described in Example 1 and assayed by EIA to confirm reactivity with HCV NS5 antigen (SOD-NS5; Chiron Corporation). The EIA was conducted as described in Example 1 using the CKS EF HCV NS5 antigen in place of core antigen. The EIA results demonstrated that the chimeric antibody from transient expression reactive to the HCV NS5 antigen.

Cloning the $V_H$ and $V_L$ Sequences into a Stable Expression Vector

Figure 7:
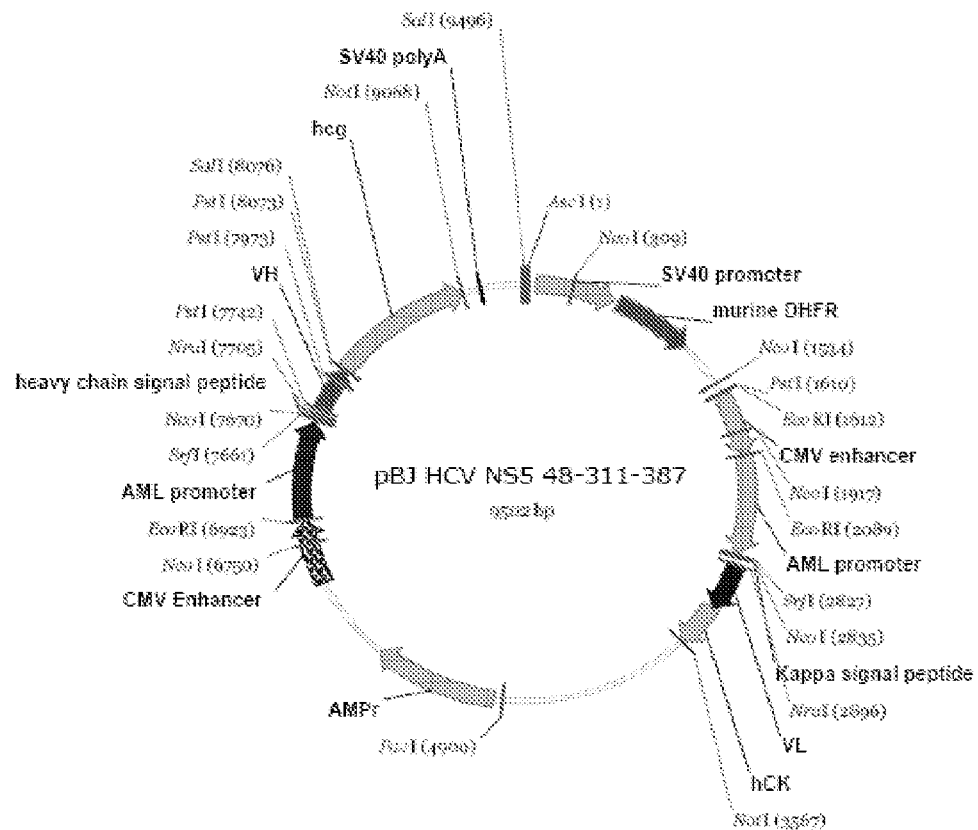
FIG. 7 presents a plasmid map of an expression plasmid used in the preparation of an anti-HCV NS5 chimeric antibody (HCV NS5 CHO 48-311-271-455) in one embodiment of the present invention.

The pBOS 48-311-387-L-T4 and pBOS 48-311-387-H-T2 clones were used to construct a plasmid clone for stable cell line transfection by first cloning the sequences into the pBV vector (for the $V_H$ sequence) or the pJV vector (for the $V_L$ sequence) and subsequently ligating together the vector fragments obtained from Pac I/Asc I restriction enzyme digestion as described in Example 1 to provide the pBJ plasmid pBJ HCV NS5 48-311-387 that contains both the $V_H$ and the $V_L$ sequences. The pBJ clone was screened by Srf I/Not I digestion to confirm that it contains both sequences. The plasmid map for the final pBJ clone (pBJ HCV NS5 48-311-387) for the HCV NS5 chimeric antibody is shown in FIG. 7. The $V_H$ and $V_L$ gene sequences are shown in FIGS. 8A-B (SEQ ID NO:31 and 32, respectively). E. coli DH5α cell banks containing the pBJ HCV NS5 48-311-387 clone were made.

Establishing a Stable CHO Cell Line and Expression of the HCV Chimeric Antibody

The pBJ HCV NS5 48-311-387 plasmid was transfected by calcium phosphate mediated transfection into the DHFR-deficient Chinese Hamster Ovary cell line as described in Example 1. Culture and single cell cloning was conducted as described in Example 1. When the CHO clones had grown to more than 50% confluency, the supernatant was tested in an antigen specific EIA to rank the performance of the CHO clones. The EIA was conducted as described above. The 6 CHO clones showing the highest signal were expanded and re-assayed by an antigen specific EIA. 4 CHO clones were selected for single cell cloning using the BD FACSAria flow sorter. When confluent growth was apparent, the cultures were screened in an EIA that resulted in the selection of 5 clones to be weaned into serum free medium, including the clone designated CHO 48-311-271. One final subcloning resulted in the selection of HCV NS5 CHO clone 48-311-271-455 for cell banking purposes. The cell line was expanded for production of chimeric antibodies and for development of a discovery cell bank for storage in liquid nitrogen. The chimeric antibody was purified from this cell line using standard Protein A purification procedures as described on Example 1.

The HCV NS5 CHO 48-311-271-455 cell line was deposited with the American Type Culture Collection (ATCC) at 10801 University Boulevard, Manassas, Va. on May 2, 2006 under Patent Deposit Designation PTA-7572.

Example 5

Epitope Mapping of HCV Core Chimeric Monoclonal Antibody

The binding site of the anti-HCV core mouse monoclonal antibody described in Example 1 was mapped to the HCV core protein region comprising amino acids 32-36 (GGVYL; SEQ ID NO:33) using synthetic peptides. Briefly, synthesized short peptides were used to coat the wells of an EIA plate and were blocked with 2% BSA/PBS buffer. The anti-HCV core mouse monoclonal antibody was added to the EIA plates and incubated for at least 1 hour. The EIA plates were then washed and incubated with goat anti-mouse ("GAM") HRP labeled antibody for another 1 hour. The plates were washed and developed using 0-Phenylenediamine-2HCl (OPD), and read at an optical density of 492 nm.

A combination of alanine scanning and yeast display technology were subsequently used for fine epitope mapping. Briefly, a library of alanine mutants was constructed using a set of synthetic DNA oligonucleotides which encoded peptides each representing the 27-39 region (GGQIVG-GVYLLPR; SEQ ID NO:34) of the core antigen and in which each individual amino acid in this region was sequentially substituted by alanine. A wildtype core 27-39 fragment was used as control. The DNA oligonucleotides were cloned into the yeast display vector (pYD41; based on vector pYD1 available from Invitrogen) at the Nco I and Not I restriction enzyme sites. Each HCV core alanine mutant was then transformed into *E. coli* and plasmid DNA was extracted and sequenced. Final clone selection was based on sequencing. The selected clones were transformed into EBY100 *Saccharomyces cerevesiae* cells (Invitrogen). Individual yeast clones were cultured and induced for HCV core peptide expression. The induced yeast cells were incubated with the HCV core chimeric antibody and a secondary antibody (Alexa Fluor 633 goat anti human IgG; Invitrogen), and analyzed by Fluorescence Activated Cell Sorter (FACS Calibur) to determine which alanine mutants had lost antibody binding activity. A loss of antibody binding activity indicated that the mutant included an alanine at a position that formed part of the epitope for the chimeric antibody. The data showed that HCV core antigen positions 29 (Gln), 31 (Val), 32 (Gly), 33 (Gly), 36 (Leu) (as shown in FIG. 9A) are binding sites for the HCV core chimeric antibody.

These results confirm that this region set forth in the sequence QIVGGVYL (SEQ ID NO:100) comprises an epitope for binding to the HCV core chimeric antibody. The results confirm that for binding to the HCV core chimeric antibody, these antigenic residues must remain invariant while others can be altered, as in the sequence QXVGGXXL, where X is any amino acid (SEQ ID NO:101), or where X is Ala or Gly (SEQ ID NO:102).

Example 6

Epitope Mapping of HCV NS3 Chimeric Monoclonal Antibody

The HCV NS3 mouse monoclonal antibody produced by hybridoma cell line anti-HCV NS3 17-903-127 was raised against the region of the HCV NS3 antigen spanning amino acids 1192-1457 (265aa). In order to map the epitope that the NS3 chimeric antibody binds within this region, the 265aa region was broken up into twelve overlapping fragments by constructing twelve pairs of DNA oligonucleotides. Specifically, these oligonucleotides represented the following fragments: 1190-1216; 1212-1239; 1235-1257; 1251-1272; 1273-1301; 1297-1323; 1321-1347; 1341-1367; 1364-1387; 1388-1414; 1411-1438, and 1434-1459. The pairs of DNA oligonucleotides were annealed and cloned into yeast display vector (pYD41) at Nco I and Not I restriction enzyme sites. Each of the HCV NS3 vectors was transformed into *E. coli* and plasmid DNA was extracted and sequenced. Final clone selection was based on sequencing. The selected clones were transformed into EBY100 *Saccharomyces cerevesiae* cells. Individual yeast clones were cultured and induced for HCV NS3 peptide expression. The induced yeast cells were incubated with the HCV NS3 chimeric antibody and secondary antibody (Alexa Fluor 633 goat anti human IgG), and analyzed by Fluorescence Activated Cell Sorter (FACS Calibur) to determine which fragment demonstrated positive binding to the chimeric antibody, thus indicating the epitope location. The data showed that only HCV NS3 fragment 1190-1216 (AKAVDFVPVESLETTMRSPVFTDNSSP; SEQ ID NO:35) demonstrated positive binding.

Alanine scanning and yeast display technology were then used for fine epitope mapping. A library of alanine mutants representing the 1190-1216 region was constructed using a set of synthetic DNA oligonucleotides as generally described in Example 5 for the core antigen. Wildtype NS3 1190-1216 fragment was used as control. Yeast display was carried out as described in Example 5 and the induced yeast cells were incubated with the HCV NS3 chimeric antibody and a secondary antibody (Alexa Fluor 633 goat anti human IgG), and analyzed by Fluorescence Activated Cell Sorter (FACS Calibur) to determine which alanine mutants had lost antibody binding activity. The data showed that HCV NS3 antigen positions 1194 (Asp), 1195 (Phe), 1196 (Val), 1197 (Pro), 1199 (Glu), 1201 (Leu), 1202 (Glu), and 1205 (Met) (as shown in FIG. 9B) are binding sites for the HCV NS3 chimeric antibody.

These results confirm that this region set forth in the sequence DFVPVESLETTM (SEQ ID NO:103) comprises an epitope for binding to the HCV NS3 chimeric antibody. The results confirm that for binding to the HCV NS3 chimeric antibody, these antigenic residues must remain invariant while others can be altered, as in the sequence DFVPXEX- LEXXM, where X is any amino acid (SEQ ID NO:104), or where X is Ala or Gly (SEQ ID NO:105).

Example 7

Epitope Mapping of HCV NS4 Chimeric Monoclonal Antibody

The HCV NS4 chimeric monoclonal antibody produced by the HCV NS4 CHO E99H6C34sc203 cell line was mapped to the region of the HCV NS4 antigen represented by amino acids 1692-1713 (PAIIPDREVLYREFDEMEECSQ; SEQ ID NO:36) using synthetic DNA oligonucleotides and standard yeast display technology, as generally described in Examples 5 and 6. Alanine scanning and yeast display technology were then used for fine epitope mapping. A library of alanine mutants representing the 1692-1713 region was constructed using a set of synthetic DNA oligonucleotides as generally described in Example 5 for the core antigen. Wildtype NS4 1692-1713 fragment was used as control. Yeast display was carried out as described in Example 5 and the induced yeast cells were incubated with the HCV NS4 chimeric antibody and a secondary antibody (Alexa Fluor 633 goat anti human IgG), and analyzed by Fluorescence Activated Cell Sorter (FACS Calibur) to determine which alanine mutants had lost antibody binding activity. The data showed that HCV NS4 antigen positions 1701 (Leu), 1702 (Tyr), 1704 (Gly), 1705 (Phe), 1706 (Asp) (as shown in FIG. 9C) are binding sites for the HCV NS4 chimeric antibody.

These results confirm that this region set forth in the sequence LYREFD (SEQ ID NO:106) comprises an epitope for binding to the HCV NS4 chimeric antibody. The results confirm that for binding to the HCV NS4 chimeric antibody, these antigenic residues must remain invariant while others can be altered, as in the sequence LYXEFD, where X is any amino acid (SEQ ID NO:107), or where X is Ala or Gly (SEQ ID NO:108).

Example 8

Epitope Mapping of HCV NS5 Chimeric Monoclonal Antibody

The HCV NS5 mouse monoclonal antibody produced by hybridoma cell line anti-HCV NS5 48-311-387 was raised against the region of the HCV NS5 antigen spanning amino acids 2054-2481 (428aa) region. In order to map the epitope that the NS5 chimeric antibody binds within this region, the 428aa region was broken up into eighteen overlapping fragments by constructing eighteen pairs of DNA oligonucleotides. Specifically, these oligonucleotides represented the following fragments: 2048-2076; 2075-2101; 2098-2124; 2120-2146; 2144-2177; 2169-2196; 2193-2221; 2220-2247; 2245-2272; 2271-2296; 2292-2318; 2313-2339; 2336-2363; 2360-2386; 2382-2408; 2408-2436; 2435-2462, and 2457-2486. Epitope mapping utilizing these eighteen pairs of oligonucleotides and the HCV NS5 chimeric antibody was conducted as described in Example 6. The data showed that only the HCV NS5 fragment 2382-2408 (2382-AESYSSMPPLEGEPGDPDLSDGSWSTV-2408; SEQ ID NO:37) demonstrated positive binding.

Alanine scanning and yeast display technology were then used for fine epitope mapping. A library of alanine mutants representing the 2382-2408 region was constructed using a set of synthetic DNA oligonucleotides as generally described in Example 5 for the core antigen. Wildtype NS5 2382-2408 fragment was used as control. Yeast display was carried out as described in Example 5 and the induced yeast cells were incubated with the HCV NS5 chimeric antibody and a secondary antibody (Alexa Fluor 633 goat anti human IgG), and analyzed by Fluorescence Activated Cell Sorter (FACS Calibur) to determine which alanine mutants had lost antibody binding activity. The data showed that HCV NS5 antigen positions 2390 (Pro), 2391 (Leu), 2392 (Glu), 2393 (Gly), 2394 (Glu), 2395 (Pro), 2397 (Asp), 2398 (Pro), and 2400 (Leu) (as shown in FIG. 9D) are binding sites for the HCV NS5 chimeric antibody.

These results confirm that this region set forth in the sequence PLEGEPGDPDL (SEQ ID NO:109) comprises an epitope for binding to the HCV NS5 chimeric antibody. The results confirm that for binding to the HCV NS5 chimeric antibody, these antigenic residues must remain invariant while others can be altered, as in the sequence PLEGEPXDPXL, where X is any amino acid (SEQ ID NO:110), or where X is Ala or Gly (SEQ ID NO:111).

Example 9

Determination of the Equilibrium Dissociation Constant ($K_D$) for HCV Core Chimeric Monoclonal Antibody The yeast cells containing wildtype HCV 27-39 core fragment from Example 5 were cultured and induced to express the epitope on the cell surface. The induced yeast cells were incubated with varying concentrations of the HCV core chimeric antibody (100 nM, 33 nM, 11 nM, 3.7 nM, 1.2 nM, 0.4 nM, 0.14 nM and zero nM). Bound HCV core chimeric antibody was then detected with goat anti-human IgG conjugated with Alexa 633 fluorophore using standard flow cytometeric analysis. The mean florescence intensity (MFI) at each concentration of the HCV core chimeric antibody was determined after excitation of the fluorophore using a flow cytometer equipped with appropriate lasers and detection optics.

The apparent equilibrium dissociation constant ($K_D$) was calculated by plotting MFI vs. [Ag] and determining a best fit curve, wherein the curve is known to be defined by the formula: Fbkg+Fsat*[Antigen]/($K_D$+[Antigen]), where Fbkg: background signal and Fsat: maxim signal, thereby allowing the determination of $K_D$. The results indicated that the $K_D$ for the HCV core chimeric antibody is about 0.7 nM.

Example 10

Determination of the Equilibrium Dissociation Constant ($K_D$) for HCV NS3 Chimeric Monoclonal Antibody The equilibrium dissociation constant ($K_D$) for the HCV NS3 chimeric antibody was determined as described in Example 9 using yeast cells containing the wildtype HCV 1190-1216 NS3 fragment (from Example 6) and varying concentrations of the HCV NS3 chimeric antibody (33 nM, 11 nM, 3.7 nM, 1.2 nM, 0.4 nM, 0.14 nM, and zero nM). The results indicated that the $K_D$ for the HCV NS3 chimeric antibody is about 68 nM.

Example 11

Determination of Equilibrium Dissociation Constant ($K_D$) for HCV NS4 Chimeric Monoclonal Antibody The equilibrium dissociation constant ($K_D$) for the HCV NS4 chimeric antibody was determined as described in Example 9 using yeast cells containing the wildtype HCV 1692-1713 NS4 fragment (from Example 7) and varying concentrations of the HCV NS4 chimeric antibody (100 nM, 33 nM, 11 nM, 3.7 nM, 1.2 nM, 0.4 nM, 0.14 nM, and zero nM). The results indicated that the $K_D$ for the HCV NS4 chimeric antibody is about 0.5 nM.

Example 12

Determination of Equilibrium Dissociation Constant ($K_D$) for HCV NS5 Chimeric Monoclonal Antibody The equilibrium dissociation constant ($K_D$) for the HCV NS5 chimeric antibody was determined as described in Example 9 using yeast cells containing the wildtype HCV 2382-2408 NS5 fragment (from Example 8) and varying concentration of the HCV NS5 chimeric antibody (100 nM, 33 nM, 11 nM, 3.7 nM, 1.2 nM, 0.4 nM, 0.14 nM, and zero nM). The results indicated that the $K_D$ for the HCV NS5 chimeric antibody is about 8.8 nM.

Example 13

Characterization of HCV Chimeric Antibodies and CHO Lines Secreting Same

The HCV core CHO 201-603-486-333, HCV NS3 CHO 17-903-132sc171, HCV NS4 CHO E99H6C34sc203 and HCV NS5 CHO clone 48-311-271-455 cell lines prepared in Examples 1-4 were analyzed for manufacturability, including cell viability, cell line stability via stable antibody production, and freedom from adventitious agents via mycoplasma testing. The cell lines were also tested for monoclonality. The chimeric antibodies were characterized by isoelectric focusing (IEF), SDS-PAGE and gel permeation chromatography (GPC).

Figure 10:
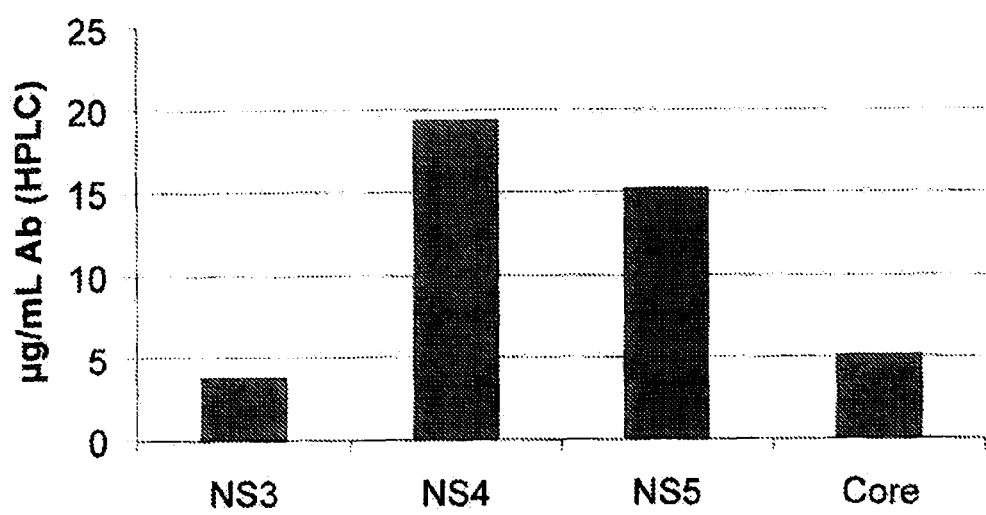
FIG. 10 depicts the average chimeric antibody production on a typical research and development scale (i.e. viable cells were between about 20-10%) as assessed by HPLC analysis of 3 week old cultures for anti-HCV core chimeric antibody ("Core"; HCV core 201-603-486-333); anti-HCV NS3 chimeric antibody ("NS3"; HCV NS3 CHO 17-903-132sc171); anti-HCV NS4 chimeric antibody ("NS4"; HCV NS4 CHO E99H6C34sc203), and anti-HCV NS5 chimeric antibody ("NS5"; HCV NS5 CHO 48-311-271-455).

The results indicated that all the cell lines were >90% clonal and free of adventitious agents. Analysis of chimeric antibody production over a >3 week time period indicated that all cell lines have a stable or increasing chimeric antibody production in culture. The average chimeric antibody production on a terminal R & D scale (i.e. viable cells were between 20-10%) as assessed by HPLC analysis of 3 week old cultures is shown in FIG. 10.

SDS-PAGE gel electrophoresis was performed on all HCV chimeric antibodies under reducing condition. About 3 ug of each chimeric antibody was mixed with loading buffer with reducing agents, boiled for 10 minutes, then loaded onto 12% SDS-PAGE gel and run at 80 Volts for 1.5 hours. The heavy chain should migrate between 66.2 kD and 45 kD, and the light chain should migrate between 31 kD and 21.5 kD. All of the HCV chimeric antibodies showed two distinctive bands by SDS-PAGE that corresponded to antibody heavy and light chains.

In order to further characterize the HCV chimeric antibodies, isoelectric focusing (IEF) gel electrophoresis was performed on all four HCV chimeric antibodies. IEF is a technique that separates proteins according to their net charge. At a given pH, a protein's net charge will depend its relative number of positive and negative charges. The pH at which the positive charges on a protein equal the negative charges defines that protein's isoelectric point (pI). The IEF profiles of the four HCV chimeric antibodies indicated they have pI values ranging from 7.8 to 9.0. Specifically, the pI of the HCV core chimeric antibody was about 9.0, the pI of the HCV NS3 antibody was between 8.5 and 9.0, the pI of the HCV NS4 chimeric antibody was between 7.8 and 8.7, and the pI of the HCV NS5 chimeric antibody was between 8.0 and 8.9.

The HCV core chimeric antibodies were also analyzed by gel permeation high performance liquid chromatography (GPC-HPLC) on a Waters system with a Tosohaas 3000 column. GPC-HPLC is a standard technique used to determine the purity of a protein or polypeptide as well as its aggregation state via chromatographic separation based upon molecular size and shape. Based on three bug injections each of albumin, chimeric antibody and gel filtration standard, the final mean purity for each chimeric antibody lot was calculated. The purity of HCV NS3 CHO 17-903-132sc171 lot was 97%. The purity of HCV NS4 CHO E99H6C34sc203 lot was 58%. The purity of HCV NS5 CHO 48-311-271-455 lot was 90% and the purity of HCV core CHO 201-603-486-333 lot was 88%.

Example 14

Antigen Reactivity of HCV Chimeric Antibodies in Standard HCV Detection Assays

The four chimeric antibodies (HCV core, NS3, NS4 and NS5) prepared as described in Examples 1-4 were tested using Abbott HCV blood screening assays on the Prism, AxSYM, ARCHITECT and EIA (Bead) platforms. The Prism platform assay employs NS3, NS4, NS5 and Core antigens for antibody detection, whereas the AxSYM, ARCHITECT and EIA (Bead) platform assays employ NS3, NS4 and Core antigens for antibody detection. For all platforms, the antigens are currently qualified using epitope reactive plasma/sera samples sourced from human donors.

Abbott HCV EIA is an in vitro enzyme immunoassay for qualitative detection of antibody to Hepatitis C (anti-HCV) in human serum, plasma or cadaveric serum. The human sample is diluted in a specimen diluent and incubated with a polystyrene bead coated with recombinant HCV antigens. If antibody is present in the sample, immunoglobulins in the patient sample bind to the antigens coated on the bead. After removing the unbound materials by washing the bead, human immunoglobulins remaining bound to the bead are detected by incubating the bead-antigen-antibody complex with a solution containing horseradish peroxidase labeled goat antibodies directed against human immunoglobulins using O-phenylenediamine-2HCl (OPD) and reading the intensity of color developed at 492 nm. The final Sample/cutoff (S/Co) are calculated. The cutoff is calculated as follows:

Cutoff value=NCx+(0.25)PCx, where NCx (Negative mean Absorbance)=Total absorbance/number of replicates and PCx (Calculation of positive mean)=Total absorbance/number of replicates.

Samples with absorbance values greater than or equal to 0.005 but less than the cutoff are considered negative. Samples with absorbance values greater than or equal to the cutoff value are considered initially reactive. Following this procedure using the Abbott HCV EIA 2.0 assay kit, the anti-HCV core, NS3 and NS4 chimeric antibodies were all reactive as shown in Table 3. Anti-HCV NS5 chimeric antibody is negative since there is no HCV NS5 recombinant antigen included in the assay.

The Abbott AXSYM Anti-HCV assay is a microparticle immunoassay (META) for the qualitative detection of anti-HCV IgG to HCV recombinant proteins in human serum or plasma. The AxSYM system used to perform the assays calculates the cutoff rate from the mean rate of two Index Calibrator replicates and stores the results. The cutoff rate (CO) is determined by multiplying the AxSYM anti-HCV Index calibrator mean rate by 0.12.

Samples are considered reactive if the S/CO values are greater than or equal to 1.21. Samples with S/CO values between 0.8 and 1.20 are considered to be "greyzone" samples, and samples with S/CO values less than 0.79 are considered non-reactive. Following the protocol described in the Abbott HCV AxSYM Anti-HCV assay package insert, the anti-HCV core, NS3 and NS4 chimeric antibodies were reactive as shown in Table 3. Again, the anti-HCV NS5 chimeric antibody was negative since there is no HCV NS5 recombinant antigen included in the assay.

The Abbott ARCHITECT Anti-HCV assay is a chemiluminescent microparticle immunoassay (CMIA) for the qualitative detection of anti-HCV antibodies in human serum and plasma. The ARCHITECT Anti-HCV assay uses recombinant HCV antigens coated on a microparticle surface to bind antibodies in a sample. In the ARCHITECT Anti-HCV final reaction, bound acridinylated conjugates are used to generate a chemiluminescent signal. The ARCHITECT i System used to perform the assays calculates the cutoff RLU from the mean chemiluminescent signal of three Anti-HCV Calibrator 1 replicates and stores the result. The cutoff RLU is determined by multiplying the Anti-HCV Calibrator 1 mean RLU by 0.074. The ARCHITECT i System then calculates a result based on the ratio of the sample RLU to the cutoff RLU (S/CO) for each specimen and control.

Samples are considered reactive if the S/CO values are greater than or equal to 1.00. Samples with S/CO values between 0.8 and 0.99 are considered to be "greyzone" samples, and samples with S/CO values less than 0.79 are considered non-reactive. Following the protocol provided in the Abbott ARCHITECT Anti-HCV assay package insert, the anti-HCV core, NS3 and NS4 chimeric antibodies are reactive as shown in Table 3. Anti-HCV NS5 chimeric antibody was negative since there is no HCV NS5 recombinant antigen included in the assay.

The Abbott Prism HCV assay is a chemiluminescent microparticle immunoassay for the qualitative detection of anti-HCV antibodies in human serum and plasma. The cutoff value is calculated as follows:

Cutoff value=Mean negative calibrator net counts+
0.55×Mean Positive calibrator net counts.

Samples are considered initially reactive if the S/CO values are greater than or equal to the cutoff value. Following the protocol provided in the Abbott Prism HCV assay package insert, the anti-HCV core, NS3, NS4 and NS5 chimeric antibodies were all reactive as shown in Table 3.

TABLE 3

Reactivity of Core, NS3, NS4 and NS5 Chimeric Antibody in Various Abbott HCV Assays[‡]

| Sample | Antigen Reactivity | Concentration (mg/mL) | Sample/Cutoff (S/CO) values | | | |
|---|---|---|---|---|---|---|
| | | | EIA (Bead) | AxSYM | Prism | ARCHITECT |
| Negative Control | — | — | 0.2 | 0.21 | 0.12 | 0.05 |
| Positive Control[¶] | — | — | 3.21 | 4.99 | 1.60 | 3.63 |
| NS4: 1 | NS4 | 1.41 | 12.72 | 31.11 | 2.58 | 8.59 |
| NS4: 2 | | 1.90 | 15.03 | 26.69 | 2.77 | 5.88 |
| NS4: 3 | | 2.20 | 14.30 | 28.10 | 2.43 | 5.41 |
| NS4: 4 | | 1.50 | 14.00 | 29.68 | 2.94 | 8.89 |
| NS4: 5 | | 0.70 | 13.20 | 31.35 | 2.32 | 7.75 |
| NS4: 6 | | 1.50 | 13.15 | 33.61 | 2.67 | 8.10 |
| NS4: 7 | | 1.19 | 13.24 | 33.29 | 2.66 | 6.34 |
| Core: 1 | Core | 1.13 | 9.04 | 50.89 | 2.14 | 11.81 |
| Core: 2 | | 1.00 | 8.91 | 47.00 | 2.14 | 12.29 |
| Core: 3 | | 0.83 | 9.09 | 46.37 | 2.12 | 14.49 |
| Core: 4 | | 1.80 | 9.27 | 46.74 | 2.08 | 12.20 |
| Core: 5 | | 2.46 | 9.25 | 48.67 | 2.13 | 12.70 |
| CORE: 6 | | 2.50 | 9.45 | 44.70 | 2.16 | 12.36 |
| Core: 7 | | 1.90 | 8.13 | 40.41 | 1.64 | 11.17 |
| Core: 8* | | 0.15 | 9.04 | 45.70 | 1.99 | 11.31 |
| Core: 9 | | 2.14 | 8.85 | 44.76 | 1.92 | 12.03 |
| Core: 10* | | 0.01 | 7.80 | 4.77 | 1.24 | 8.85 |
| NS5: 1 | NS5 | 0.70 | 0.06 | 0.16 | 2.60 | 0.05 |
| NS5: 2 | | 1.60 | 0.03 | 0.14 | 2.04 | 0.06 |
| NS5: 3 | | 1.30 | 0.04 | 0.14 | 2.38 | 0.05 |
| NS5: 4 | | 0.87 | 0.02 | 0.13 | 2.59 | 0.05 |
| NS5: 5 | | 0.58 | 0.02 | 0.10 | 2.55 | 0.05 |
| NS3: 1 | NS3 | 3.08 | 7.44 | 40.58 | 3.94 | 8.75 |
| NS3: 2 | | 2.40 | 7.58 | 40.34 | 4.39 | 9.50 |
| NS3: 3 | | 3.70 | 7.88 | 38.88 | 4.41 | 10.57 |
| NS3: 4 | | 1.90 | 7.51 | 37.54 | 3.89 | 9.69 |
| NS3: 5 | | 2.10 | 7.71 | 37.68 | 4.65 | 10.38 |
| N53: 6[#] | | 1.80 | 6.77 | 36.31 | 4.37 | 8.70 |
| N53: 7[#] | | 1.80 | 7.99 | 39.64 | 4.58 | 9.59 |
| NS3: 8* | | 0.33 | 7.30 | 40.26 | 4.15 | 9.52 |
| NS3: 9* | | 0.34 | 8.00 | 39.42 | 4.30 | 9.61 |

[‡]Chimeric antibodies were tested at a concentration of 500 ng/mL on all Abbott platforms, with the exception of the HCV NS5 chimeric antibody on the Abbott Prism, which was tested at a concentration of 10 µg/mL.
[¶]Positive control consisted of HCV positive patient plasma samples that was qualified and targeted to a specific rate or RLU.
*Harvest samples, i.e. straight cell culture supernatant.
[#]Pre-dialysis samples, i.e. material purified from cell culture supernatant by Protein A purification.

The results show that on the Abbott AxSYM, EIA, Prism and ARCHITECT platforms the HCV chimeric antibodies demonstrate reactivity to antigens that is equal to or greater than the human sourced control. In Table 3, the anti-NS5 chimeric antibody does not react on EIA, AxSYM, and ARCHITECT assay merely because there is no NS5 antigen coated on the bead/microparticle.

Example 15

Preparation of a Human-Mouse Chimeric Antibody Specific for Hepatitis C Virus Core Protein #2

A second anti-core chimeric antibody, HCV Core CHO 14-153-229sc152, was prepared from the hybridoma 14-153-462. The hybridoma cell line anti-HCV Core 14-153-462 was deposited with the American Type Culture Collection (ATCC) at 10801 University Boulevard, Manassas, Va. on Nov. 21, 2006 under Accession No. PTA-8028.

Preparation of a Hybridoma Cell Line

The hybridoma cell line anti-HCV core 14-153-462 was developed as described in Example 1 using the purified HCV recombinant core antigen known as pL-Core in place of the core CKS-33C-BCD antigen. The pL-CORE recombinant antigen corresponds to amino acids 1-150 of the HCV polyprotein. The animal immunization regiment utilized one 200 µg boost in the Freunds Adjuvant System, with a pre-fusion boost in saline 2 weeks later.

Isolation of mRNA and Identification of Mouse $V_H$ and $V_L$ Sequences mRNA was isolated from the hybridoma cell line anti-HCV core 14-153-462 and the mouse $V_H$ and $V_L$ sequences obtained by RT-PCR as described in Example 1 with respect to the HCV Core 201-603-195 hybridoma cell line. Positive PCR products were observed from the heavy chain (H) primer sets of C (VH-C) and from the light chain (L) primer sets of B and C (VL-B, VL-C). All positive PCR products were gel purified, cloned into the pCR TOPO 2.1 TA vector and transformed into *E. coli*. Colony PCR reactions were used to confirm the clone insert. Briefly, the PCR was conducted using M13 forward and M13 reverse primer (Invitrogen), Taq DNA polymerase and boiled *E. coli* colony as the template. The PCR comprised denaturation 1 minute at 94° C.; annealing 1 minute at 50° C. and extension 2 minutes at 72° C., with a final extension 6 minutes at 72° C. for a total of 30 cycles. The clones giving the correct size for the PCR products were grown in LB broth. Each plasmid DNA was purified using QIAprep spin miniprep Kit (QIAGEN) and sequenced using M13 forward and reverse primers with the Big Dye Terminator v3.1 cycle sequencing kit (Applied Biosystems).

The final TA clone was selected by sequence alignment as described in Example 1. The sequence results confirmed that the VL-B clone contained the correct $V_L$ sequence (SEQ ID NO:41 encoding a polypeptide as shown in SEQ ID NO:39), while the VH-C clones contained the correct $V_H$ sequence (SEQ ID NO:40 encoding a polypeptide as shown in SEQ ID NO:38) (see also FIGS. 11A-D).

Cloning the $V_H$ and $V_L$ Genes into pBOS Vectors

Using the VL-B TA clone number 5 as the template, a pair of PCR primers were designed to clone out the mouse $V_L$ sequence, namely, a HCV core Antibody $V_L$ 5'-end primer 5'-AAATTTTCGCGATGCGACATTGTGCT-GACCCAATCTC-3' [SEQ ID NO:96], and a HCV core Antibody $V_L$ 3'-end primer

5'-ACTACTCGTACGTTTGATTTCCAGCTTG-GTGCCT-3' [SEQ ID NO:97].

The 5'-end primer contained a partial Kappa signal sequence and a Nru I restriction site and the 3'-end primer contained a BsiW I restriction site. In addition, using the VH TA clone number 1 as the template, a pair of primers was designed to clone out the mouse $V_H$ sequence, namely, a HCV core Antibody $V_H$ 5'-end primer 5'-AAATTTTCGCGATTTTAAAAGGTGTC-CAGTGTCAGATCCA
GTTGGTGCAGTCTGG-3' [SEQ ID NO:98], and a HCV core Antibody $V_H$ 3'-end primer

5'-TCCTTTGTCGACGCTGAGGAGACGGT-GACTGAGGTT-3' [SEQ ID NO:99].

For this pair of primers, the 5'-end primer contained a partial heavy chain signal sequence and an Nru I restriction site and the 3'-end primer contained a Sal I restriction site.

The $V_L$ and $V_H$ sequences were independently amplified by PCR using the above primer pairs and the VL-B TA clone number 5 and VH-C TA clone number 1, respectively, as the templates. The PCR was executed in 1×PCR amplification Buffer using 20 pmol each of the 5'-end and 3'-end primers, 1 unit of Taq DNA polymerase (Invitrogen), and 2 µl of bacterial colony as the template. The PCR was performed employing 30 cycles of 30 seconds at 94° C. and 30 seconds at 55° C. followed by 1 minute at 72° C.

The $V_L$ and $V_H$ PCR products were restriction enzyme trimmed by Nru I/BsiW I and Nri I/Sal I digestion, respectively, and then cloned into either the pBOS-hck vector (for the $V_L$ sequence) or the pBOS-hcg vector (for the $V_H$ sequence), as described in Example 1. Plasmids pBOS 14-153-462-L (containing the $V_L$ sequence) and pBOS 14-153-462-H (containing the $V_H$ sequence) were selected by sequencing as described in Example 1. Once the respective pBOS clones were identified, separate *E. coli* DH5α cell banks containing either the pBOS 14-153-462-L-T0 plasmid or the pBOS 14-153-462-H-T0 plasmid were made to preserve the pBOS clones.

Chimeric Antibody Functional Testing pBOS 14-153-462-L-T0 and pBOS 14-153-462-H-T0 plasmid DNA was prepared and transiently transfected into COS 7L cells as described in Example 1. The anti-HCV core chimeric antibody was prepared from the transfected COS 7L cells as described in Example 1 and assayed by EIA to confirm reactivity with HCV core antigen. The EIA was conducted as described in Example 1. The EIA results demonstrated that the chimeric antibody from transient expression was reactive to the HCV core antigen.

Cloning the $V_H$ and $V_L$ Sequences into a Stable Expression Vector

Figure 12:
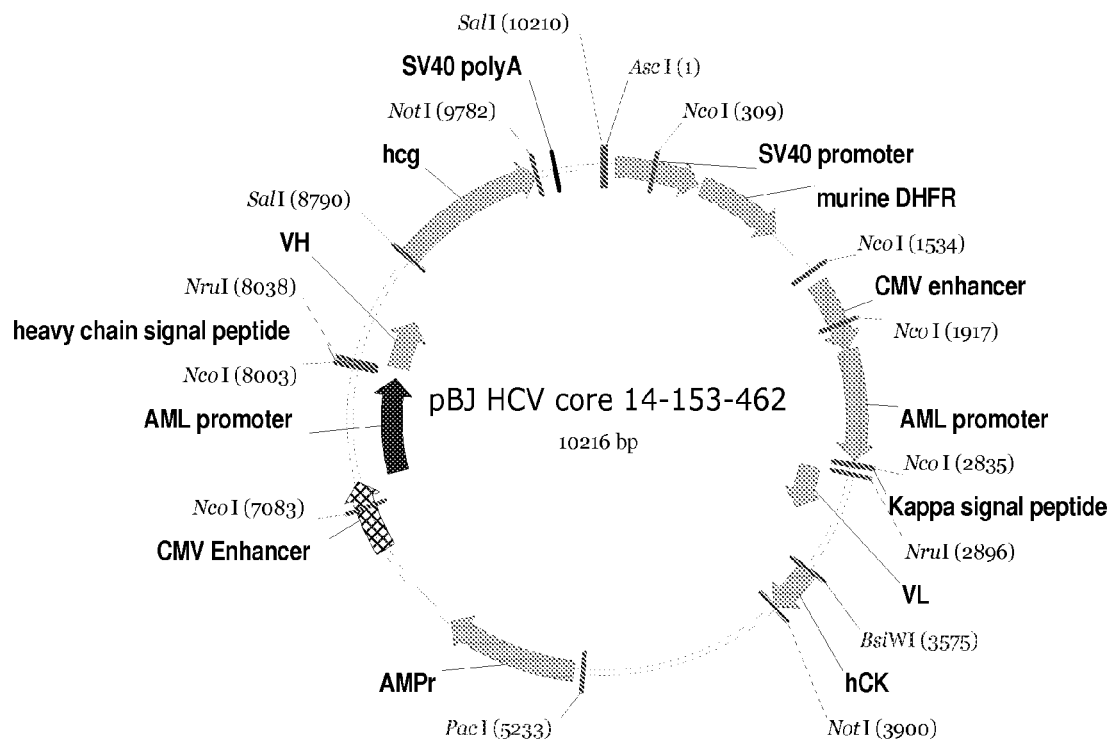
FIG. 12 presents a plasmid map of an expression plasmid used in the preparation of an anti-HCV core chimeric antibody (HCV Core 14-153-229sc152) in one embodiment of the present invention.

The pBOS 14-153-462-L-T0 and pBOS 14-153-462-H-T0 clones were used to construct a plasmid clone for stable cell line transfection by first cloning the sequences into the pBV vector (for the $V_H$ sequence) or the pJV vector (for the $V_L$ sequence) and subsequently ligating together the vector fragments obtained from Pac I/Asc I restriction enzyme digestion as described in Example 1 to provide the pBJ plasmid pBJ HCV core 14-153-462 that contains both the $V_H$ and the $V_L$ sequences. The pBJ clone was screened by Srf I/Not I digestion to confirm that it contains both sequences. The plasmid map for the final pBJ clone (pBJ HCV core 14-153-462) for the HCV core chimeric antibody is shown in FIG. 12. The $V_H$ and $V_L$ gene sequences are shown in FIGS. 11A-B (SEQ ID NO:40 and SEQ ID NO:41, respectively). *E. coli* DH5α cell banks containing the pBJ 14-153-462-T4 clone were made.

Establishing a Stable CHO Cell Line and Expression of the HCV Chimeric Antibody

The pBJ 14-153-462-T4 plasmid was transfected by calcium phosphate mediated transfection into the DHFR-deficient Chinese Hamster Ovary cell line as described in Example 1. Culture and single cell cloning was conducted as described in Example 1. The 96 well plates were tested by antigen specific EIA and clone number 229 was selected for further development. The EIA was conducted as described above. The HCV core 14-153-462 CHO cell clone was cultured and single cell sorted into 96-well plates using the BD FACSAria flow cytometer sorter. CHO subclone number 152 was selected for weaning into CD-CHO serum free medium (Invitrogen). The final CHO cell line (HCV core 14-153-229sc152) was expanded for production of the chimeric antibody and for development of a discovery cell bank for storage in liquid nitrogen. The chimeric antibody was purified from this cell line using standard Protein A purification procedures as described in Example 1.

The HCV core CHO 14-153-229sc152 cell line was deposited with the American Type Culture Collection (ATCC) at 10801 University Boulevard, Manassas, Va. on May 2, 2006 under Patent Deposit Designation PTA-7571.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

What is claimed is:

1. An immunodiagnostic reagent comprising one or more recombinant antibodies that specifically bind to a diagnostically relevant region of a hepatitis C virus (HCV) protein, wherein said one or more recombinant antibodies comprises a $V_H$ region and $V_L$ regions selected from the group consisting of:
   (a) a $V_H$ region comprising the amino acid sequence of SEQ ID NO:9 and a $V_L$ region comprising the amino acid sequence of SEQ ID NO:10; and
   (b) a $V_H$ region comprising, in order, (i) the complementarity determining region (CDR) of SEQ ID NO:54, (ii) the CDR of SEQ ID NO:55, and (iii) the CDR of SEQ ID NO:56 and a $V_L$ region comprising, in order, (i) the CDR of SEQ ID NO:57, (ii) the CDR of SEQ ID NO:58, and (iii) the CDR of SEQ ID NO:59.

2. The immunodiagnostic reagent according to claim 1, wherein said immunodiagnostic reagent is a reagent selected from the group consisting of a detection reagent, a standardization reagent, and a positive control reagent.

3. A chimeric antibody which specifically binds to a diagnostically relevant region of a HCV NS3 protein, wherein said chimeric antibody comprises a $V_H$ region and $V_L$ regions selected from the group consisting of:
   (a) a $V_H$ region comprising the amino acid sequence of SEQ ID NO:9 and a $V_L$ region comprising the amino acid sequence of SEQ ID NO:10; and
   (b) a $V_H$ region comprising, in order, (i) the complementarity determining region (CDR) of SEQ ID NO:54, (ii) the CDR of SEQ ID NO:55, and (iii) the CDR of SEQ ID NO:56 and $V_L$ region comprising, in order, (i) the CDR of SEQ ID NO:57, (ii) the CDR of SEQ ID NO:58, and (iii) the CDR of SEQ ID NO:59.

4. A chimeric antibody expressed by the cell line HCV NS3 CHO 17-903-132sc171 having A.T.C.C. Deposit No. PTA-7573.

5. A mouse monoclonal antibody expressed by the cell line anti-HCV NS3 17-903-127 having A.T.C.C. Deposit No. PTA-8023.

6. A cell line which expresses a chimeric antibody that specifically binds to a diagnostically relevant region of a hepatitis C virus protein, wherein said cell line is anti-HCV NS3CHO 17-903-132sc171 having A.T.C.C Deposit No. PTA-7573.

7. A cell line which expresses a mouse monoclonal antibody that specifically binds to a diagnostically relevant region of a hepatitis C virus protein, wherein said cell line is anti-HCV NS3 17-903-127 having A.T.C.C. Deposit No. PTA-8023.

8. A diagnostic kit for the detection of hepatitis C virus comprising the immunodiagnostic reagent of claim 1.

9. An immunodiagnostic reagent comprising one chimeric antibody, wherein said chimeric antibody comprises a $V_H$ region and $V_L$ regions selected from the group consisting of:
   (a) a $V_H$ region comprising the amino acid sequence encoded by SEQ ID NO:15 and a $V_L$ region comprising the amino acid sequence encoded by SEQ ID NO:16; and
   (b) a $V_H$ region comprising, in order, (i) the CDR encoded by SEQ ID NO:81, (ii) the CDR encoded by SEQ ID NO:82, and (iii) the CDR encoded by SEQ ID NO:83 and a $V_L$ region comprising, in order, (i) the CDR encoded by SEQ ID NO:84, (ii) the CDR encoded by SEQ ID NO:85, and (iii) the CDR encoded by SEQ ID NO:86.

10. An chimeric antibody comprising a $V_H$ region and $V_L$ regions selected from the group consisting of:
    (a) a $V_H$ region comprising the amin acid sequence by SEQ ID NO:15 and a $V_L$ region comprising the amino acid sequence encoded by SEQ ID NO:16; and
    (b) a $V_H$ region comprising, in order, (i) the CDR encoded by SEQ ID NO:81, (ii) the CDR encoded by SEQ ID NO:82, and (iii) the CDR encoded by SEQ ID NO:83 and a $V_L$ region comprising, in order, (i) the CDR encoded by SEQ ID NO:84, (ii) the CDR encoded by SEQ ID NO:85, and (iii) the CDR encoded by SEQ ID NO:86.

11. An isolated polypeptide, wherein said polypeptide comprises a portion of a chimeric antibody that specifically binds to a diagnostically relevant region of a HCV NS3 protein, wherein said polypeptide comprises a $V_H$ region and $V_L$ regions selected from the group consisting of:
    (a) a $V_H$ region comprising the amino acid sequence of SEQ ID NO:9 and a $V_L$ region comprising the amino acid sequence of SEQ ID NO:10; and
    (b) a $V_H$ region comprising, (i) the CDR encoded by SEQ ID NO:54 as CDR1, (ii) the CDR encoded by SEQ ID NO:55 as CDR2, and (iii) the CDR encoded by SEQ ID NO:56 as CDR3 and a $V_L$ region comprising, (i) the CDR of SEQ ID NO:57 as CDR1, (ii) the CDR of SEQ ID NO:58 as CDR2, and (iii) the CDR of SEQ ID NO:59 as CDR3.

* * * * *

SEQUENCE LISTING

<160> NUMBER OF SEQ ID NOS: 111

<210> SEQ ID NO 1
<211> LENGTH: 120
<212> TYPE: PRT
<213> ORGANISM: Artificial Sequence
<220> FEATURE:
<223> OTHER INFORMATION: HCV Core 201-603 Antibody VH Region

<400> SEQUENCE: 1

```
Gln Ile Gln Leu Val Gln Ser Gly Pro Glu Leu Gln Lys Pro Gly Lys
  1               5                  10                  15

Thr Val Lys Ile Ser Cys Lys Thr Ser Gly Tyr Thr Phe Thr Asp Tyr
             20                  25                  30

Pro Met His Trp Val Lys Gln Ala Pro Gly Lys Gly Leu Lys Trp Met
         35                  40                  45

Gly Trp Ile Asn Thr Glu Thr Gly Glu Pro Thr Arg Val Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asp Glu Asp Thr Ala Thr Tyr Phe Cys
                 85                  90                  95

Ala Arg Gly Gly Gly Val Arg Arg Gln Val Met Asp Tyr Trp Gly Gln
            100                 105                 110

Gly Thr Ser Val Thr Val Ser Ser
        115                 120
```

<210> SEQ ID NO 2
<211> LENGTH: 113
<212> TYPE: PRT
<213> ORGANISM: Artificial Sequence
<220> FEATURE:
<223> OTHER INFORMATION: HCV Core 201-603 Antibody VL Region

<400> SEQUENCE: 2

```
Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Leu Asn Ser
             20                  25                  30

Arg Thr Arg Lys Asn Tyr Leu Val Trp Tyr Gln Gln Lys Pro Gly Gln
         35                  40                  45

Ser Pro Lys Leu Leu Ile Tyr Trp Ala Ser Thr Arg Asp Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Tyr Thr Phe Gly Gly Gly Thr Lys Leu Glu Ile Lys
            100                 105                 110

Arg
```

<210> SEQ ID NO 3
<211> LENGTH: 32
<212> TYPE: DNA
<213> ORGANISM: Artificial Sequence
<220> FEATURE:
<223> OTHER INFORMATION: HCV Core 201-603 Antibody VL 5' Primer

<400> SEQUENCE: 3

```
gctcgcgatg cgacattgtg atgtcacagt ct                              32
```

<210> SEQ ID NO 4
<211> LENGTH: 27
<212> TYPE: DNA
<213> ORGANISM: Artificial Sequence
<220> FEATURE:
<223> OTHER INFORMATION: HCV Core 201-603 Antibody VL 3' Primer

<400> SEQUENCE: 4

```
caccgtacgt tttatttcca gcttggt                                    27
```

<210> SEQ ID NO 5
<211> LENGTH: 56
<212> TYPE: DNA
<213> ORGANISM: Artificial Sequence
<220> FEATURE:
<223> OTHER INFORMATION: HCV Core 201-603 Antibody VH 5' Primer

<400> SEQUENCE: 5

```
ttgtcgcgat tttaaaaggt gtccagtgcc agatccagtt ggtgcagtct ggacct    56
```

<210> SEQ ID NO 6
<211> LENGTH: 33
<212> TYPE: DNA
<213> ORGANISM: Artificial Sequence
<220> FEATURE:
<223> OTHER INFORMATION: HCV Core 201-603 Antibody VH 3' Primer

<400> SEQUENCE: 6

```
ttggtcgacg ctgaggagac ggtgactgag gtt                             33
```

<210> SEQ ID NO 7
<211> LENGTH: 360
<212> TYPE: DNA
<213> ORGANISM: Artificial Sequence
<220> FEATURE:
<223> OTHER INFORMATION: Sequence encoding HCV Core 201-603 Antibody VH
      Region

<400> SEQUENCE: 7

```
cagatccagt tggtgcagtc tggacctgag ctgcagaagc ctggaaagac agtcaagatc    60
tcctgcaaga cttctggtta taccttcaca gactatccaa tgcactgggt gaagcaggct   120
ccaggaaagg gtttaaagtg gatgggctgg ataaacactg agactggtga gccaacacgt   180
gtagatgact tcaagggacg ttttgccttc tctttggaaa cctctgccag cactgcctat   240
ttgcagatca acaacctcaa agatgaggac acggccacat atttctgcgc tagaggggt   300 ggggtccgac gccaggttat ggactactgg ggtcaaggaa cctcagtcac cgtctcctca   360
```

<210> SEQ ID NO 8
<211> LENGTH: 337
<212> TYPE: DNA
<213> ORGANISM: Artificial Sequence
<220> FEATURE:
<223> OTHER INFORMATION: Sequence encoding HCV Core 201-603 Antibody VL
      Region

<400> SEQUENCE: 8

```
gacattgtga tgtcacagtc tccatcctcc ctggctgtgt cagcaggaga gaaggtcact    60
atgagctgca aatccagtca gagtctgctc aatagtagaa cccgaaagaa ctacttggtt   120
tggtaccagc agaaaccagg gcagtctcct aaactgctga tctactgggc atccactagg   180
gattctgggg tccctgatcg cttcacaggc agtggatctg ggacagattt cactctcacc   240
```

```
atcagcagtg tgcaggctga agacctggca gtttattact gcaagcaatc ttataatctg    300
tacacgttcg gaggggggac caagctggaa ataaaac                              337
```

```
<210> SEQ ID NO 9
<211> LENGTH: 117
<212> TYPE: PRT
<213> ORGANISM: Artificial Sequence
<220> FEATURE:
<223> OTHER INFORMATION: HCV NS3 Antibody VH Region

<400> SEQUENCE: 9
```

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Ala
        35                  40                  45

Ala Tyr Ile Ser Asn Gly Ala Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Leu Trp Asp Gly Leu Asp Tyr Trp Gly Gln Gly Thr Thr
            100                 105                 110

Leu Thr Val Ser Ser
        115

```
<210> SEQ ID NO 10
<211> LENGTH: 113
<212> TYPE: PRT
<213> ORGANISM: Artificial Sequence
<220> FEATURE:
<223> OTHER INFORMATION: HCV NS3 Antibody VL Region

<400> SEQUENCE: 10
```

Asp Val Val Met Ala Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg

```
<210> SEQ ID NO 11
<211> LENGTH: 56
<212> TYPE: DNA
<213> ORGANISM: Artificial Sequence
<220> FEATURE:
<223> OTHER INFORMATION: HCV NS3 Antibody VL 5' Primer
```

<400> SEQUENCE: 11
ctgtggttcc ccggctcgcg atgcgatgtt gtgatggccc aaactccact ctcccc    56

<210> SEQ ID NO 12
<211> LENGTH: 40
<212> TYPE: DNA
<213> ORGANISM: Artificial Sequence
<220> FEATURE:
<223> OTHER INFORMATION: HCV NS3 Antibody VL 3' Primer

<400> SEQUENCE: 12
gcgcatgcgt cgtacgtttt atttccagct tggtccccc    40

<210> SEQ ID NO 13
<211> LENGTH: 68
<212> TYPE: DNA
<213> ORGANISM: Artificial Sequence
<220> FEATURE:
<223> OTHER INFORMATION: HCV NS3 Antibody VH 5' Primer

<400> SEQUENCE: 13 ggcttttttct tgtcgcgatt ttaaaaggtg tccagtgcga agtgaagctg gtggagtctg    60
ggggaggc    68

<210> SEQ ID NO 14
<211> LENGTH: 53
<212> TYPE: DNA
<213> ORGANISM: Artificial Sequence
<220> FEATURE:
<223> OTHER INFORMATION: HCV NS3 Antibody VH 3' Primer

<400> SEQUENCE: 14
gcgcatgcat gcattgtcga cgcgaggaga ctgtgagagt ggtgccttgg ccc    53

<210> SEQ ID NO 15
<211> LENGTH: 351
<212> TYPE: DNA
<213> ORGANISM: Artificial Sequence
<220> FEATURE:
<223> OTHER INFORMATION: Sequence encoding HCV NS3 Antibody VH Region

<400> SEQUENCE: 15
gaagtgaagc tggtggagtc tgggggaggc ttagtgcagc ctggagggtc cctgaaactc    60
tcctgtgcaa cctctggatt cactttcagt gactattata tgtattgggt tcgccagact    120
ccagagaaga ggctggagtg ggccgcatac attagtaatg gtgctggtag cacctattat    180
ccagacactg taaagggccg attcaccatc tccagagaca atgccaagaa caccctgtac    240
ctgcaaatga gccgtctgaa gtctgaggac acagccatgt attactgtgc aagaggcctc    300
tgggacggcc ttgactactg ggccaaggc accactctca cagtctcctc g    351

<210> SEQ ID NO 16
<211> LENGTH: 339
<212> TYPE: DNA
<213> ORGANISM: Artificial Sequence
<220> FEATURE:
<223> OTHER INFORMATION: Sequence encoding HCV NS3 Antibody VL Region

<400> SEQUENCE: 16
gatgttgtga tggcccaaac tccactctcc ctgcctgtca gtcttggaga tcaagcctcc    60
atctcttgca gatctagtca gagccttgta cacagtaatg gaaacaccta tttacattgg    120
tacctgcaga ggccaggcca gtctccaaag ctcctgatct acaaagtttc caaccgattt    180

```
tctggggtcc cagacaggtt cagtggcagt ggatcaggga cagatttcac actcaagatc    240
agcagagtgg aggctgagga tctgggagtt tatttctgct ctcaaagtac acatgttccg    300
tacacgttcg gaggggggac caagctggaa ataaaacgt                           339
```

<210> SEQ ID NO 17
<211> LENGTH: 114
<212> TYPE: PRT
<213> ORGANISM: Artificial Sequence
<220> FEATURE:
<223> OTHER INFORMATION: HCV NS4 Antibody VH Region

<400> SEQUENCE: 17

```
Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Asp Tyr
             20                  25                  30

Ser Met His Trp Val Asn Gln Ala Pro Gly Lys Gly Leu Lys Trp Met
         35                  40                  45

Gly Trp Ile Asn Thr Glu Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Thr Arg Gly Gly Thr Gly Tyr Trp Gly Gln Gly Thr Thr Leu Thr Val
            100                 105                 110

Ser Ser
```

<210> SEQ ID NO 18
<211> LENGTH: 113
<212> TYPE: PRT
<213> ORGANISM: Artificial Sequence
<220> FEATURE:
<223> OTHER INFORMATION: HCV NS4 Antibody VL Region

<400> SEQUENCE: 18

```
Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val Tyr Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
            100                 105                 110

Arg
```

<210> SEQ ID NO 19
<211> LENGTH: 31
<212> TYPE: DNA
<213> ORGANISM: Artificial Sequence
<220> FEATURE:
<223> OTHER INFORMATION: HCV NS4 Antibody VL 5' Primer

```
<400> SEQUENCE: 19
gctcgcgatg cgatgttgtg atgacccaaa c                                    31

<210> SEQ ID NO 20
<211> LENGTH: 29
<212> TYPE: DNA
<213> ORGANISM: Artificial Sequence
<220> FEATURE:
<223> OTHER INFORMATION: HCV NS4 Antibody VL 3' Primer

<400> SEQUENCE: 20
caccgtacgt ttgatttcca gcttggtgc                                        29

<210> SEQ ID NO 21
<211> LENGTH: 30
<212> TYPE: DNA
<213> ORGANISM: Artificial Sequence
<220> FEATURE:
<223> OTHER INFORMATION: HCV NS4 Antibody VH 5' Primer

<400> SEQUENCE: 21
tacttcgcga cagatccagt tggtgcagtc                                       30

<210> SEQ ID NO 22
<211> LENGTH: 31
<212> TYPE: DNA
<213> ORGANISM: Artificial Sequence
<220> FEATURE:
<223> OTHER INFORMATION: HCV NS4 Antibody VH 3' Primer

<400> SEQUENCE: 22
tggtcgacgc tgaggagact gtgagagtgg t                                    31

<210> SEQ ID NO 23
<211> LENGTH: 342
<212> TYPE: DNA
<213> ORGANISM: Artificial Sequence
<220> FEATURE:
<223> OTHER INFORMATION: Sequence encoding HCV NS4 Antibody VH Region

<400> SEQUENCE: 23
cagatccagt tggtgcagtc tggacctgag ctgaagaagc ctggagagac agtcaagatc      60
tcctgcaagg cttctggtta taccttcaca gactattcaa tgcactgggt gaaccaggct    120
ccaggaaagg gtttaaagtg gatgggctgg ataaacactg agactggtga gccaacatat    180
gcagatgact caagggacg gtttgccttc tctttggaaa cctctgccag cactgcctat    240
ttgcagatca caacctcaa aaatgaggac acggctacat atttctgtac taggggaggc    300
acgggctact ggggccaagg caccactctc acagtctcct ca                       342

<210> SEQ ID NO 24
<211> LENGTH: 339
<212> TYPE: DNA
<213> ORGANISM: Artificial Sequence
<220> FEATURE:
<223> OTHER INFORMATION: Sequence encoding HCV NS4 Antibody VL Region

<400> SEQUENCE: 24
gatgttgtga tgacccaaac tccactctcc ctgcctgtca gtcttggaga tcaagcctcc     60
atctcttgca gatctagtca gagccttgta tacagtaatg aaacaccta tttacattgg    120 tacctgcaga agccaggcca gtctccaaag ctcctgatct acaaagtttc caaccgattt    180
tctggggtcc cagacaggtt cagtggcagt ggatcaggga cagatttcac actcaagatc    240
```

```
agcagagtgg aggctgagga tctgggagtt tatttctgct ctcaaagtac acatgttccg    300
tggacgttcg gtggaggcac caagctggaa atcaaacgg                            339
```

<210> SEQ ID NO 25
<211> LENGTH: 115
<212> TYPE: PRT
<213> ORGANISM: Artificial Sequence
<220> FEATURE:
<223> OTHER INFORMATION: HCV NS5 Antibody VH Region

<400> SEQUENCE: 25

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Arg Glu Phe Ala Tyr Trp Gly Gln Gly Thr Leu Val Thr
            100                 105                 110

Val Ser Ala
        115

<210> SEQ ID NO 26
<211> LENGTH: 114
<212> TYPE: PRT
<213> ORGANISM: Artificial Sequence
<220> FEATURE:
<223> OTHER INFORMATION: HCV NS5 Antibody VL Region

<400> SEQUENCE: 26

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Arg

<210> SEQ ID NO 27
<211> LENGTH: 30
<212> TYPE: DNA
<213> ORGANISM: Artificial Sequence
<220> FEATURE:
<223> OTHER INFORMATION: HCV NS5 Antibody VL 5' Primer

<400> SEQUENCE: 27

```
gctcgcgatg cgacattgtg atgtcacagt                                       30
```

<210> SEQ ID NO 28
<211> LENGTH: 27
<212> TYPE: DNA
<213> ORGANISM: Artificial Sequence
<220> FEATURE:
<223> OTHER INFORMATION: HCV NS5 Antibody VL 3' Primer

<400> SEQUENCE: 28

```
caccgtacgt tcagctcca gcttggt                                           27
```

<210> SEQ ID NO 29
<211> LENGTH: 29
<212> TYPE: DNA
<213> ORGANISM: Artificial Sequence
<220> FEATURE:
<223> OTHER INFORMATION: HCV NS5 Antibody VH 5' Primer

<400> SEQUENCE: 29

```
tacttcgcga gaggttcagc tgcagcagt                                        29
```

<210> SEQ ID NO 30
<211> LENGTH: 28
<212> TYPE: DNA
<213> ORGANISM: Artificial Sequence
<220> FEATURE:
<223> OTHER INFORMATION: HCV NS5 Antibody VH 3' Primer

<400> SEQUENCE: 30

```
tggtcgacgc tgcagagaca gtgaccag                                         28
```

<210> SEQ ID NO 31
<211> LENGTH: 345
<212> TYPE: DNA
<213> ORGANISM: Artificial Sequence
<220> FEATURE:
<223> OTHER INFORMATION: Sequence encoding HCV NS5 Antibody VH Region

<400> SEQUENCE: 31
gaggttcagc tgcagcagtc tggggcagag cttgtgaagc caggggcctc agtcaagttg 60
tcctgcacag cttctggctt caacattaaa gacacctata tgcactgggt gaagcagagg 120
cctgaacagg gcctggagtg gattggaagg attgatcctg cgaatggtaa tactaaatat 180
gacccgaagt tccagggcaa ggccactata acagcagaca catcctccaa cacagcctac 240
ctgcagctca gcagcctgac atctgaggac actgccgtct attactgtgc tagatcgcgg 300
gagtttgctt actggggcca agggactctg gtcactgtct ctgca 345

<210> SEQ ID NO 32
<211> LENGTH: 342
<212> TYPE: DNA
<213> ORGANISM: Artificial Sequence
<220> FEATURE:
<223> OTHER INFORMATION: Sequence encoding HCV NS5 Antibody VL Region

<400> SEQUENCE: 32
gacattgtga tgtcacagtc tccatcctcc ctagctgtgt cagttggaga gaaggttact 60
atgagctgca agtccagtca gagcctttta tatagtagca atcaaaagaa ctacttggcc 120
tggtaccagc agaaaccagg gcagtctcct aaactgctga tttactgggc atccactagg 180
gaatctgggg tccctgatcg cttcacaggc agtggatctg ggacagattt cactctcacc 240
atcagcagtg tgaaggctga agacctggca gtttattact gtcagcaata ttatagctat 300

```
ccgctcacgt tcggtgctgg gaccaagctg gagctgaaac gg              342
```

<210> SEQ ID NO 33
<211> LENGTH: 5
<212> TYPE: PRT
<213> ORGANISM: Artificial Sequence
<220> FEATURE:
<223> OTHER INFORMATION: HCV Core Antigenic Fragment

<400> SEQUENCE: 33

Gly Gly Val Tyr Leu
1               5

<210> SEQ ID NO 34
<211> LENGTH: 13
<212> TYPE: PRT
<213> ORGANISM: Artificial Sequence
<220> FEATURE:
<223> OTHER INFORMATION: HCV Core Antigenic Fragment

<400> SEQUENCE: 34

Gly Gly Gln Ile Val Gly Gly Val Tyr Leu Leu Pro Arg
1               5                   10

<210> SEQ ID NO 35
<211> LENGTH: 27
<212> TYPE: PRT
<213> ORGANISM: Artificial Sequence
<220> FEATURE:
<223> OTHER INFORMATION: HCV NS3 Antigenic Fragment

<400> SEQUENCE: 35

Ala Lys Ala Val Asp Phe Val Pro Val Glu Ser Leu Glu Thr Thr Met
1               5                   10                  15

Arg Ser Pro Val Phe Thr Asp Asn Ser Ser Pro
            20                  25

<210> SEQ ID NO 36
<211> LENGTH: 22
<212> TYPE: PRT
<213> ORGANISM: Artificial Sequence
<220> FEATURE:
<223> OTHER INFORMATION: HCV NS4 Antigenic Fragment

<400> SEQUENCE: 36

Pro Ala Ile Ile Pro Asp Arg Glu Val Leu Tyr Arg Glu Phe Asp Glu
1               5                   10                  15

Met Glu Glu Cys Ser Gln
            20

<210> SEQ ID NO 37
<211> LENGTH: 27
<212> TYPE: PRT
<213> ORGANISM: Artificial Sequence
<220> FEATURE:
<223> OTHER INFORMATION: HCV NS5 Antigenic Fragment

<400> SEQUENCE: 37

Ala Glu Ser Tyr Ser Ser Met Pro Pro Leu Glu Gly Glu Pro Gly Asp
1               5                   10                  15

Pro Asp Leu Ser Asp Gly Ser Trp Ser Thr Val
            20                  25

<210> SEQ ID NO 38
<211> LENGTH: 125

<212> TYPE: PRT
<213> ORGANISM: Artificial Sequence
<220> FEATURE:
<223> OTHER INFORMATION: HCV Core 14-153 Antibody VH Region

<400> SEQUENCE: 38

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ile Thr Ala Tyr
65                  70                  75                  80

Leu Gln Ile Asn Asn Leu Lys Asn Glu Asp Thr Ala Thr Tyr Phe Cys
                85                  90                  95

Ala Arg Ala Gly Gly Asp Tyr Tyr Asp Ser Ser Tyr Asp Tyr Ala Met
            100                 105                 110

Asp Tyr Trp Gly Gln Gly Thr Ser Val Thr Val Ser Ser
        115                 120                 125

<210> SEQ ID NO 39
<211> LENGTH: 112
<212> TYPE: PRT
<213> ORGANISM: Artificial Sequence
<220> FEATURE:
<223> OTHER INFORMATION: HCV Core 14-153 Antibody VL Region

<400> SEQUENCE: 39

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

<210> SEQ ID NO 40
<211> LENGTH: 375
<212> TYPE: DNA
<213> ORGANISM: Artificial Sequence
<220> FEATURE:
<223> OTHER INFORMATION: Sequence encoding HCV Core 14-153 Antibody VH
      Region

<400> SEQUENCE: 40
cagatccagt tggtgcagtc tggacctgag ctgaagaagc tggagagaca gtcaagatc      60 tcctgcaagg cttctgggta taccttcaca aactatggaa tgaactgggt gaagcaagct    120
ccaggaaagg gtttaaagtg gatgggctgg ataaacacca acactggaga gccaacatat    180
gctgaagagt tcaagggacg gtttgccttc tctttggaaa cctctgccat cactgcctat    240

```
ttgcagatca acaacctcaa aaatgaggac acggctacat atttctgtgc aagagcgggg    300
ggagattact acgatagtag ctacgactat gctatggact actggggtca aggaacctca    360
gtcaccgtct cctca                                                     375
```

<210> SEQ ID NO 41
<211> LENGTH: 336
<212> TYPE: DNA
<213> ORGANISM: Artificial Sequence
<220> FEATURE:
<223> OTHER INFORMATION: Sequence encoding HCV Core 14-153 Antibody VL
      Region

<400> SEQUENCE: 41

```
gacattgtgc tgacccaatc cccagcttct ttggctgtgt ctctagggca gagggccacc     60
atctcctgca aggccagcca agtgttgat tatgatggtg atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccgtgg    300
acgttcggtg gaggcaccaa gctggaaatc aaacgt                              336
```

<210> SEQ ID NO 42
<211> LENGTH: 8
<212> TYPE: PRT
<213> ORGANISM: Artificial Sequence
<220> FEATURE:
<223> OTHER INFORMATION: HCV Core Antibody VH Region CDR1

<400> SEQUENCE: 42

Gly Tyr Thr Phe Thr Asp Tyr Pro
  1               5

<210> SEQ ID NO 43
<211> LENGTH: 8
<212> TYPE: PRT
<213> ORGANISM: Artificial Sequence
<220> FEATURE:
<223> OTHER INFORMATION: HCV Core Antibody VH Region CDR2 and NS4
      Antibody VH Region CDR2

<400> SEQUENCE: 43

Ile Asn Thr Glu Thr Gly Glu Pro
  1               5

<210> SEQ ID NO 44
<211> LENGTH: 13
<212> TYPE: PRT
<213> ORGANISM: Artificial Sequence
<220> FEATURE:
<223> OTHER INFORMATION: HCV Core Antibody VH Region CDR3

<400> SEQUENCE: 44

Ala Arg Gly Gly Gly Val Arg Arg Gln Val Met Asp Tyr
  1               5                  10

<210> SEQ ID NO 45
<211> LENGTH: 12
<212> TYPE: PRT
<213> ORGANISM: Artificial Sequence
<220> FEATURE:
<223> OTHER INFORMATION: HCV Core Antibody VL Region CDR1

<400> SEQUENCE: 45

```
Gln Ser Leu Leu Asn Ser Arg Thr Arg Lys Asn Tyr
1               5                   10
```

```
<210> SEQ ID NO 46
<211> LENGTH: 3
<212> TYPE: PRT
<213> ORGANISM: Artificial Sequence
<220> FEATURE:
<223> OTHER INFORMATION: HCV Core Antibody VL Region CDR2 and HCV NS5
      Antibody VL Region CDR2

<400> SEQUENCE: 46

Trp Ala Ser
1
```

```
<210> SEQ ID NO 47
<211> LENGTH: 8
<212> TYPE: PRT
<213> ORGANISM: Artificial Sequence
<220> FEATURE:
<223> OTHER INFORMATION: HCV Core Antibody VL Region CDR3

<400> SEQUENCE: 47

Lys Gln Ser Tyr Asn Leu Tyr Thr
1               5
```

```
<210> SEQ ID NO 48
<211> LENGTH: 8
<212> TYPE: PRT
<213> ORGANISM: Artificial Sequence
<220> FEATURE:
<223> OTHER INFORMATION: HCV Core Antibody VH Region CDR1

<400> SEQUENCE: 48

Gly Tyr Thr Phe Thr Asn Tyr Gly
1               5
```

```
<210> SEQ ID NO 49
<211> LENGTH: 8
<212> TYPE: PRT
<213> ORGANISM: Artificial Sequence
<220> FEATURE:
<223> OTHER INFORMATION: HCV Core Antibody VH Region CDR2

<400> SEQUENCE: 49

Ile Asn Thr Asn Thr Gly Glu Pro
1               5
```

```
<210> SEQ ID NO 50
<211> LENGTH: 18
<212> TYPE: PRT
<213> ORGANISM: Artificial Sequence
<220> FEATURE:
<223> OTHER INFORMATION: HCV Core Antibody VH Region CDR3

<400> SEQUENCE: 50

Ala Arg Ala Gly Gly Asp Tyr Tyr Asp Ser Ser Tyr Asp Tyr Ala Met
1               5                   10                  15
Asp Tyr
```

```
<210> SEQ ID NO 51
<211> LENGTH: 10
<212> TYPE: PRT
<213> ORGANISM: Artificial Sequence
<220> FEATURE:
<223> OTHER INFORMATION: HCV Core Antibody VL Region CDR1

<400> SEQUENCE: 51
```

```
Gln Ser Val Asp Tyr Asp Gly Asp Ser Tyr
1               5                   10

<210> SEQ ID NO 52
<211> LENGTH: 3
<212> TYPE: PRT
<213> ORGANISM: Artificial Sequence
<220> FEATURE:
<223> OTHER INFORMATION: HCV Core Antibody VL Region CDR2

<400> SEQUENCE: 52

Ala Ala Ser
1

<210> SEQ ID NO 53
<211> LENGTH: 9
<212> TYPE: PRT
<213> ORGANISM: Artificial Sequence
<220> FEATURE:
<223> OTHER INFORMATION: HCV Core Antibody VL Region CDR3

<400> SEQUENCE: 53

Gln Gln Ser Asn Glu Asp Pro Trp Thr
1               5

<210> SEQ ID NO 54
<211> LENGTH: 8
<212> TYPE: PRT
<213> ORGANISM: Artificial Sequence
<220> FEATURE:
<223> OTHER INFORMATION: HCV NS3 Antibody VH Region CDR1

<400> SEQUENCE: 54

Gly Phe Thr Phe Ser Asp Tyr Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: HCV NS3 Antibody VH Region CDR2

<400> SEQUENCE: 55

Ile Ser Asn Gly Ala Gly Ser Thr
1               5

<210> SEQ ID NO 56
<211> LENGTH: 10
<212> TYPE: PRT
<213> ORGANISM: Artificial Sequence
<220> FEATURE:
<223> OTHER INFORMATION: HCV NS3 Antibody VH Region CDR3

<400> SEQUENCE: 56

Ala Arg Gly Leu Trp Asp Gly Leu Asp Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: HCV NS3 Antibody VL Region CDR1

<400> SEQUENCE: 57

Gln Ser Leu Val His Ser Asn Gly Asn Thr Tyr
```

<210> SEQ ID NO 58
<211> LENGTH: 3
<212> TYPE: PRT
<213> ORGANISM: Artificial Sequence
<220> FEATURE:
<223> OTHER INFORMATION: HCV NS3 Antibody VL Region CDR2 and NS4
      Antibody VL Region CDR2

<400> SEQUENCE: 58

Lys Val Ser
1

<210> SEQ ID NO 59
<211> LENGTH: 9
<212> TYPE: PRT
<213> ORGANISM: Artificial Sequence
<220> FEATURE:
<223> OTHER INFORMATION: HCV NS3 Antibody VL Region CDR3

<400> SEQUENCE: 59

Ser Gln Ser Thr His Val Pro Tyr Thr
1               5

<210> SEQ ID NO 60
<211> LENGTH: 8
<212> TYPE: PRT
<213> ORGANISM: Artificial Sequence
<220> FEATURE:
<223> OTHER INFORMATION: HCV NS4 Antibody VH Region CDR1

<400> SEQUENCE: 60

Gly Tyr Thr Phe Thr Asp Tyr Ser
1               5

<210> SEQ ID NO 61
<211> LENGTH: 7
<212> TYPE: PRT
<213> ORGANISM: Artificial Sequence
<220> FEATURE:
<223> OTHER INFORMATION: HCV NS4 Antibody VH Region CDR3

<400> SEQUENCE: 61

Thr Arg Gly Gly Thr Gly Tyr
1               5

<210> SEQ ID NO 62
<211> LENGTH: 11
<212> TYPE: PRT
<213> ORGANISM: Artificial Sequence
<220> FEATURE:
<223> OTHER INFORMATION: HCV NS4 Antibody VL Region CDR1

<400> SEQUENCE: 62

Gln Ser Leu Val Tyr Ser Asn Gly Asn Thr Tyr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: HCV NS4 Antibody VL Region CDR3

<400> SEQUENCE: 63

Ser Gln Ser Thr His Val Pro Trp Thr
1               5

<210> SEQ ID NO 64
<211> LENGTH: 8
<212> TYPE: PRT
<213> ORGANISM: Artificial Sequence
<220> FEATURE:
<223> OTHER INFORMATION: HCV NS5 Antibody VH Region CDR1

<400> SEQUENCE: 64

Gly Phe Asn Ile Lys Asp Thr Tyr
 1               5

<210> SEQ ID NO 65
<211> LENGTH: 8
<212> TYPE: PRT
<213> ORGANISM: Artificial Sequence
<220> FEATURE:
<223> OTHER INFORMATION: HCV NS5 Antibody VH Region CDR2

<400> SEQUENCE: 65

Ile Asp Pro Ala Asn Gly Asn Thr
 1               5

<210> SEQ ID NO 66
<211> LENGTH: 8
<212> TYPE: PRT
<213> ORGANISM: Artificial Sequence
<220> FEATURE:
<223> OTHER INFORMATION: HCV NS5 Antibody VH Region CDR3

<400> SEQUENCE: 66

Ala Arg Ser Arg Glu Phe Ala Tyr
 1               5

<210> SEQ ID NO 67
<211> LENGTH: 12
<212> TYPE: PRT
<213> ORGANISM: Artificial Sequence
<220> FEATURE:
<223> OTHER INFORMATION: HCV NS5 Antibody VL Region CDR1

<400> SEQUENCE: 67

Gln Ser Leu Leu Tyr Ser Ser Asn Gln Lys Asn Tyr
 1               5                  10

<210> SEQ ID NO 68
<211> LENGTH: 9
<212> TYPE: PRT
<213> ORGANISM: Artificial Sequence
<220> FEATURE:
<223> OTHER INFORMATION: HCV NS5 Antibody VL Region CDR3

<400> SEQUENCE: 68

Gln Gln Tyr Tyr Ser Tyr Pro Leu Thr
 1               5

<210> SEQ ID NO 69
<211> LENGTH: 24
<212> TYPE: DNA
<213> ORGANISM: Artificial Sequence
<220> FEATURE:
<223> OTHER INFORMATION: Sequence encoding HCV Core Antibody VH Region
      CDR1

<400> SEQUENCE: 69
ggttatacct tcacagacta tcca                                           24

```
<210> SEQ ID NO 70
<211> LENGTH: 24
<212> TYPE: DNA
<213> ORGANISM: Artificial Sequence
<220> FEATURE:
<223> OTHER INFORMATION: Sequence encoding HCV Core Antibody VH Region
      CDR2 and NS4 Antibody VH Region CDR2

<400> SEQUENCE: 70
ataaacactg agactggtga gcca                                          24

<210> SEQ ID NO 71
<211> LENGTH: 39
<212> TYPE: DNA
<213> ORGANISM: Artificial Sequence
<220> FEATURE:
<223> OTHER INFORMATION: Sequence encoding HCV Core Antibody VH Region
      CDR3

<400> SEQUENCE: 71
gctagagggg gtggggtccg acgccaggtt atggactac                          39

<210> SEQ ID NO 72
<211> LENGTH: 36
<212> TYPE: DNA
<213> ORGANISM: Artificial Sequence
<220> FEATURE:
<223> OTHER INFORMATION: Sequence encoding HCV Core Antibody VL Region
      CDR1

<400> SEQUENCE: 72
cagagtctgc tcaatagtag aacccgaaag aactac                             36

<210> SEQ ID NO 73
<211> LENGTH: 9
<212> TYPE: DNA
<213> ORGANISM: Artificial Sequence
<220> FEATURE:
<223> OTHER INFORMATION: Sequence encoding HCV Core Antibody VL Region
      CDR2 and NS5 Antibody VL Region CDR2

<400> SEQUENCE: 73 tgggcatcc                                                            9

<210> SEQ ID NO 74
<211> LENGTH: 24
<212> TYPE: DNA
<213> ORGANISM: Artificial Sequence
<220> FEATURE:
<223> OTHER INFORMATION: Sequence encoding HCV Core Antibody VL Region
      CDR3

<400> SEQUENCE: 74
aagcaatctt ataatctgta cacg                                          24

<210> SEQ ID NO 75
<211> LENGTH: 24
<212> TYPE: DNA
<213> ORGANISM: Artificial Sequence
<220> FEATURE:
<223> OTHER INFORMATION: Sequence encoding HCV Core Antibody VH Region
      CDR1

<400> SEQUENCE: 75
gggtatacct tcacaaacta tgga                                          24

<210> SEQ ID NO 76
<211> LENGTH: 24
```

```
<212> TYPE: DNA
<213> ORGANISM: Artificial Sequence
<220> FEATURE:
<223> OTHER INFORMATION: Sequence encoding HCV Core Antibody VH Region
      CDR2

<400> SEQUENCE: 76
ataaacacca acactggaga gcca                                              24

<210> SEQ ID NO 77
<211> LENGTH: 54
<212> TYPE: DNA
<213> ORGANISM: Artificial Sequence
<220> FEATURE:
<223> OTHER INFORMATION: Sequence encoding HCV Core Antibody VH Region
      CDR3

<400> SEQUENCE: 77
gcaagagcgg ggggagatta ctacgatagt agctacgact atgctatgga ctac            54

<210> SEQ ID NO 78
<211> LENGTH: 30
<212> TYPE: DNA
<213> ORGANISM: Artificial Sequence
<220> FEATURE:
<223> OTHER INFORMATION: Sequence encoding HCV Core Antibody VL Region
      CDR1

<400> SEQUENCE: 78
caaagtgttg attatgatgg tgatagttat                                        30

<210> SEQ ID NO 79
<211> LENGTH: 9
<212> TYPE: DNA
<213> ORGANISM: Artificial Sequence
<220> FEATURE:
<223> OTHER INFORMATION: Sequence encoding HCV Core Antibody VL Region
      CDR2

<400> SEQUENCE: 79 gctgcatcc                                                                9

<210> SEQ ID NO 80
<211> LENGTH: 27
<212> TYPE: DNA
<213> ORGANISM: Artificial Sequence
<220> FEATURE:
<223> OTHER INFORMATION: Sequence encoding HCV Core Antibody VL Region
      CDR3

<400> SEQUENCE: 80
cagcaaagta atgaggatcc gtggacg                                           27

<210> SEQ ID NO 81
<211> LENGTH: 24
<212> TYPE: DNA
<213> ORGANISM: Artificial Sequence
<220> FEATURE:
<223> OTHER INFORMATION: Sequence encoding HCV NS3 Antibody VH Region
      CDR1

<400> SEQUENCE: 81
ggattcactt tcagtgacta ttat                                              24

<210> SEQ ID NO 82
<211> LENGTH: 24
<212> TYPE: DNA
<213> ORGANISM: Artificial Sequence
```

```
<220> FEATURE:
<223> OTHER INFORMATION: Sequence encoding HCV NS3 Antibody VH Region
      CDR2

<400> SEQUENCE: 82
attagtaatg gtgctggtag cacc                                             24

<210> SEQ ID NO 83
<211> LENGTH: 30
<212> TYPE: DNA
<213> ORGANISM: Artificial Sequence
<220> FEATURE:
<223> OTHER INFORMATION: Sequence encoding HCV NS3 Antibody VH Region
      CDR3

<400> SEQUENCE: 83
gcaagaggcc tctgggacgg ccttgactac                                       30

<210> SEQ ID NO 84
<211> LENGTH: 33
<212> TYPE: DNA
<213> ORGANISM: Artificial Sequence
<220> FEATURE:
<223> OTHER INFORMATION: Sequence encoding HCV NS3 Antibody VL Region
      CDR1

<400> SEQUENCE: 84
cagagccttg tacacagtaa tggaaacacc tat                                   33

<210> SEQ ID NO 85
<211> LENGTH: 9
<212> TYPE: DNA
<213> ORGANISM: Artificial Sequence
<220> FEATURE:
<223> OTHER INFORMATION: Sequence encoding HCV NS3 Antibody VL Region
      CDR2 and NS4 Antibody VL Region CDR2

<400> SEQUENCE: 85 aaagtttcc                                                               9

<210> SEQ ID NO 86
<211> LENGTH: 27
<212> TYPE: DNA
<213> ORGANISM: Artificial Sequence
<220> FEATURE:
<223> OTHER INFORMATION: Sequence encoding HCV NS3 Antibody VL Region
      CDR3

<400> SEQUENCE: 86
tctcaaagta cacatgttcc gtacacg                                          27

<210> SEQ ID NO 87
<211> LENGTH: 24
<212> TYPE: DNA
<213> ORGANISM: Artificial Sequence
<220> FEATURE:
<223> OTHER INFORMATION: Sequence encoding HCV NS4 Antibody VH Region
      CDR1

<400> SEQUENCE: 87
ggttatacct tcacagacta ttca                                             24

<210> SEQ ID NO 88
<211> LENGTH: 21
<212> TYPE: DNA
<213> ORGANISM: Artificial Sequence
<220> FEATURE:
<223> OTHER INFORMATION: Sequence encoding HCV NS4 Antibody VH Region
```

-continued

CDR3

<400> SEQUENCE: 88
actaggggag gcacgggcta c                                              21

<210> SEQ ID NO 89
<211> LENGTH: 33
<212> TYPE: DNA
<213> ORGANISM: Artificial Sequence
<220> FEATURE:
<223> OTHER INFORMATION: Sequence encoding HCV NS4 Antibody VL Region
      CDR1

<400> SEQUENCE: 89
cagagccttg tatacagtaa tggaaacacc tat                                 33

<210> SEQ ID NO 90
<211> LENGTH: 27
<212> TYPE: DNA
<213> ORGANISM: Artificial Sequence
<220> FEATURE:
<223> OTHER INFORMATION: Sequence encoding HCV NS4 Antibody VL Region
      CDR3

<400> SEQUENCE: 90
tctcaaagta cacatgttcc gtggacg                                        27

<210> SEQ ID NO 91
<211> LENGTH: 24
<212> TYPE: DNA
<213> ORGANISM: Artificial Sequence
<220> FEATURE:
<223> OTHER INFORMATION: Sequence encoding HCV NS5 Antibody VH Region
      CDR1

<400> SEQUENCE: 91
ggcttcaaca ttaaagacac ctat                                           24

<210> SEQ ID NO 92
<211> LENGTH: 24
<212> TYPE: DNA
<213> ORGANISM: Artificial Sequence
<220> FEATURE:
<223> OTHER INFORMATION: Sequence encoding HCV NS5 Antibody VH Region
      CDR2

<400> SEQUENCE: 92
attgatcctg cgaatggtaa tact                                           24

<210> SEQ ID NO 93
<211> LENGTH: 24
<212> TYPE: DNA
<213> ORGANISM: Artificial Sequence
<220> FEATURE:
<223> OTHER INFORMATION: Sequence encoding HCV NS5 Antibody VH Region
      CDR3

<400> SEQUENCE: 93
gctagatcgc gggagtttgc ttac                                           24

<210> SEQ ID NO 94
<211> LENGTH: 36
<212> TYPE: DNA
<213> ORGANISM: Artificial Sequence
<220> FEATURE:
<223> OTHER INFORMATION: Sequence encoding HCV NS5 Antibody VL Region
      CDR1

```
<400> SEQUENCE: 94
cagagccttt tatatagtag caatcaaaag aactac                    36

<210> SEQ ID NO 95
<211> LENGTH: 27
<212> TYPE: DNA
<213> ORGANISM: Artificial Sequence
<220> FEATURE:
<223> OTHER INFORMATION: Sequence encoding HCV NS5 Antibody VL Region
      CDR3

<400> SEQUENCE: 95
cagcaatatt atagctatcc gctcacg                              27

<210> SEQ ID NO 96
<211> LENGTH: 37
<212> TYPE: DNA
<213> ORGANISM: Artificial Sequence
<220> FEATURE:
<223> OTHER INFORMATION: HCV Core Antibody VL 5' Primer

<400> SEQUENCE: 96 aaatttcgc gatgcgacat tgtgctgacc caatctc                    37

<210> SEQ ID NO 97
<211> LENGTH: 34
<212> TYPE: DNA
<213> ORGANISM: Artificial Sequence
<220> FEATURE:
<223> OTHER INFORMATION: HCV Core Antibody VL 3' Primer

<400> SEQUENCE: 97
actactcgta cgtttgattt ccagcttggt gcct                      34

<210> SEQ ID NO 98
<211> LENGTH: 55
<212> TYPE: DNA
<213> ORGANISM: Artificial Sequence
<220> FEATURE:
<223> OTHER INFORMATION: HCV Core Antibody VH 5' Primer

<400> SEQUENCE: 98 aaatttcgc gattttaaaa ggtgtccagt gtcagatcca gttggtgcag tctgg    55

<210> SEQ ID NO 99
<211> LENGTH: 36
<212> TYPE: DNA
<213> ORGANISM: Artificial Sequence
<220> FEATURE:
<223> OTHER INFORMATION: HCV Core Antibody VH 3' Primer

<400> SEQUENCE: 99
tcctttgtcg acgctgagga gacggtgact gaggtt                    36

<210> SEQ ID NO 100
<211> LENGTH: 8
<212> TYPE: PRT
<213> ORGANISM: Artificial Sequence
<220> FEATURE:
<223> OTHER INFORMATION: HCV Core Antigenic Fragment

<400> SEQUENCE: 100

Gln Ile Val Gly Gly Val Tyr Leu
 1               5

<210> SEQ ID NO 101
```

```
<211> LENGTH: 8
<212> TYPE: PRT
<213> ORGANISM: Artificial Sequence
<220> FEATURE:
<223> OTHER INFORMATION: HCV Core Antigenic Fragment
<220> FEATURE:
<221> NAME/KEY: VARIANT
<222> LOCATION: 2, 6, 7
<223> OTHER INFORMATION: Xaa = Any Amino Acid

<400> SEQUENCE: 101

Gln Xaa Val Gly Gly Xaa Xaa Leu
 1               5

<210> SEQ ID NO 102
<211> LENGTH: 8
<212> TYPE: PRT
<213> ORGANISM: Artificial Sequence
<220> FEATURE:
<223> OTHER INFORMATION: HCV Core Antigenic Fragment
<220> FEATURE:
<221> NAME/KEY: VARIANT
<222> LOCATION: 2, 6, 7
<223> OTHER INFORMATION: Xaa1, Xaa2, and Xaa3 = Ala or Gly

<400> SEQUENCE: 102

Gln Xaa Val Gly Gly Xaa Xaa Leu
 1               5

<210> SEQ ID NO 103
<211> LENGTH: 12
<212> TYPE: PRT
<213> ORGANISM: Artificial Sequence
<220> FEATURE:
<223> OTHER INFORMATION: HCV NS3 Antigenic Fragment

<400> SEQUENCE: 103

Asp Phe Val Pro Val Glu Ser Leu Glu Thr Thr Met
 1               5                  10

<210> SEQ ID NO 104
<211> LENGTH: 12
<212> TYPE: PRT
<213> ORGANISM: Artificial Sequence
<220> FEATURE:
<223> OTHER INFORMATION: HCV NS3 Antigenic Fragment
<220> FEATURE:
<221> NAME/KEY: VARIANT
<222> LOCATION: 5, 7, 10, 11
<223> OTHER INFORMATION: Xaa = Any Amino Acid

<400> SEQUENCE: 104

Asp Phe Val Pro Xaa Glu Xaa Leu Glu Xaa Xaa Met
 1               5                  10

<210> SEQ ID NO 105
<211> LENGTH: 12
<212> TYPE: PRT
<213> ORGANISM: Artificial Sequence
<220> FEATURE:
<223> OTHER INFORMATION: HCV NS3 Antigenic Fragment
<220> FEATURE:
<221> NAME/KEY: VARIANT
<222> LOCATION: 5, 7, 10, 11
<223> OTHER INFORMATION: Xaa1, Xaa2, Xaa3, and Xaa4 = Ala or Gly

<400> SEQUENCE: 105

Asp Phe Val Pro Xaa Glu Xaa Leu Glu Xaa Xaa Met
 1               5                  10
```

<210> SEQ ID NO 106
<211> LENGTH: 6
<212> TYPE: PRT
<213> ORGANISM: Artificial Sequence
<220> FEATURE:
<223> OTHER INFORMATION: HCV NS4 Antigenic Fragment

<400> SEQUENCE: 106

Leu Tyr Arg Glu Phe Asp
 1               5

<210> SEQ ID NO 107
<211> LENGTH: 6
<212> TYPE: PRT
<213> ORGANISM: Artificial Sequence
<220> FEATURE:
<223> OTHER INFORMATION: HCV NS4 Antigenic Fragment
<220> FEATURE:
<221> NAME/KEY: VARIANT
<222> LOCATION: 3
<223> OTHER INFORMATION: Xaa = Any Amino Acid

<400> SEQUENCE: 107

Leu Tyr Xaa Glu Phe Asp
 1               5

<210> SEQ ID NO 108
<211> LENGTH: 6
<212> TYPE: PRT
<213> ORGANISM: Artificial Sequence
<220> FEATURE:
<223> OTHER INFORMATION: HCV NS4 Antigenic Fragment
<220> FEATURE:
<221> NAME/KEY: VARIANT
<222> LOCATION: 3
<223> OTHER INFORMATION: Xaa = Ala or Gly

<400> SEQUENCE: 108

Leu Tyr Xaa Glu Phe Asp
 1               5

<210> SEQ ID NO 109
<211> LENGTH: 11
<212> TYPE: PRT
<213> ORGANISM: Artificial Sequence
<220> FEATURE:
<223> OTHER INFORMATION: HCV NS5 Antigenic Fragment

<400> SEQUENCE: 109

Pro Leu Glu Gly Glu Pro Gly Asp Pro Asp Leu
 1               5                  10

<210> SEQ ID NO 110
<211> LENGTH: 11
<212> TYPE: PRT
<213> ORGANISM: Artificial Sequence
<220> FEATURE:
<223> OTHER INFORMATION: HCV NS5 Antigenic Fragment
<220> FEATURE:
<221> NAME/KEY: VARIANT
<222> LOCATION: 7, 10
<223> OTHER INFORMATION: Xaa = Any Amino Acid

<400> SEQUENCE: 110

Pro Leu Glu Gly Glu Pro Xaa Asp Pro Xaa Leu
 1               5                  10

<210> SEQ ID NO 111
<211> LENGTH: 11
<212> TYPE: PRT

-continued

```
<213> ORGANISM: Artificial Sequence
<220> FEATURE:
<223> OTHER INFORMATION: HCV NS5 Antigenic Fragment
<220> FEATURE:
<221> NAME/KEY: VARIANT
<222> LOCATION: 7, 10
<223> OTHER INFORMATION: Xaa1 and Xaa2 = Ala or Gly

<400> SEQUENCE: 111

Pro Leu Glu Gly Glu Pro Xaa Asp Pro Xaa Leu
 1               5                  10
```